(12) United States Patent
Perret et al.

(10) Patent No.: US 9,347,052 B2
(45) Date of Patent: May 24, 2016

(54) ANTI-FH APTAMERS, METHOD FOR PRODUCING SAME, AND USES THEREOF

(71) Applicant: LABORATOIRE FRANCAIS DU FRACTIONNEMENT ET DES BIOTECHNOLOGIES, Les Ulis (FR)

(72) Inventors: Gerald Perret, Choisy le Roi (FR); Agnes Cibiel, Avon (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 0 days.

(21) Appl. No.: 14/360,735

(22) PCT Filed: Nov. 28, 2012

(86) PCT No.: PCT/IB2012/056786
§ 371 (c)(1),
(2) Date: May 27, 2014

(87) PCT Pub. No.: WO2013/080134
PCT Pub. Date: Jun. 6, 2013

(65) Prior Publication Data
US 2014/0329289 A1 Nov. 6, 2014

(30) Foreign Application Priority Data
Nov. 28, 2011 (FR) ..................... 11 60862

(51) Int. Cl.
C12N 15/115 (2010.01)
C12N 9/88 (2006.01)
C07K 14/47 (2006.01)

(52) U.S. Cl.
CPC . *C12N 9/88* (2013.01); *C07K 14/47* (2013.01); *C12N 15/115* (2013.01); *C12N 2310/16* (2013.01); *C12N 2310/351* (2013.01); *C12N 2330/30* (2013.01); *C12Y 402/01002* (2013.01)

(58) Field of Classification Search
CPC .......................... C12N 15/115; C12N 2310/16
See application file for complete search history.

(56) References Cited

U.S. PATENT DOCUMENTS

| 2006/0068416 A1 | 3/2006 | Schluesener et al. |
| 2008/0318841 A1 | 12/2008 | Chtourou et al. |
| 2012/0122179 A1* | 5/2012 | Perret ..................... C07K 1/22 435/188 |

FOREIGN PATENT DOCUMENTS

| EP | 0 668 931 B1 | 8/1995 |
| EP | 0 786 469 B1 | 7/1997 |
| EP | 1 493 825 A2 | 1/2005 |
| FR | 2894145 A1 | 6/2007 |
| WO | WO-91/19813 A1 | 12/1991 |
| WO | WO-02/077262 A2 | 10/2002 |
| WO | WO-2004/048511 A2 | 6/2004 |
| WO | WO-2004/055153 A2 | 7/2004 |
| WO | WO-2006/062716 A2 | 6/2006 |
| WO | WO-2007/038995 A1 | 4/2007 |
| WO | WO-2007/066017 A2 | 6/2007 |
| WO | WO-2008/113589 A1 | 9/2008 |
| WO | WO-2010/094901 A1 | 8/2010 |
| WO | WO-2011/053982 A2 | 5/2011 |
| WO | WO-2011/058284 A1 | 5/2011 |
| WO | WO-2011/058285 A1 | 5/2011 |

OTHER PUBLICATIONS

Bailon et al., "Affinity Chromatography: Methods and Protocols—An Overview of Affinity Chromatography", Humana Press Inc., 2000, table of contents, 10 pages.
Brumbt et al., "Chiral Stationary Phase Based on a Biostable L-RNA Aptamer", Anal Chem, 2005, vol. 77. pp. 1993-1998.
Cho et al., "Microbead-based affinity chromatography chip using RNA aptamer modified with photocleavable linker", Electrophoresis, 2004, vol. 25, Nos. 21-22, pp. 3730-3739.
Connor et al., "Aptamer stationary phase for protein capture in affinity capillary chromatography", Journal of Chomatography A, 2006, vol. 1111, No. 2, pp. 115-119.
Ellington and Szostak, "In vitro selection of RNA molecules that bind specific ligands", Nature, 1990, vol. 346, No. 6287, pp. 818-822.
Hermanson, Bioconjugate Technologies, Academic Press, San Diego, 1996, pp. 239-242.
International Search Report for International Application No. PCT/IB2012/056786 mailed May 22, 2013.
Michaud et al., "Immobilized DNA Aptamers as Target-Specific Chiral Stationary Phases for Resolution of Nucleoside and Amino Acid Derivative Enantiomers", Anal Chem., 2004, vol. 76, pp. 1015-1020.
Mohr et al., "Affinity Chromatography: Practical and Theoretical Aspects", Peter Mohr and Klaus Pommerening—Central Institute of Molecular Biology Academy of Sciences, Berlin-Buch, German Democratic Republic, Marcel Dekker, Inc., CRC Press, 1985, table of contents, 6 pages.
Ravelet et al., "Liquid chromatography, electrochromatography and capillary electrophoresis applications of DNA and RNA aptamers", Journal of Chromatography A, 2006, vol. 1117, No. 1, pp. 1-10.
Romig et al., "Aptamer affinity chromatography: combinatorial chemistry applied to protein purification", Journal of Chromatography B, 1999, vol. 731, No. 2, pp. 275-284.
Samoszuk et al., "A Peroxide-Generating Immunoconjugate Directed to Eosinophil Peroxidase Is Cytotoxic to Hodgkin's Disease Cells In Vitro", Antibody, Immunoconjugates Radiopharmaceuticals, 1989, vol. 2, No. 1, pp. 37-46.
Tuerk et al., "Systematic evolution of ligands by exponential enrichment: RNA ligands to bacteriophage T4 DNA polymerase", Science, 1990, vol. 249, No. 4968, pp. 505-510.
Zhao et al., "Aptamer-Modified Monolithic Capillary Chromatography for Protein Separation and Detection", Anal Chem., 2008, vol. 80, No. 10, pp. 3915-3920.

* cited by examiner

*Primary Examiner* — Jon E Angell
(74) *Attorney, Agent, or Firm* — Foley & Lardner LLP

(57) ABSTRACT

The invention relates to nucleic acid aptamers binding specifically to factor H, to a method for obtaining same, and to the uses thereof, in particular for the purposes of purifying factor H.

20 Claims, 8 Drawing Sheets

ANTI-FH APTAMERS, METHOD FOR PRODUCING SAME, AND USES THEREOF

FIELD OF THE INVENTION

The present invention relates to the field of obtaining preparations of purified factor H, for therapeutic use.

PRIOR ART

Complement plays an essential role in the organism's defense against infectious agents and in the inflammatory process. It represents a helper system for immunity, in particular for the humoral response and for the innate response.

Factor H is the principal regulator of the alternative complement pathway. It acts both in the liquid phase and at the surface of cells. Initially denoted "beta 1 H globulin", this 155 kDa serum glycoprotein is also called factor H 1, FH, CFH or HF1. Factor H is synthesized in the liver, the macrophages, the fibroblasts, the endothelial cells and the platelets. The secreted form of the protein is composed of 20 repeating units (or short consensus repeats, SCRs) of 60 amino acids.

The anti-complement activity of factor H is reflected by the regulation of the level of immune complexes in the blood; it consequently contributes to the equilibrium between the processes resulting in their generation or in their degradation. Factor H reduces the half-life of the alternative C3 convertase (C3bBb) by binding C3b and by dissociating Bb and serves as a cofactor to factor I in the proteolysis of C3b, free or bound to the surface of cells, to give C3bi. Thus, the immune complexes composed of an antigen-antibody complex associated with the C3b complement component can no longer activate the subsequent complement cascade (components C5-C9).

Factor H has been proposed in the treatment of atypical hemolytic uremic syndrome (aHUS) associated with a hereditary abnormality of the complement system (patent application FR 2 894 145). Moreover, factor H is indicated for the treatment of chronic nephropathies (WO 2007/038995).

An appropriate source for preparing a preparation of factor H for therapeutic use is blood plasma. The blood plasma has been used for a long time for preparing blood-derived products of albumin type, immunoglobulin preparations, coagulation factor concentrates (factor VIII, factor IX, etc.), etc. Methods for fractionating plasma are known, making it possible to enrich certain fractions with desired products. Simplified schemes for modified Cohn/Oncley industrial plasma fractionation and for Kistler/Nitschmann industrial plasma fractionation are presented in patent application WO 2008/113589, which relates to a preparation of a factor H formulation from an ethanolic fraction.

Patent application WO 2007/066017 describes a method for purifying factor H comprising anion exchange chromatography followed by two steps of heparin-type affinity chromatography, and then, in order, cation exchange chromatography and anion exchange chromatography. Patent application WO 2008/113589 describes the obtaining of a purified factor H by affinity chromatography with heparin, from an ethanolic fraction of blood plasma, followed by anion exchange chromatography and cation exchange chromatography.

These methods remain imperfect, either because they consume too much heparin, which is an expensive product (WO 2007/066017), or because they do not achieve a level of purity of the factor which is totally satisfactory for therapeutic use (WO 2008/113589). The invention aims to solve these problems.

Patent applications WO 2011/058284 and WO 2011/058285 describe methods for purifying human factor H of plasma origin comprising, in particular, a succession of ion exchange chromatography steps, thereby encompassing at least one cation exchange chromatography step and at least one anion exchange chromatography step. The characteristics of these methods are specifically suited to the obtaining of purified factor H from human plasma fractions.

There is a need to have available novel methods for obtaining factor H in purified form, said methods being alternative methods or methods that are improved with respect to the known methods.

SUMMARY OF THE INVENTION

Novel tools, of use for detecting or purifying factor H, and also methods for detecting or purifying factor H in which these novel tools are used, are provided according to the invention.

The present invention provides nucleic aptamers which bind selectively to factor H, and also detection supports and affinity supports on which these nucleic aptamers are immobilized.

The present invention relates to nucleic aptamers which bind to factor H. Said nucleic aptamers encompass those comprising a nucleic acid having a sequence chosen from the sequences (i) SEQ ID No 3 to SEQ ID No 116, which includes SEQ ID No 4 to 116, (ii) SEQ ID No 117 to SEQ ID No 232 and (iii) SEQ ID No 239 to SEQ ID No 243.

Preferably, the nucleic aptamers above are obtained according to a method derived from the general method for obtaining aptamers known as "SELEX", said method possibly comprising one or more original steps able to confer on the aptamers obtained characteristics which increase their ability to reversibly bind to the target factor H, in particular under optimum conditions for carrying out a step of factor H enrichment by affinity chromatography.

In certain embodiments, the nucleic aptamers of the invention are characterized in that they bind to a factor H chosen from a plasma factor H, a recombinant factor H and a transgenic factor H.

In certain embodiments, the nucleic aptamers of the invention are characterized in that they bind to a factor H chosen from a human factor H and a non-human factor H.

In certain embodiments, the nucleic aptamers consist of ribonucleotide aptamers.

In certain other embodiments, the nucleic aptamers consist of deoxyribonucleotide aptamers.

The present invention also relates to an affinity support for the selective binding of factor H, comprising a solid support material on which nucleic aptamers as defined above are immobilized. It also relates to methods for obtaining said affinity support.

The present invention also relates to a method for purifying factor H, comprising the following steps:
a) bringing a sample containing a factor H into contact with an affinity support as defined above, in order to form complexes between (i) the nucleic aptamers immobilized on said affinity support and (ii) said factor H,
b) releasing the factor H from the complexes formed in step a), and
c) recovering the factor H in purified form.

This invention also relates to a purified composition of human factor H of plasma origin, substantially free of other plasma proteins.

The invention also relates to a purified composition of recombinant human factor H, substantially free of non-human proteins.

DESCRIPTION OF THE FIGURES

FIG. 1 illustrates the human factor H-binding capacity of the starting nucleic acid collection.

In FIG. 1A, the curves of binding of the nucleic acids of the starting library are located approximately at the level of the base signal of the buffer solution free of nucleic acids.

In FIG. 1B, the curves of binding of the human plasma factor H to the nucleic acids of the starting library are located approximately at the level of the base signal of the buffer solution free of factor H. Along the x-axis: time, expressed in seconds. Along the y-axis: resonance signal, expressed in arbitrary resonance units.

FIG. 2 illustrates the capacity of the nucleic acids selected after an increasing number of cycles of reiteration of the SELEX process to bind to human plasma factor H.

Curve no 1: curve of the selection buffer solution free of factor H. Curve no 2: curve of binding of the human plasma factor H at the final concentration of 200 nM. Curve no 3: curve of binding of the human plasma factor H at the final concentration of 400 nM.

Along the x-axis: time, expressed in seconds. Along the y-axis: resonance signal, expressed in arbitrary resonance units.

Figure 3:
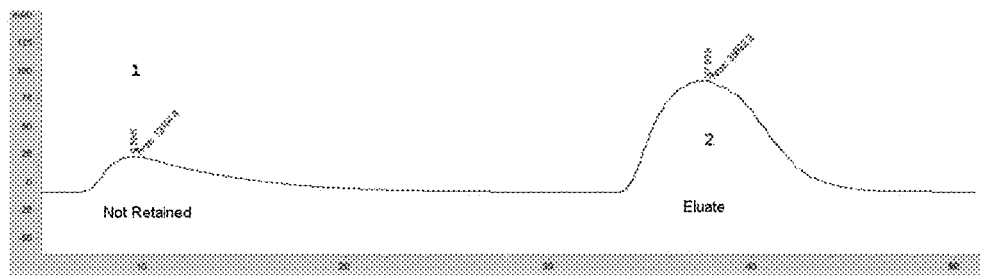

FIG. 3 illustrates a chromatography profile for a human plasma factor H purified using a conventional method including in particular a heparin affinity step on an affinity support on which anti-FH nucleic aptamers are immobilized. Along the x-axis: time, expressed in minutes. Along the y-axis: absorbance value (OD) at 254 nanometers.

Figure 4:
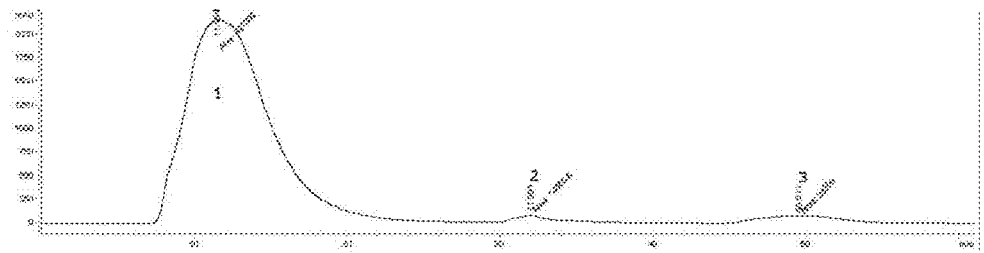

FIG. 4 illustrates a chromatography profile for a culture supernatant of cells producing a recombinant human factor H on an affinity support on which anti-FH nucleic aptamers are immobilized. Along the x-axis: time, expressed in minutes. Along the y-axis: absorbance value (OD) at 254 nanometers.

Figure 5A:
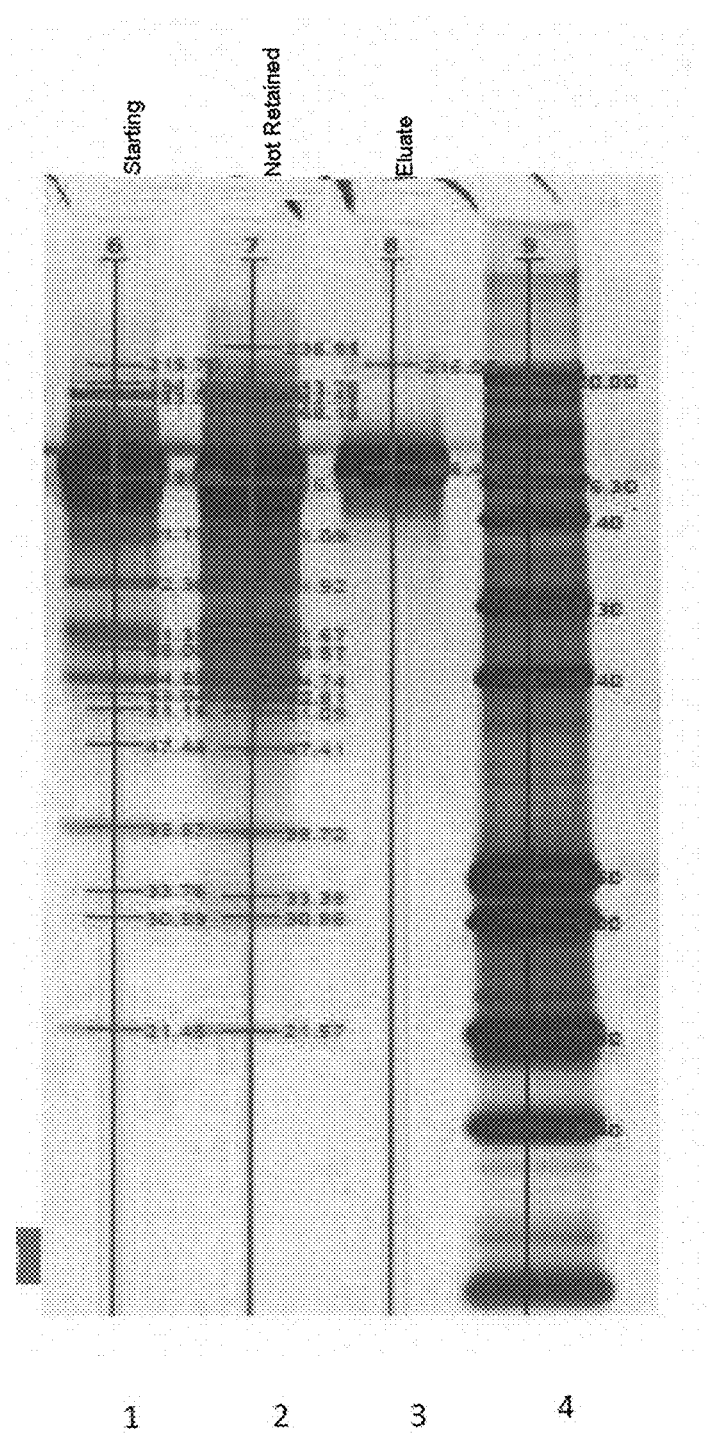

FIG. 5A is an image of an electrophoresis gel after silver nitrate staining. From left to right on the figure: Lane no 1: starting prepurified plasma FH sample; Lane no 2: fraction not retained after passing the prepurified plasma FH sample used in lane no 1 over an affinity support on which anti-FH nucleic aptamers are immobilized; Lane no 3: elution fraction after passing the prepurified plasma FH sample used in lane no 1 over an affinity support on which anti-FH nucleic aptamers are immobilized; Lane no 4: molecular weight markers.

Figure 5B:
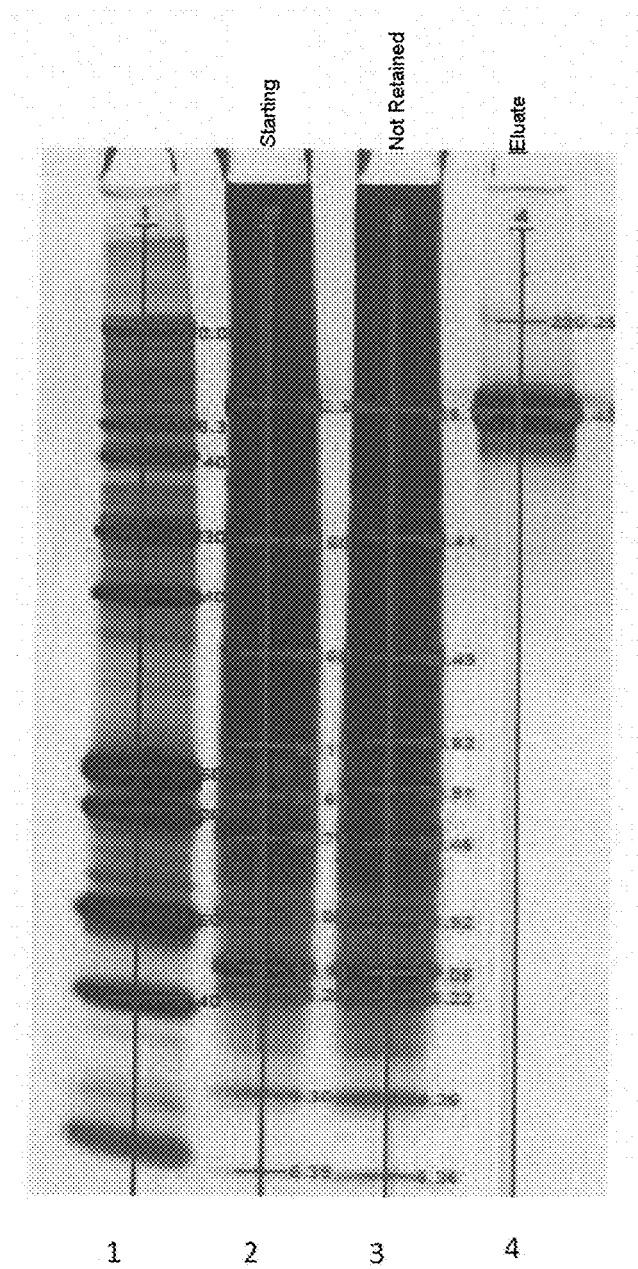

FIG. 5B is an image of an electrophoresis gel after silver nitrate staining. From left to right on the figure: Lane no 1: molecular weight markers; Lane no 2: sample of culture supernatant of cells producing a recombinant human factor H; Lane no 3: fraction not retained after passing the plasma sample used in lane no 1 over an affinity support on which anti-FH nucleic aptamers are immobilized; Lane no 4: elution fraction after passing the plasma sample used in lane no 1 over an affinity support on which anti-FH nucleic aptamers are immobilized.

Figure 6A:
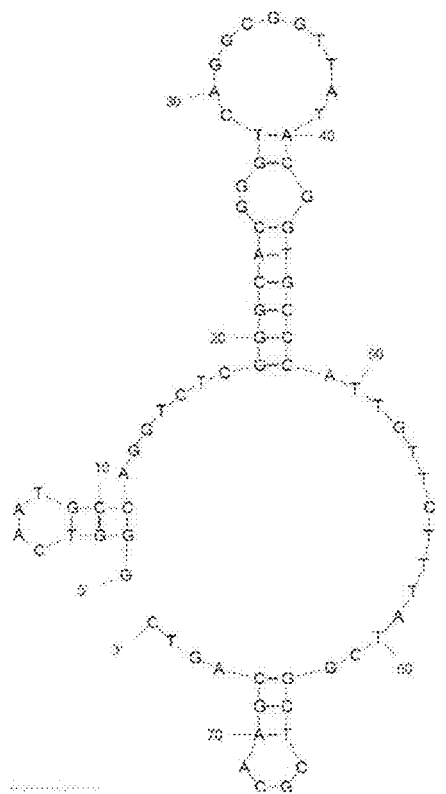
Figure 6B:
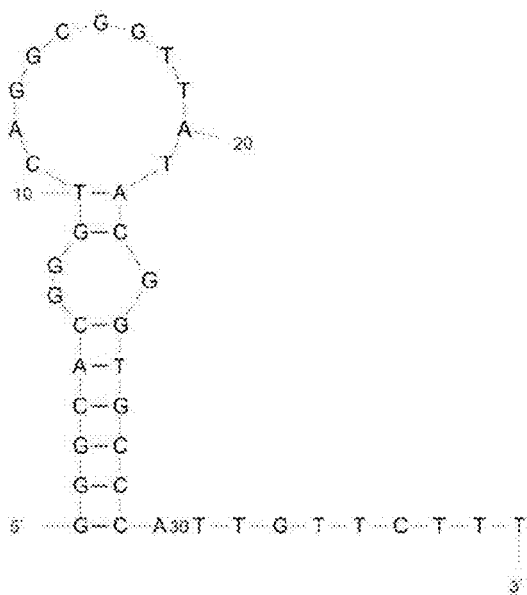

FIG. 6 is a representation of the secondary structure of the MaptH1.1 nucleic aptamer. FIG. 6A is a representation of the secondary structure of the complete MaptH1.1 aptamer. FIG. 6B is a representation of the secondary structure of the central part "SEQ ID No X" of the MaptH1.1 aptamer.

Figure 7:
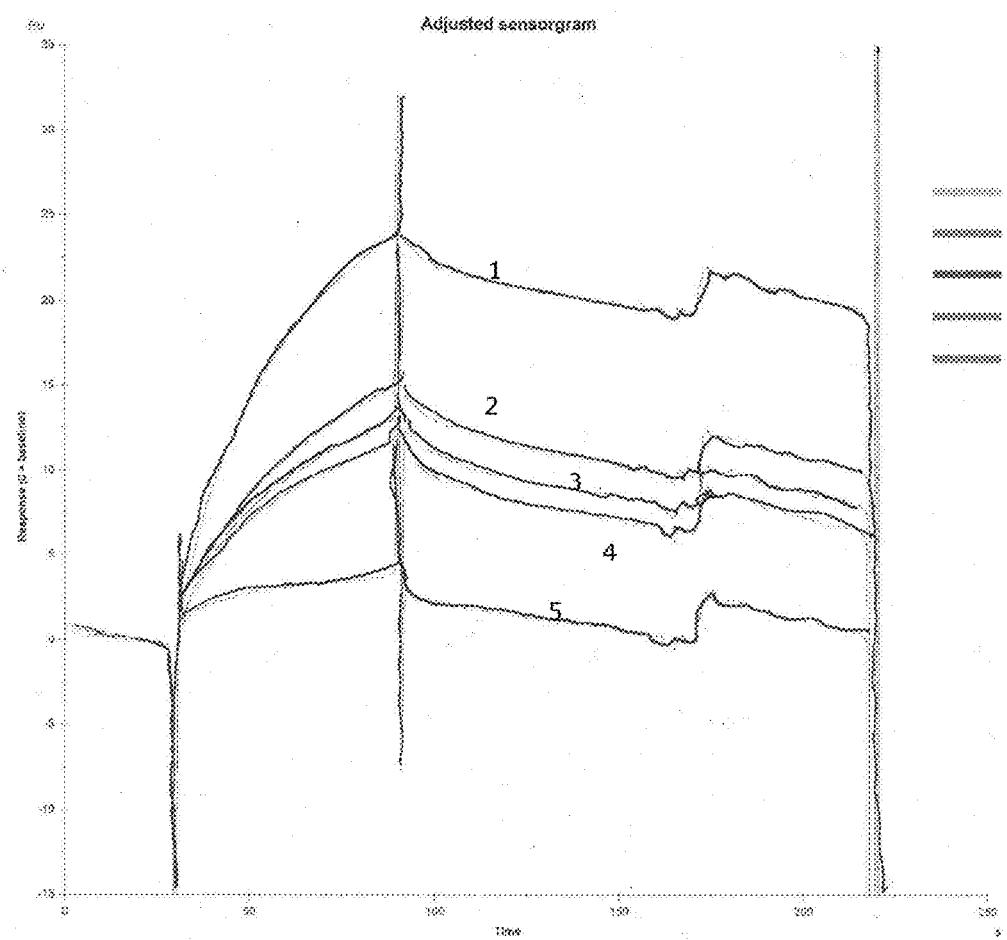

FIG. 7 represents the curves of binding to purified human plasma factor H of a variety of nucleic aptamers derived from the MaptH1.1 aptamer. The curves going from top to bottom on FIG. 7 represent the human factor H binding to the following respective aptamers: (1) MaptH1.1 N13-48, (2) MaptH1.1 N19-58, (3) MaptH1.1 N19-53; (4) MaptH1.1 N19-48 and (5) MaptH1.1 N22-45.

DETAILED DESCRIPTION OF THE INVENTION

The applicant has mainly endeavored to design novel methods for purifying factor H, in particular human factor H. To this end, the applicant has isolated and characterized novel ligands which have an ability to bind selectively to factor H. These novel ligands, the characteristics of which are explained in detail later in the present description, consist of nucleic acids, also called "nucleic aptamers", which bind selectively to factor H.

To the applicant's knowledge, nucleic aptamers which bind selectively to factor H are described for the first time in the present description.

The present invention provides methods for purifying factor H, in which advantage is taken of the binding properties of these novel ligands of the nucleic acid type.

The applicant has also endeavored to develop methods for obtaining nucleic aptamers which bind specifically to factor H.

The term "factor H" is intended to mean any protein having the amino acid sequence of the native factor H of a mammal, and in particular any protein having the amino acid sequence of human factor H. The term "factor H" also comprises the natural allelic variations and/or the naturally found isoforms of factor H, and any form or degree of glycosylation or other post-translational modification. Also included are the homologs or derivatives of factor H which have the same biological activity or a greater biological activity compared with the activity of the wild-type form and/or which have a sequence identity of at least 80%, preferably at least 85%, more preferably at least 90% relative to said wild-type form.

The term "biological activity" of factor H includes the ability to inhibit C3 convertase and/or to serve as a cofactor for factor I, resulting in the inhibition of the activation of the complement cascade. The activity of factor H may be measured in various ways, well known to those skilled in the art.

According to the invention, the term "nucleic aptamer" is intended to mean a single-stranded nucleic acid which binds selectively to factor H, which may also be denoted "anti-FH aptamer" for the purposes of the present description.

The detection of complexes formed between an anti-FH aptamer according to the invention and factor H may be easily carried out by those skilled in the art, for example by implementing a detection technique by surface plasmon resonance, including the Biacore® technique, as is illustrated in the examples. Those skilled in the art may also easily detect the formation of complexes between an anti-FH aptamer according to the invention and factor H by conventional techniques of the ELISA type, as is known by those skilled in the art.

It is shown in the examples that an anti-FH nucleic aptamer is capable of binding selectively to human factor H which has not undergone cleavage by proteolysis.

Generally, the anti-FH aptamers may consist of DNA (deoxyribonucleic acid) or RNA (ribonucleic acid) molecules and have a capacity to bind to factor H which is greater than the capacity to bind to a protein other than factor H.

An anti-FH aptamer may be obtained by means of methods which have been specially developed for the needs of the invention, and which are described in detail later in the present description.

In some embodiments, the anti-FH aptamers according to the invention have various common structural characteristics, including therein a sequence comprising, from the 5' end to the 3' end, successively (i) an invariable specific nucleotide sequence approximately 20 nucleotides in length, followed by (ii) a variable nucleotide sequence approximately 40 nucleotides in length, followed by (iii) an invariable specific nucleotide sequence approximately 20 nucleotides in length. It is specified that the variable nucleotide sequences (ii) may have a very strong nucleotide sequence identity between them.

In certain embodiments, said variable sequence (ii) has a length ranging from 15 to 50 nucleotides, as is described in detail later.

The methods for selecting anti-FH aptamers which are specified in the present description are of the type which makes it possible to obtain a set of anti-FH aptamers capable of recognizing factor H, in particular human factor H.

From a structural point of view, each element of the family of nucleic acids, or nucleic aptamers, capable of being obtained according to the invention, which bind specifically to factor H, comprises at least 15 consecutive nucleotides of a polynucleotide having at least 40% nucleotide identity with the nucleic acid of formula (I) below:

$$5'\text{-[SEQ ID No 1]}_x\text{-[SEQ ID No X]-[SEQ ID No 2]}_y\text{-}3' \quad \text{(I),}$$

in which:
"SEQ ID No X" consists of a nucleic acid having a sequence chosen from the sequences SEQ ID No 3 to SEQ ID No 116,
"x" is an integer equal to 0 or 1, and
"y" is an integer equal to 0 or 1.

The nucleic aptamers above encompass those of which the sequence SEQ ID No X has at least 40% nucleotide identity with a nucleic acid having a sequence chosen from the sequences SEQ ID No 3 to SEQ ID No 116. Encompassed are the nucleic aptamers of this type, the flanking sequences of which at the 5' and 3' ends have 100% nucleotide identity with the sequences SEQ ID No 1 and SEQ ID No 2, respectively.

In certain embodiments, the nucleic acid of sequence SEQ ID No X has a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides, the length of said nucleic acid being limited by the maximum length of the reference sequence from which it derives, said reference sequence being chosen from the sequences SEQ ID No 3 to SEQ ID No 116, which includes SEQ ID No 4 to 116.

In other embodiments, the nucleic acid of sequence SEQ ID No X has a length of 35, 36, 37, 38, 39, 40, 41, 42, 43, 44 or 45 nucleotides, the length of said nucleic acid being limited by the maximum length of the reference sequence from which it derives.

In certain other preferred embodiments, the nucleic acid of sequence SEQ ID No X has a length of 38, 39, 40 or 41 nucleotides.

As already previously mentioned, the nucleic acid of formula (I) has a length of at least 15 nucleotides.

In certain embodiments, the nucleic acid of formula (I) has a length of at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 or 81 nucleotides, which encompasses the nucleic acids having exactly each one of the specified lengths.

When the integer "x" is equal to 0 and the integer "y" is equal to 1, the nucleic aptamers of the invention encompass the nucleic acids comprising at least 15 consecutive nucleotides of a polynucleotide having at least 40% nucleotide identity with the nucleic acid of formula (I-1) below:

$$5'\text{-[SEQ ID No }X\text{]-[SEQ ID No 2]-}3' \quad \text{(I-1).}$$

The invention encompasses the nucleic aptamers having at least 15 consecutive nucleotides of a nucleic acid of formula (I-1) above. The invention also encompasses the nucleic aptamers having at least 40% nucleotide identity with a nucleic acid of formula (I-1) above. Encompassed are the nucleic aptamers of formula (I-1) of which the flanking sequence at the 3' end possesses 100% nucleotide identity with the sequence SEQ ID No 2.

When the integer "x" is equal to 1 and the integer "y" is equal to 0, the nucleic aptamers of the invention encompass the nucleic acids comprising at least 15 consecutive nucleotides of a polynucleotide having at least 40% nucleotide identity with the nucleic acid of formula (I-2) below:

$$5'\text{-[SEQ ID No 1]-[SEQ ID No }X\text{]-}3' \quad \text{(I-2).}$$

The invention encompasses the nucleic aptamers having at least 15 consecutive nucleotides of a nucleic acid of formula (I-2) above. The invention also encompasses the nucleic aptamers having at least 40% nucleotide identity with a nucleic acid of formula (I-2) above. Encompassed are the nucleic aptamers of formula (I-1) of which the flanking sequence at the 5' end possesses 100% nucleotide identity with the sequence SEQ ID No 1.

When the integer "x" is equal to 0 and the integer "y" is equal to 0, the nucleic aptamers of the invention encompass the nucleic acids comprising at least 15 consecutive nucleotides of a polynucleotide having at least 40% nucleotide identity with the nucleic acid of formula (I-3) below:

$$5'\text{-[SEQ ID No }X\text{]-}3' \quad \text{(I-3).}$$

The invention encompasses the nucleic aptamers having at least 15 consecutive nucleotides of a nucleic acid of formula (I-3) above. The invention also encompasses the nucleic aptamers having at least 40% nucleotide identity with a nucleic acid of formula (I-3) above.

The nucleic aptamers according to the invention encompass the nucleic acids comprising at least 15 consecutive nucleotides of a nucleic acid having a sequence chosen from the sequences SEQ ID No 117 to SEQ ID No 232. The nucleic aptamers according to the invention also encompass the nucleic acids having at least 40% nucleotide identity with a nucleic acid having a sequence chosen from the sequences SEQ ID No 117 to SEQ ID No 232.

The nucleic aptamers according to the invention encompass in particular the nucleic acids comprising at least 15 consecutive nucleotides of a nucleic acid having a sequence chosen from the sequences SEQ ID No 3 to SEQ ID No 116, which includes SEQ ID No 4 to 116. The nucleic aptamers according to the invention also encompass the nucleic acids having at least 40% nucleotide identity with a nucleic acid having a sequence chosen from the sequences SEQ ID No 3 to SEQ ID No 116, which includes SEQ ID No 4 to 116.

In certain embodiments of a nucleic acid of the invention comprising the sequence SEQ ID No X, said sequence SEQ ID No X is chosen from the group consisting of the nucleic acids having at least 15 consecutive nucleotides of a sequence chosen from the sequences SEQ ID No 3 to SEQ ID No 116, which includes SEQ ID No 4 to 116.

In certain embodiments of a nucleic acid of the invention comprising the sequence SEQ ID No X, said sequence SEQ ID No X is chosen from the group consisting of the nucleic acids having at least 40% nucleotide identity with a sequence chosen from the sequences SEQ ID No 3 to SEQ ID No 116, which includes SEQ ID No 4 to 116.

In certain embodiments of a nucleic aptamer of the invention, said aptamer is chosen from the nucleic acids comprising a sequence chosen from the sequences SEQ ID No 117 to SEQ ID No 232.

In certain embodiments of a nucleic aptamer of the invention, said aptamer is chosen from the nucleic acids comprising a sequence chosen from the sequences SEQ ID No 117 to SEQ ID No 232.

In certain embodiments of a nucleic aptamer of the invention, said aptamer is chosen from the nucleic acids consisting of a sequence chosen from the sequences SEQ ID No 117 to SEQ ID No 232.

In certain embodiments of a nucleic aptamer of the invention, said aptamer is chosen from the nucleic acids consisting of a sequence chosen from the sequences SEQ ID No 117 to SEQ ID No 232.

The nucleic acids which bind selectively to factor H defined in the present description may exhibit structural homologies between them, i.e. may exhibit between them a high percentage nucleotide identity.

In particular, some of the nucleic acids which bind selectively to factor H may have in common identical nucleotide successions, which are denoted "consensus sequences" for the purposes of the present description.

For example, a first family of nucleic acids according to the invention, or "Family 1", which bind to factor H is the family of nucleic acids having sequences SEQ ID No 3 to SEQ ID No 42, which includes SEQ ID No 4 to 42, and SEQ ID No 117 to SEQ ID No 158. It is specified that the nucleic acids having sequences SEQ ID No 117 to SEQ ID No 156 comprise the sequences SEQ ID No 3 to SEQ ID No 42, which includes SEQ ID No 4 to 42, respectively. The nucleic acids of Family 1 are structurally related to one another at least because of the presence of a common consensus sequence of the "GGGTCGGGGTTATACG" type (SEQ ID No 233), it being understood that said consensus sequence is not necessarily found in the form of a continuous succession of nucleotides, it being possible for two contiguous nucleotides of said consensus sequence to be separated by one or more nucleotides in the reference sequence. By way of illustration, the consensus sequence of Family 1 is found, in the sequence SEQ ID No 3, in the form of the sequence "GGGTCTGGTGGTTATACG" (SEQ ID No 234).

A second family of nucleic acids according to the invention, or "Family 2", which bind to factor H is the family of nucleic acids having sequences SEQ ID No 43 to SEQ ID No 60 and SEQ ID No 159 to SEQ ID No 176. It is specified that the nucleic acids having sequence SEQ ID No 159 to SEQ ID No 176 comprise the sequences SEQ ID No 43 to SEQ ID No 60, respectively. The nucleic acids of Family 2 are structurally related to one another at least because of the presence of a common consensus sequence of the "CCGGTTACCTGGTGTTGTGGC" type (SEQ ID No 235), it being understood that said consensus sequence is not necessarily found in the form of a continuous succession of nucleotides, it being possible for two contiguous nucleotides of said consensus sequence to be separated by one or more nucleotides in the reference sequence.

A third family of nucleic acids according to the invention, or "Family 3", which bind to factor H is the family of nucleic acids having sequences SEQ ID No 61 to SEQ ID No 64, and SEQ ID No 177 to SEQ ID No 180. It is specified that the nucleic acids having sequence SEQ ID No 177 to SEQ ID No 180 comprise the sequences SEQ ID No 61 to SEQ ID No 64, respectively. The nucleic acids of Family 3 are structurally related to one another at least because of the presence of a common consensus sequence of the "GGAGGCTTTTACAGGCGGTGCG" type (SEQ ID No 236), it being understood that said consensus sequence is not necessarily found in the form of a continuous succession of nucleotides, it being possible for two contiguous nucleotides of said consensus sequence to be separated by one or more nucleotides in the reference sequence.

A fourth family of nucleic acids according to the invention, or "Family 4", which bind to factor H is the family of nucleic acids having the sequences SEQ ID No 65 to SEQ ID No 66 and SEQ ID No 181 to SEQ ID No 182. It is specified that the nucleic acids having sequence SEQ ID No 181 to SEQ ID No 182 comprise the sequences SEQ ID No 65 to SEQ ID No 66, respectively. The nucleic acids of Family 4 are structurally related to one another at least because of the presence of a common consensus sequence of the "GGGGGGGGTTGGGGGACCGTCCGTTTGAT" type (SEQ ID No 237), it being understood that said consensus sequence is not necessarily found in the form of a continuous succession of nucleotides, it being possible for two contiguous nucleotides of said consensus sequence to be separated by one or more nucleotides in the reference sequence.

A fifth family of nucleic acids according to the invention, or "Family 5", which bind to factor H is the family of nucleic acids having sequences SEQ ID No 67 to SEQ ID No 71 and SEQ ID No 183 to SEQ ID No 187. It is specified that the nucleic acids having sequence SEQ ID No 183 to SEQ ID No 187 comprise the sequences SEQ ID No 67 to SEQ ID No 71, respectively. The nucleic acids of Family 5 are structurally related to one another at least because of the presence of a common consensus sequence of the "TGTGGGGGGTTGGGG" type (SEQ ID No 238), it being understood that said consensus sequence is not necessarily found in the form of a continuous succession of nucleotides, it being possible for two contiguous nucleotides of said consensus sequence to be separated by one or more nucleotides in the reference sequence.

It results from the above that the present invention encompasses a family of single-stranded nucleic acids having at least 15 consecutive nucleotides of the succession of formula (I) defined above.

Generally, a polynucleotide having at least 15 consecutive nucleotides of a reference nucleic acid possesses at least 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or at least 80 consecutive nucleotides of said reference nucleic acid, the number of consecutive nucleotides being limited by the length of the reference nucleic acid.

It also results from the above that the present invention encompasses a family of single-stranded nucleic acids having at least 40% nucleotide identity with the succession of formula (I) defined above.

Generally, a first polynucleotide having at least 40% nucleotide identity with a second polynucleotide or nucleic acid possesses at least 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 100% nucleotide identity with said second polynucleotide or nucleic acid.

The "percentage identity" between two nucleic acid sequences, for the purposes of the present invention, is determined by comparing the two optimally aligned sequences through a comparison window.

The part of the nucleotide sequence in the comparison window may thus comprise additions or deletions (for example "gaps") compared with the reference sequence (which does not comprise these additions or these deletions) so as to obtain an optimal alignment between the two sequences.

The percentage identity is calculated by determining the number of positions at which an identical nucleic base is observed for the two sequences compared, then by dividing the number of positions at which there is identity between the two nucleic bases by the total number of positions in the comparison window, then by multiplying the result by one hundred in order to obtain the percentage nucleotide identity of the two sequences with respect to one another.

The optimal alignment of the sequences for the comparison may be carried out by computer using known algorithms.

Entirely preferably, the percentage sequence identity is determined using the CLUSTAL W software (version 1.82), the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAPH DISTANCES="hide".

In certain preferred embodiments of an anti-FH nucleic aptamer of the invention, said nucleic aptamer comprises at least 15 consecutive nucleotides of a polynucleotide having at least 80% nucleotide identity with the nucleic acid of formula (I), which encompasses the aptamers comprising at least 15 consecutive nucleotides of a polynucleotide having at least 81%, 82%, 83%, 84%, 85%, 86%, 87%, 88%, 89%, 90%, 91%, 92%, 93%, 94%, 95%, 96%, 97%, 98% or 100% nucleotide identity with said nucleic acid of formula (I).

The invention also relates to the anti-FH nucleic aptamers having at least 80% nucleotide identity with the nucleic acid of formula (I), which encompasses the aptamers having at least 81%, 82%, 83%, 84%, 85%, 86%, 87%, 88%, 89%, 90%, 91%, 92%, 93%, 94%, 95%, 96%, 97%, 98% or 100% nucleotide identity with said nucleic acid of formula (I).

The invention also relates to anti-FH nucleic aptamers comprising a polynucleotide having at least 80% nucleotide identity with a nucleic acid having a sequence chosen from the sequences SEQ ID No 3 to SEQ ID No 116, which includes SEQ ID No 4 to 116. Said anti-FH aptamers encompass the aptamers comprising a polynucleotide having at least 81%, 82%, 83%, 84%, 85%, 86%, 87%, 88%, 89%, 90%, 91%, 92%, 93%, 94%, 95%, 96%, 97%, 98% or 100% nucleotide identity with a nucleic acid having a sequence chosen from the sequences SEQ ID No 3 to SEQ ID No 116, which includes SEQ ID No 4 to 116.

The nucleic aptamers according to the invention encompass the nucleic aptamers having sequence SEQ ID No 117 to SEQ ID No 232. It is recalled that the aptamers having sequence SEQ ID No 117 to SEQ ID No 232 consist of aptamers of formula (I) in which the sequence SEQ ID No X consists of the sequence SEQ ID No 3 to SEQ ID No 116. It is also recalled that the aptamers having sequence SEQ ID No 3 to SEQ ID No 116 consist of aptamers of formula (I-3) in which the sequences SEQ ID No 1 and SEQ ID No 2 are absent.

Without wishing to be bound by any theory, the applicant thinks that the nucleic acid having sequence SEQ ID No X is an essential characteristic of an aptamer of formula (I), the nucleic acid having sequence SEQ ID No X conferring on the aptamer of formula (I) the ability to bind selectively to factor H. This may be deduced in particular from the fact that all of the nucleic acids contained in the starting nucleic acid mixture, or starting nucleic acid collection, used for selecting the nucleic aptamers of the invention, have in common the sequences SEQ ID No 1 and SEQ ID No 2 although it is shown in the examples that said starting nucleic acid mixture, collectively, does not bind to factor H.

As is illustrated in example 6, the nucleic aptamers according to the invention which consist exclusively of the sequence SEQ ID No X are highly capable of binding factor H, in particular human factor H. The results of example 6 show that the presence of a sequence SEQ ID No X in the sequence of a nucleic aptamer is sufficient to confer on said nucleic aptamer the ability to bind to factor H, in particular to human factor H. It is thus shown that a variety of aptamers comprising only a part of the sequence SEQ ID No X of an aptamer according to the invention retain a good ability to bind to factor H, in particular to human factor H.

It is shown that a nucleic aptamer comprising all or part of the sequence ranging from the nucleotide in position 28 up to the nucleotide in position 58 of the MaptH1.1 aptamer having sequence SEQ ID No 144 binds with good affinity to factor H, in particular to human factor H. It is specified that the sequence ranging from the nucleotide in position 28 up to the nucleotide in position 58 of the MaptH1.1 aptamer having sequence SEQ ID No 144 is referenced as the sequence SEQ ID No 30 in the present description.

More specifically, it is shown that a variety of nucleic aptamers derived from the MaptH1.1 parent nucleic aptamer having sequence SEQ ID No 144, which aptamers comprise only a part of the sequence SEQ ID No 30 (which is the sequence "SEQ ID No X" of the aptamer having sequence SEQ ID No 144), bind to factor H, and in particular to human factor H.

It is shown that the sequence ranging from the nucleotide in position 13 up to the nucleotide in position 48 of the MaptH1.1 nucleic aptamer having sequence SEQ ID No 144, i.e. a sequence only 36 nucleotides in length, confers on a nucleic acid which contains this sequence the ability to bind to factor H, in particular to human factor H. This is illustrated in example 6 by the factor H-binding capacity of the MaptH1.1 N13-48 (SEQ ID No 239), MaptH1.1 N19-58 (SEQ ID No 240), MaptH1.1 N19-53 (SEQ ID No 241), MaptH1.1 N19-48 (SEQ ID No 242) and MaptH1.1 N22-45 (SEQ ID No 243) nucleic aptamers.

Thus, the present invention also relates to a nucleic aptamer which binds to factor H, said nucleic aptamer comprising the sequence SEQ ID No 243.

In particular, the present invention relates to a nucleic aptamer of formula (III) below:

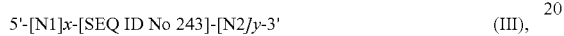

5'-[N1]x-[SEQ ID No 243]-[N2]y-3'     (III), in which:
"x" is an integer equal to 0 or 1, and
"y" is an integer equal to 0 or 1,
N1 is a nucleic acid having a length of from 1 to 100 nucleotides, and
N2 is a nucleic acid having a length of from 1 to 100 nucleotides.

For the purposes of the invention, a nucleic acid having a length of from 1 to 100 nucleotides encompasses the nucleic acids having a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 nucleotides.

In certain embodiments of a nucleic aptamer of formula (III), x and y are both equal to 1 and N1 and N2 are both present.

In certain embodiments of a nucleic aptamer of formula (III), x is equal to 0 and N1 is therefore absent.

In certain embodiments of a nucleic aptamer of formula (III), y is equal to 0 and N2 is therefore absent.

In certain embodiments of a nucleic aptamer of formula (III), x and y are both equal to 0 and N1 and N2 are both absent.

In certain embodiments of a nucleic aptamer of formula (III), N1, when it is present (when x is equal to 1), is a nucleic acid having a length ranging from 3 to 8 nucleotides, which encompasses a nucleic acid having a length of 3, 4, 5, 6, 7 or 8 nucleotides.

In certain embodiments of a nucleic aptamer of formula (III), N2, when it is present (when y is equal to 1), is a nucleic acid having a length ranging from 3 to 13 nucleotides, which encompasses a nucleic acid having a length of 3, 4, 5, 6, 7, 8, 9, 10, 12 or 13 nucleotides.

In certain embodiments of a nucleic aptamer of formula (III), x and y are both equal to 1, N1 is a nucleic acid 8 nucleotides in length and N2 is a nucleic acid 3 nucleotides in length, as for the MaptH1.1 N13-48 nucleic aptamer having sequence SEQ ID No 239.

In certain embodiments of a nucleic aptamer of formula (III), x and y are both equal to 1, N1 is a nucleic acid 3 nucleotides in length and N2 is a nucleic acid 13 nucleotides in length, as for the MaptH1.1 N19-58 nucleic aptamer having sequence SEQ ID No 240.

In certain embodiments of a nucleic aptamer of formula (III), x and y are both equal to 1, N1 is a nucleic acid 3 nucleotides in length and N2 is a nucleic acid 8 nucleotides in length, as for the MaptH1.1 N19-53 nucleic aptamer having sequence SEQ ID No 241.

In certain embodiments of a nucleic aptamer of formula (III), x and y are both equal to 1, N1 is a nucleic acid 3 nucleotides in length and N2 is a nucleic acid 3 nucleotides in length, as for the MaptH1.1 N19-48 nucleic aptamer having sequence SEQ ID No 242.

The present invention encompasses the nucleic aptamers which bind to factor H which are obtained according to the general method comprising the following steps:
a) providing a mixture, or collection, of nucleic acids,
b) bringing the mixture of nucleic acids provided in step a), or the mixture of nucleic acids provided in step d) when step b) is repeated, into contact with a purified factor H, under conditions which allow the formation of complexes between (i) nucleic acids of said mixture and (ii) the purified factor H,
c) performing a separation between (i) the nucleic acid(s) which has (have) formed complexes with the factor H and (ii) the nucleic acids which have not formed complexes with the factor H, and recovering the nucleic acid(s) which has (have) formed complexes with the factor H,
d) amplifying the nucleic acids which have formed complexes with the factor H, so as to obtain a mixture, or collection, of nucleic acids which bind to factor H,
e) repeating steps b) to d) a sufficient number of times to obtain a collection of nucleic acids which have the desired factor H-binding capacity, and
f) collecting the nucleic acid(s) which bind(s) to factor H, obtained in the last occurrence of step e).

In advantageous embodiments, said method comprises, between two successive repeats of steps b) to d), at least one step of counterselection by elimination of those of the nucleic acids amplified in the step d) lastly carried out, which bind to constituents of a serum free of factor H, in particular of a serum free of human factor H.

In advantageous embodiments of the method, the amount of anti-FH nucleic aptamers used in step b) is varied, which includes the fact that the anti-FH aptamer/factor H quantitative ratio is varied in two distinct occurrences of implementation of step b).

In advantageous embodiments, the amount of purified factor H used in step b) is varied, which includes the fact that the anti-FH aptamer/factor H quantitative ratio is varied in two distinct occurrences of implementation of step b).

Other advantageous embodiments of a method for obtaining anti-FH nucleic aptamers according to the invention are explained in detail later in the description, including in the examples.

Various specific embodiments above, which make it possible to adjust the factor H-binding characteristics of said nucleic aptamers, are explained in detail later in the present description.

In certain embodiments, the nucleic aptamers of the invention bind to a factor H chosen from a plasma factor H, a recombinant factor H and a transgenic factor H.

In certain embodiments, the nucleic aptamers of the invention bind specifically to a factor H chosen from human factor H and a non-human factor H.

In preferred embodiments, the nucleic aptamers of the invention consist of deoxyribonucleotide aptamers, also called DNA aptamers.

As will be described later, the anti-FH nucleic aptamers according to the invention may be used successfully for the manufacture of affinity chromatography supports, which are of use for separating factor H from the other proteins possibly present in a sample.

For the production of affinity chromatography supports in particular, the anti-FH nucleic aptamers of the invention are preferentially included in a chemical structure, also called "compound" in the present description, which comprises in particular a spacer means and, where appropriate, a means for immobilizing the aptamer on a solid support.

In certain embodiments, the nucleic aptamer is included in the structure of a compound of formula (II) below:

[IMM]x-[SPAC]y-[APT]    (II), in which:
[IMM] signifies a compound for immobilization on a support,
[SPAC] signifies a spacer chain,
[APT] signifies an anti-FH aptamer as defined in the present description, which encompasses the aptamers of formula (I),
x is an integer equal to 0 or 1, and
y is an integer equal to 0 or 1.

The invention encompasses (i) the compounds of formula (II) above for which x=0 and y=1 and also (ii) the compounds of formula (II) above for which x=1 and y=0.

In certain embodiments of the compound of formula (II), [APT] consists of a deoxyribonucleic acid of which the sequence is chosen from the sequences SEQ ID No 3 to SEQ ID No 116, the sequences SEQ ID No 117 to 232 and the sequences SEQ ID No 239 to 243.

The "spacer chain" denoted [SPAC] in the compound of formula (II) may be of any known type. The function of said spacer chain is to physically distance the nucleic acid from the surface of the solid support on which said compound may be immobilized and to enable a relative mobility of the nucleic acid with respect to the surface of the solid support on which it may be immobilized. The spacer chain limits or prevents steric hindrances, due to the solid support being too close to the nucleic acid, from hampering the binding events between said nucleic acid and coagulation protein molecules which may be brought into contact therewith. In the compound of formula (II), the spacer chain is preferentially bonded to the 5' end or to the 3' end of the aptamer nucleic acid.

Advantageously, the spacer chain is bonded both to one end of the aptamer and to the solid support. This construction with spacer has the advantage of not directly immobilizing the aptamer on the solid support. Preferably, the spacer chain is a nonspecific oligonucleotide or polyethylene glycol (PEG) or another hydrophilic hydrocarbon-based chain. When the spacer chain consists of a nonspecific oligonucleotide, said oligonucleotide advantageously comprises at least 5 nucleotides in length, preferably between 5 and 15 nucleotides in length.

In the embodiments of a compound of formula (II) in which the spacer chain consists of a polyethylene glycol, said spacer chain encompasses a polyethylene glycol of PEG(C18) type, sold, for example, by the company Sigma Aldrich.

The purification of factor H can be carried out both with compounds of formula (II) comprising a spacer chain [SPAC] and with compounds of formula (II) not possessing a spacer chain [SPAC].

In order to immobilize the aptamer on the spacer chain, the nucleic acid may be chemically modified with various chemical groups such as groups for covalently immobilizing said nucleic acid, such as thiols, amines or any other group capable of reacting with chemical groups present on the solid support.

In the compound of formula (II), the [IMM] compound consists of a compound chosen from (i) a compound capable of forming one or more covalent bond(s) with the solid support material and (ii) a compound capable of binding specifically on the solid support by means of weak noncovalent bonds, including hydrogen bonds, electrostatic forces or Van der Waals forces.

In certain cases, the [IMM] compound, because it consists of a chain of atoms linked to one another via covalent bonds, may behave like a spacer chain. However, by definition, an [IMM] compound can never signify a [SPAC] chain in a compound of formula (II) according to the invention. In other words, in a compound of formula (II), the [SPAC] chain, when it is present, cannot be bonded directly to the chromatography support, whether via covalent bonds or weak noncovalent bonds.

The first type of [IMM] compound encompasses bifunctional coupling agents, for instance glutaraldehyde, STAB or else SMCC.

The STAB compound is described, for example, by G T. Hermanson (1996, Bioconjugate techniques, San Diego: Académie Press, pp 239-242). The STAB compound comprises two reactive groups, respectively an iodoacetate group and a sulfo-NHS ester group, these groups reacting respectively on amino and sulfhydryl groups.

The SMCC compound is described, for example, by M. K. Samoszuk et al. (1989, Antibody, Immunoconjugates Radiopharm., 2(1): 37-46). The SMCC compound comprises two reactive groups, respectively a sulfo-NHS ester group and a maleimide group, which reactive respectively with an amino group and a sulfhydryl group.

The second type of [IMM] compound encompasses biotin, which is capable of specifically, noncovalently binding to avidin or streptavidin molecules present on the solid support. The examples illustrate a method for obtaining a support for detecting factor H, by immobilization of nucleic aptamers coupled to biotin on a support onto which streptavidin has been chemically grafted. In these embodiments, [IMM] consists of the biotin molecule.

According to another alternative, the [IMM] compound consists of a reactive amine group. Said reactive amine group is bonded to [SPAC] when [SPAC] is present. Said reactive amine group is bonded to [APT] when [SPAC] is absent. The examples also illustrate a method for obtaining an affinity support for purifying factor H, by immobilization of nucleic aptamers comprising a reactive amine group on [SPAC], which have been immobilized by chemical grafting onto a solid support comprising activated carboxyl groups, and more specifically carboxyl groups activated by NHS.

Once immobilized on the solid support via the spacer, the anti-FH aptamer is advantageously modified at its free end (end not bonded to the spacer) by virtue of, and without being limited thereto, a chemically modified nucleotide (such as 2'-o-methyl or 2'-fluoropyrimidine, 2'-ribopurine, phosphoramidite), an inverted nucleotide or a chemical group (PEG, polycations, cholesterol). These modifications make it possible to protect the anti-FH aptamer against enzymatic degradations.

The solid support may be an affinity chromatography column composed of a gel derived from agarose or cellulose or of a synthetic gel such as an acrylamide, methacrylate or polystyrene derivative, a chip such as a chip suitable for surface plasmon resonance, a membrane such as a polyamide, polyacrylonitrile or polyester membrane, or a magnetic or paramagnetic bead.

The present invention also relates to a complex between: (a) a nucleic aptamer chosen from a nucleic acid of formula (I) and a compound of formula (II), and (b) factor H.

A subject of the present invention is also a support for immobilizing factor H, characterized in that it comprises a solid support material onto which is grafted a plurality of molecules each consisting of, or each comprising, a nucleic aptamer, said molecules being chosen from (a) a nucleic acid of formula (I) and (b) a compound of formula (II).

The above support may be used practically in all applications for which it is sought to immobilize factor H, which encompasses applications for the purposes of purifying factor H and applications for the purpose of detecting factor H.

The production of supports on which are immobilized nucleic aptamers of the invention which bind specifically to factor H is widely illustrated in the examples, in which the aptamers of the invention are used in particular as capture agents, which can be used for purifying or detecting factor H, for example human factor H, in samples.

The present invention therefore also relates to a method for immobilizing factor H on a support, comprising a step during which a sample comprising factor H is brought into contact with a solid support on which a substance chosen from a nucleic acid of formula (I) and a compound of formula (II) has been previously immobilized. Said method may comprise, depending on the technical objectives pursued, an additional step of recovering the immobilized factor H molecules complexed with the nucleic acid molecules of formula (I). The additional step of recovering the factor H preferentially consists of a step of bringing the complexes of factor H with the nucleic acids of formula (I) into contact with a metal-cation-chelating agent, such as EDTA.

For carrying out methods for purifying proteins by affinity chromatography using solid supports on which the aptamers of interest are immobilized, those skilled in the art may refer to the studies described by Romig et al. (1999, J Chomatogr B Biomed Sci ApI, Vol. 731 (2): 275-284).

Generally, the solid supports on which the aptamers of the invention may be immobilized encompass any type of support having the structure and the composition commonly found for supports for a filter, a silicon support for chips, membranes, etc. The solid supports encompass in particular resins, resins for an affinity chromatography column, polymer beads, magnetic beads, etc. The solid supports also encompass in particular materials based on glass or metal, such as steel, gold, silver, aluminum or copper, silicon, glass and ceramic. The solid supports also encompass in particular polymer materials, such as a polyethylene, a polypropylene, a polyamide, a polyvinylidene fluoride, and combinations thereof.

The solid support may be coated with a material which facilitates the attachment, the binding, the formation of complexes, the immobilization or the interaction with the aptamers. In certain embodiments, the solid support is a glass strip, the surface of which is coated with a layer of gold, with a layer having undergone a treatment by carboxymethylation, with a layer of dextran, of collagen, of avidin, of streptavidin, etc. In this way, the aptamers according to the invention may be immobilized on the solid support by means of an attachment coating, such as, for example, described above, either by chemical reaction with the creation of covalent bonds, or by association via noncovalent bonds such as hydrogen bonds, electrostatic forces, Van der Waals forces, etc.

The examples describe embodiments of solid supports on which the aptamers of the invention are immobilized via noncovalent bonds. In the examples, solid supports consisting of a glass strip coated with a layer of streptavidin molecules, and aptamers of the invention conjugated to a biotin molecule, which are immobilized on the support via noncovalent biotin/streptavidin association, are in particular described.

In the examples, solid supports consisting of a polystyrene material coated with a layer of streptavidin molecules, and aptamers of the invention conjugated to a biotin molecule, which are immobilized on the support via noncovalent biotin/streptavidin association, are also described.

In certain embodiments, the aptamers of the invention may be immobilized on a solid support suitable for affinity chromatography, electrochromatography and capillary electrophoresis, as described, for example, by Ravelet et al. (2006, J Chromatogr A, Vol. 1 17(1): 1-10), Connor et al. (2006, J Chromatogr A, Vol. 1 1 1 (2): 115-119), Cho et al. (2004, Electrophoresis, Vol. 25 (21-22): 3730-3739) or alternatively Zhao et al. (2008, Anal Chem, Vol. 80(10): 3915-3920).

An aptamer of formula (I) which binds specifically to factor H, or a compound of formula (II), may be also advantageously used as an agent for capturing factor H, in detection or diagnosis methods and devices.

According to yet another aspect, the present invention also relates to a method for detecting the presence of factor H in a sample, comprising the following steps:
  a) bringing (i) a nucleic acid of formula (I), or a compound of formula (II), or a solid support on which a plurality of molecules of said nucleic acid or of said compound is immobilized, into contact with (ii) said sample; and
  b) detecting the formation of complexes between (i) said nucleic acid of formula (I), or said compound of formula (II), or said support, and (ii) the factor H.

For carrying out a detection method according to the invention, the solid support used may be a solid support chosen from the solid supports previously described in relation to the method for purifying factor H.

For carrying out a method for detecting factor H or for producing a device for detecting factor H, those skilled in the art may refer in particular to the techniques described in European patent application no EP 1 972 693, PCT application no WO 2008/038696, PCT application no WO 2008/025830, or alternatively PCT application no WO 2007/0322359.

In certain embodiments, step b) of detecting the formation of complexes between (i) said nucleic acid or said solid support and (ii) the factor H may be carried out by measuring the surface plasmon resonance signal, as is described in the examples.

In certain other embodiments, step b) of detecting the formation of complexes between (i) said nucleic acid or said solid support and (ii) the factor H may be carried out by bringing said possibly formed complexes into contact with a ligand specific for factor H, said ligand being detectable. For example, use may be made, as detectable factor H ligand, of anti-factor H monoclonal or polyclonal antibodies labeled with an enzyme, in the case in point horseradish peroxydase, as is conventionally used in ELISA assays. As factor H-specific antibodies, use may be particularly made of anti-factor H polyclonal antibodies such as those sold by the company Enzo Life Sciences (Lyon, France) or else anti-factor H monoclonal antibodies such as those sold by the company Abbiotec.

Surprisingly, it is shown according to the invention that it is possible to fabricate an affinity support as defined in the present description by using, as anti-FH nucleic aptamers, DNA aptamers which are nevertheless considered in the prior art to be nucleic acid ligands that are not easy to use, and the specificity of which for the target protein is lower than the specificity of the RNA molecule of corresponding sequence.

In particular, it is accepted in the prior art that DNA ligands have less flexibility that the corresponding RNA and that, consequently, they are less able than RNA ligands to undergo conformational changes. It is recalled that, when a nucleic aptamer binds to the target protein, a conformational change occurs. It has also been described that the faster the conformational change of the nucleic aptamer, the higher the affinity of said nucleic aptamer for the target protein (Michaud et al., 2003, Anal Chem, Vol. 76: 1015-1020; Brumbt et al., 2005, Anal Chem, Vol. 77: 1993-1998).

Thus, in certain embodiments of an affinity support according to the invention, the anti-FH aptamers consist of DNA aptamers.

Consequently, in certain embodiments of an affinity support according to the invention, said immobilized nucleic acids, where appropriate included in the structure of a compound of formula (I), consist of deoxyribonucleic acids.

In certain other embodiments of an affinity support according to the invention, a first part of said nucleic acids consists of deoxyribonucleic acids and the remaining part consists of ribonucleic acids.

Another advantage of the nucleic aptamers relates to the ease with which they can be produced, compared with the difficulties in synthesizing RNA aptamers, and also their cost price which is significantly lower than the cost price of an RNA aptamer.

These specific embodiments are illustrated in the examples. A subject of the present invention is also an affinity chromatography device for purifying factor H, comprising a container in which an appropriate amount of an affinity support as defined in the present description is placed.

Varied forms of containers for chromatography supports are known in the prior art and are encompassed by the meaning of the term "container" above.

The important characteristics of such a container encompass the presence of a means for feeding the affinity chromatography device with starting sample and of a means for discharging the liquid after it has been brought into contact with the affinity support.

The present invention also relates to a method for purifying factor H, comprising the following steps:
  a) bringing a sample containing factor H into contact with an affinity support as defined above, in order to form complexes between (i) the nucleic aptamers immobilized on said affinity support and (ii) said factor H,
  b) releasing the factor H from the complexes formed in step a), and
  c) recovering the factor H in purified form.

The starting samples from which the factor H is purified with an affinity support according to the invention encompass any type of liquid solution in which factor H is in suspension or is dissolved. Specific embodiments of such samples, in particular in relation to the purification method described hereinafter, will be subsequently defined in the present description.

In certain preferred embodiments, said sample contains human factor H. Advantageously, in these embodiments, the sample containing human factor H consists of a liquid sample which contains said protein of interest, including a liquid sample comprising said factor H and which may also contain molecules of factor H which is a homolog of a non-human mammal. In certain embodiments of the purification method above, said sample consists of a biological solution, such as a body fluid, a cell, ground cell material, a tissue, ground tissue material, an organ or a whole organism.

In certain embodiments of the purification method above, said sample consists of a liquid biological solution originating from an animal, such as blood, a blood derivative, milk from a mammal or a derivative of the milk from a mammal.

Said sample may consist of plasma, of plasma cryoprecipitate, of clarified milk, or derivatives thereof.

In particularly preferred embodiments of the purification method above, said sample originates from an animal which is transgenic for human factor H.

Advantageously, the solution is milk from a mammal or a derivative of the milk from a mammal which is transgenic for said human protein of interest. For the purposes of the invention, the transgenic animals encompass (i) non-human mammals such as cows, goats, rabbits, pigs, monkeys, rats or mice, (ii) birds or else (iii) insects such as mosquitoes, flies or silkworms. In certain preferred embodiments, the animal which is transgenic for the human protein of interest is a non-human transgenic mammal, entirely preferably a doe rabbit which is transgenic for said human protein of interest. Advantageously, the transgenic mammal produces said recombinant human protein of interest in its mammary glands, owing to the insertion, into its genome, of an expression cassette comprising a nucleic acid encoding said protein of interest, which is placed under the control of a specific promoter enabling the expression of the transgenic protein in the milk of said transgenic mammal.

A method for producing human factor H in the milk of a transgenic animal may comprise the following steps: a DNA molecule comprising a gene encoding human factor H, said gene being under the control of a promoter of a protein that is naturally secreted in milk (such as the casein promoter, the beta-casein promoter, the lactalbumin promoter, the beta-lactoglobulin promoter or the WAP promoter), is integrated into an embryo of a non-human mammal. The embryo is then placed in a mammalian female of the same species. Once the mammal derived from the embryo is sufficiently developed, lactation of the mammal is induced, and then the milk is collected. The milk then contains the recombinant human protein of interest. An example of a method for preparing protein in the milk of a mammalian female other than a human being is given in document EP 0 527 063, the teaching of which may be reproduced for producing the protein of the invention. A plasmid containing the WAP (Whey Acidic Protein) promoter is produced by introducing a sequence comprising the promoter of the WAP gene, this plasmid being prepared so as to be able to receive a foreign gene placed under the control of the WAP promoter. The plasmid containing the promoter and the gene encoding the protein of the invention are used to obtain transgenic doe rabbits by microinjection into the male pronucleus of doe rabbit embryos. The embryos are then transferred into the oviduct of hormonally prepared females. The presence of the transgenes is revealed by the Southern technique using the DNA extracted from the young transgenic rabbits obtained. The concentrations in the milk of the animals are evaluated by means of specific radioimmunological tests.

Other documents describe methods for preparing proteins in the milk of a mammalian female other than a human being. Mention may be made, without being limited thereto, of documents U.S. Pat. No. 7,045,676 (transgenic mouse) and EP 1 739 170 (production of von Willebrand factor in a transgenic mammal).

The purification method of the invention is also perfectly suitable for obtaining human factor H purified from a human blood plasma sample, or from a human blood plasma fraction, for example the cryoprecipitated fraction of human blood plasma.

In certain embodiments of the purification method above, the factor H is human factor H.

In certain embodiments of the purification method above, the sample comprises at least one non-human factor H.

In certain embodiments of the purification method above, the starting sample may consist of the crude material, either the human blood plasma sample, or a fraction thereof, or the body fluid of a non-human mammal which is transgenic for factor H, and which contains the factor H to be purified. The body fluids of a transgenic non-human mammal encompass the milk or a fraction of the milk, for example a defatted fraction of the milk or alternatively a fraction with a low casein micelle content.

However, the embodiment above is not the preferred embodiment of the purification process of the invention, in particular because of the risk of clogging of the affinity support by the numerous proteins present in the starting crude sample. In preferred embodiments, said starting sample consists of a liquid solution containing the factor H in suspension in said solution, said liquid solution consisting of an intermediate product generated during a multistep method for purifying factor H.

By way of illustration, for a method of purifying factor H from a body fluid of a non-human mammal which is transgenic for said protein, the starting sample may consist of an eluate from a hydrophobic interaction chromatography step, such as a chromatography step in which a chromatographic support of the MEP HyperCel® type is used.

Likewise, for a method for purifying factor H from human plasma, the starting sample may consist of a plasma fraction already enriched with factor H.

By way of illustration, use may be made, as starting material, of the supernatant of a cryoprecipitate of blood plasma optionally mixed with a plasma fraction not retained on an anion exchange chromatography of the DEAE-Sephadex type. Use may also be made, as starting material, of the supernatant of an ethanolic precipitation of blood plasma. Likewise by way of illustration, use may be made, as starting material, of the eluate of an affinity chromatography of a plasma sample on a support, in particular an agarose support, onto which is grafted heparin or heparin derivatives or mimetics, which have the property of retaining factor H and antithrombin III (ATIII). It is specified that the factor H and the ATIII are eluted separately, which makes it possible to obtain an eluate fraction enriched with factor H which may be used as starting product in a method for purifying factor H comprising a step of forming complexes between said factor H and anti-FH aptamers according to the invention.

Generally, the conditions for using the affinity support in order to carry out the purification method of the invention are very similar to the conventional conditions for using a conventional chromatography support, for example of the immunoaffinity support type on which ligand antibodies are immobilized. A person skilled in the art may, for example, refer to the book by Bailon et al. (Pascal Bailon, George K. Ehrlich, Wen-Jian Fung and Wolfgang Berthold, An Overview of Affinity Chromatography, Humana Press, 2000).

However, as will be explained in detail in the rest of the description, the conditions of elution step c), during which step the factor H is released from the complexes formed in step a), are very advantageous, for the purification of factor H.

In step a), an appropriate volume of the sample to be purified is brought into contact with the affinity support. Complexes are formed between (i) the anti-FH aptamers immobilized on said affinity support and (ii) the factor H contained in the sample to be purified.

In certain embodiments, the characteristics of the method for obtaining the aptamers are adjusted such that the conditions for binding of the anti-FH aptamers to the factor H are promoted in the presence of magnesium. Thus, in certain embodiments of step a), a buffer solution which comprises magnesium, preferentially in the form of a magnesium salt, preferably a magnesium chloride ($MgCl_2$), is used.

The affinity for factor H of a chromatography support on which an anti-FH aptamer according to the invention is immobilized may be substantially increased when use is made, in step a), of a buffer solution comprising magnesium chloride, for example a buffer solution of 50 mM Tris-HCl, at pH 7.5, 150 mM NaCl and 10 mM $MgCl_2$, in comparison with an identical buffer solution but which is free of magnesium chloride.

Thus, in certain embodiments of step a) of the purification method, a buffer solution comprising a final $MgCl_2$ concentration of at least 1 mM is used. In step a), a buffer solution comprising a final $MgCl_2$ concentration of at most 50 mM, which encompasses at most 20 mM, is advantageously used.

In preferred embodiments of the method, at the end of step a), and prior to step b), described in detail later, one or more steps of washing the affinity support are carried out so as to remove the substances which are not specifically retained, for example the substances simply adsorbed onto said support. A conventional washing buffer, well known to those skilled in the art, may be used.

However, in certain embodiments of the washing step(s), a washing buffer comprising NaCl, and/or ethylene glycol, and/or propylene glycol, and/or ethanol, may be used.

In certain embodiments, the use of a washing solution comprising NaCl does not lead to any deterioration in the specific binding of the target factor H to the immobilized anti-FH aptamers. It has been shown in particular that a final NaCl concentration of 3 M does not disrupt said specific binding.

Thus, in certain embodiments of the washing step(s) prior to step b), use is made of a washing solution having a final NaCl concentration of at least 0.5 M, which includes at least 1 M, 1.5 M, 2 M, 2.5 M and 3.0 M. The final NaCl concentration is advantageously at most 4 M.

It has also been shown that the capacity of the anti-FH aptamers of the invention to bind to the target factor H is not impaired when the complexes formed between the immobilized aptamers and said target factor H are subjected to an environment of high ionic strength, which is an entirely unexpected result. It is in fact recalled that it is common to have recourse to a buffer of high ionic strength as a buffer for eluting substances previously complexed to ligands immobilized on an affinity support, including an affinity support comprising immobilized aptamers.

In certain embodiments, one or more of the anti-FH aptamers according to the invention may possess specific and unexpected characteristics, regarding the absence of effect of a high ionic strength on their factor H-binding capacity.

In certain embodiments of the method, the use of a washing solution comprising an alkylene glycol does not lead to deterioration in the specific binding of the factor H to the immobilized anti-FH aptamers.

The use of a washing solution comprising ethylene glycol does not lead to deterioration in the specific binding of the factor H to the immobilized anti-FH aptamers.

Thus, in certain embodiments of the washing step(s) prior to step b), for example with some of the nucleic aptamers of the invention, use may be made of a washing solution having a final ethylene glycol concentration of at least 0.5 M, which includes at least 1 M, and 1.5 M. Advantageously, use is made of a washing solution having a final ethylene glycol concentration of at most 3 M.

Likewise, the use of a washing solution comprising propylene glycol may, with at least some nucleic aptamers of the invention, not lead to deterioration in the specific binding of the factor H to the immobilized anti-FH aptamers.

Thus, in certain embodiments of the washing step(s) prior to step b), it would be possible to have recourse to a washing solution having a final propylene glycol concentration of at least 10% (v/v), which includes at least 15%, 20%, 25%, 30%, 35%, 40%, 45% and 50%. Advantageously, use is made of a washing solution having a final propylene glycol concentration of at most 70% (v/v).

Likewise, with certain nucleic aptamers of the invention, the use of a washing solution comprising ethanol might not lead to a deterioration in the specific binding of the factor H to the immobilized anti-FH aptamers.

Thus, in certain embodiments of the washing step(s) prior to step b), it would be possible to use a washing solution having a final ethanol concentration of at least 1% (v/v), which includes at least 1.5%, 2.0%, 2.5%, 3.0%, 3.5%, 4.0%, 4.5%, 5.0%, 5.5%, 6.0%, 6.5%, 7.0%, 7.5%, 8.0%, 9.0%, 9.5% and 10.0%. Advantageously, in this case, a washing solution having a final ethanol concentration of at most 20.0% is used.

A washing buffer as defined above leads to drastic conditions for removing the substances which are not specifically retained on the aptamers, while at the same time preserving the specific binding of the factor H to the aptamers immobilized on the affinity support. It is recalled that such a technical advantage linked to the exclusive or virtually exclusive removal of the substances not specifically bound to the ligands immobilized on the affinity support cannot be easily realized with an affinity support on which antibodies are immobilized.

Step b) consists of a step of eluting the factor H having formed complexes with the anti-FH nucleic aptamers during step a). An expected specific advantage of the purification method above is the possibility of carrying out the elution step by bringing the complexes formed between (i) the anti-FH nucleic aptamers immobilized on said affinity support and (ii) the factor H into contact with a divalent-ion-chelating agent, such as EDTA.

This technical advantage, which is made possible by virtue of the characteristics of the affinity support of the invention, makes it possible to elute the factor H without requiring any recourse to the use of drastic elution conditions, that may denature, at least partially, the factor H. Said drastic conditions which are avoided encompass the use of an acidic pH for the elution step, which is commonly performed for the methods for purifying proteins on affinity supports that are known, and quite particularly on affinity supports comprising immobilized antibodies.

Thus, in certain embodiments of the purification method above, step b) is carried out by bringing the affinity support into contact with an elution buffer containing a divalent-ion-chelating agent, such as EDTA.

By way of illustration, the elution buffer may contain a final EDTA concentration of at least 1 mM and of at most 500 mM.

The expression "at least 1 mM of EDTA" encompasses at least 2 mM, 3 mM, 4 mM, 5 mM, 6 mM, 7 mM, 8 mM, 9 mM, 10 mM, 15 mM, 20 mM or at least 30 mM of EDTA.

In step c), the factor H is recovered in purified form by collecting the eluate liquid obtained at the end of step b).

At the end of step c), a purified liquid composition of the coagulation protein of interest is obtained. Said purified liquid composition can then be treated appropriately, according to any known technique for conditioning and storing proteins, including by direct bottling or bottling after dilution with a suitable solution, or else by lyophilization, preferentially under sterile and apyrogenic conditions, and then storage under appropriate conditions, at ambient temperature, at 4° C. or else at low temperature, depending on the type of conditioning selected.

As has already been mentioned previously in the present description, the affinity support of the invention may, with the successive cycles of use for purifying the factor H, experience a reduction in its absorption capacity, for example owing to the fact that the elution step c) does not make it possible to systematically release all of the molecules of coagulation protein, thereby reducing the number of free aptamer sites for the subsequent purification cycles.

As for all known chromatography supports, it is therefore necessary, at appropriate moments, to carry out a step of regenerating the affinity support, in order to release all of the molecules of factor H from said support, and to remove any substance that may be bound to the solid material of the affinity support, generally by nonspecific binding.

Thus, in certain embodiments, the purification method of the invention comprises an additional step d) of regenerating the affinity support by bringing said affinity support into contact with a regenerating solution.

Varied buffers for regenerating chromatography supports, in particular affinity chromatography supports, are well known to those skilled in the art, and can be used in step d) of the method. Those skilled in the art may refer, for example, to the handbook by Mohr et al. (Affinity Chromatography: Practical and Theoretical Aspects, Peter Mohr, Klaus Pommerening, Edition: illustrated, CRC Press, 1985).

By way of illustration, step d) of regenerating the affinity support may be carried out by bringing said support into contact with a buffer solution of 20 mM Tris, 5% polyethylene glycol and 1 M NaCl, for example at pH 7.5.

Without wishing to be bound by any theory, the applicant thinks that the purification method above makes it possible to obtain a target factor H at a very high degree of purity, optionally at a degree of purity greater than 99.95% by weight, relative to the total weight of the proteins contained in the purified final product.

Another advantage of the purification method above, in particular in the embodiments in which the starting sample consists of a sample comprising factor H in recombinant form as a mixture with proteins naturally produced by the non-human transgenic mammal, is that the final composition comprising the recombinant human protein of interest at a high degree of purity is substantially free of proteins originating from said transgenic mammal, and in particular substantially free of proteins of said mammal which are homologous to the recombinant human factor H.

The present invention also relates to a nucleic aptamer which binds specifically to factor H, of which the ability to bind to the target factor H is not impaired by exposure to a drastic environment, including an environment which causes the inactivation or the physical destruction of proteins, or else the inactivation or destruction of micro-organisms, such as viruses, bacteria, fungi or algae. Advantageously, the invention relates to a nucleic aptamer which binds selectively to factor H and of which the capacity to bind to factor H is not impaired by an environment capable of inactivating, including destroying, viruses, such as a highly concentrated NaOH solution. A highly concentrated NaOH solution encompasses an NaOH solution greater than 0.05 M. In this specific context, an NaOH solution greater than 0.05 M encompasses NaOH solutions greater than 0.1 M, 0.2 M, 0.3 M and 0.4 M. It may for example be an NaOH solution of approximately 0.5 M.

These properties may advantageously be used for very efficiently washing an affinity support on which a nucleic aptamer according to the invention is immobilized, thereby making it possible to obtain better removal of the contaminants nonspecifically bound to the column. The improvement in the washing efficiency makes it possible to increase the purity of the factor H that it is sought to purify.

In particular, these properties may be advantageously used for sanitizing an affinity support, i.e. carrying out a step for inactivating or for destroying micro-organisms, in particular viruses, capable of contaminating said affinity support, without substantially impairing the capacity of said affinity support to selectively bind the target factor H. These properties are essential for affinity supports which are used in methods for purifying factor H intended for use in the human or veterinary medical field.

As has been previously described in the present description and is also illustrated in the examples, the complexes formed between the nucleic aptamers of the invention and the factor H can be dissociated by bringing said complexes into contact with a solution comprising a divalent-ion-chelating agent, for example EDTA. Thus, according to another of their characteristics, the nucleic aptamers of the invention consist of nucleic aptamers which allow the formation of complexes with the target factor H, it being possible for said complexes to be dissociated, with release of the target factor H, by bringing said complexes into contact with a medium comprising a divalent-ion-chelating agent, for example EDTA.

As already previously specified, a complex between a nucleic aptamer of the invention and factor H may be dissociated by bringing said complex into contact with a medium, including a buffer solution, comprising a final EDTA concentration of at least 1 mM and of at most 500 mM.

A subject of the present invention is also a purified composition of recombinant human factor H comprising at least 99.9% by weight of recombinant human factor H and which is substantially free of non-human proteins. The present invention also relates to a purified composition of recombinant human factor H comprising at least 99.9% by weight of said recombinant human factor H and at most 0.1% by weight of non-human proteins, the percentages by weight being expressed relative to the total weight of proteins of said purified composition.

In the purified composition above, "at least 99.9%" encompasses at least 99.91%, 99.92%, 99.93%, 99.94%, 99.95%, 99.96%, 99.97%, 99.98% and 99.99%.

In the purified composition above, "at most 0.1%" encompasses at most 0.09%, 0.08%, 0.07%, 0.06%, 0.05%, 0.04%, 0.03%, 0.02% and 0.01%.

The present invention also relates to a purified composition as defined above, which can be used as medicament.

The invention also relates to a pharmaceutical composition comprising a purified composition of recombinant human factor H as defined above, in combination with one or more pharmaceutically acceptable excipients.

The invention also relates to a purified composition as defined above, for treating disorders associated with a factor H deficiency.

The invention also relates to the use of a purified composition as defined above, for manufacturing a medicament for treating disorders associated with a factor H deficiency.

The disorders associated with a factor H deficiency encompass hemolytic uremic syndrome (HUS), including the typical form of HUS and the atypical form of HUS, and membranoproliferative glomerulonephritis type II.

Particular Embodiments of Anti-FH Affinity Supports

In specific embodiments of the invention, use is made of affinity supports which are prepared by chemical grafting of the anti-FH aptamers onto a solid support comprising activated carboxylic acid functions, under specific grafting conditions which both allow a high grafting yield and make it possible to maintain the integrity of the grafted anti-FH aptamers.

In these embodiments, an affinity support according to the invention is obtained according to a method for immobilizing anti-FH aptamers comprising at least one reactive amine function, by grafting onto a solid support exhibiting activated carboxylic acid functions, comprising a step of covalently coupling said nucleic acids onto said solid support at a pH below 5.

According to the invention, an anti-FH aptamer comprises a reactive amine function when said aptamer possesses an amine function accessible to the solvent and capable of reacting with an appropriate reactive group borne by another molecular entity. Such an amine function encompasses in particular primary amines.

Nucleic acids possessing a reactive amine function are well known in the prior art and are conventionally used for their chemical coupling to supports or to marker substances. Conventionally, they are nucleic acids which have been modified by the addition of an amine function at their 3' or at their 5' end. Most commonly, the amine function is added at the 5' end of the nucleic acid where its incorporation is easier as a final step of a method for synthesizing a polynucleotide. In certain embodiments, the reactive amine function and the 5' or 3' end of the nucleic acid are separated by a spacer chain.

According to the invention, an anti-FH aptamer may comprise a reactive amine function at its 3' or 5' end, which means that the reactive amine function is coupled to the nucleotide part of said nucleic acid.

According to other embodiments, an anti-FH aptamer may comprise a reactive amine function "on the side" of its 3' or 5' end, which means that said amine function is not coupled directly to the nucleotide part of said anti-FH aptamer, but is covalently bonded to a non-nucleotide part of said anti-FH aptamer, for example a non-nucleotide spacer chain which is inserted between said reactive amine function and said end of the nucleotide part of said anti-FH aptamer.

The term "activated carboxylic acid function" or "activated carboxylic acid group" is intended to mean a chemical function derived from the "carboxylic acid" function capable of reacting with a nucleophile. More specifically, the term "activated carboxylic acid function" is intended to mean a chemical function derived from the "carboxylic acid" function capable of reacting with a primary amine so as to form an amide bond. The "activated carboxylic acid" functions are well known to those skilled in the art and encompass acid chloride, mixed anhydride and ester functions.

In certain embodiments, the activated carboxylic acid functions are in the form of esters resulting from the reaction of said carboxylic acid functions with a compound chosen from the group consisting of 1-hydroxybenzotriazol (HOBt), HOAt, N-hydroxysuccinimide or one of their derivatives.

In one preferred embodiment, the carboxylic acid groups of the support have been activated by reaction with N-hydroxysuccinimide or one of its derivatives, such as N-hydroxysulfosuccinimide.

This means that the "activated carboxylic acid" groups of the solid support correspond to "N-succinimidyl ester" groups, also known as "succinimidyl ester" groups or "N-hydroxysuccinimide ester" groups, of formula (I) below where R represents the branching of the solid support to which the ester function is attached:

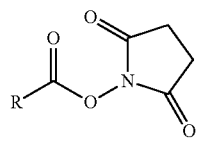

Activation with NHS or sulfo-NHS has the advantage of generating activated esters which are reactive with respect to primary amines but also sufficiently stable to allow the conditioning and the storage of the pre-activated support obtained.

Solid supports exhibiting "activated carboxylic acid" functions are well known in the prior art and many of them are commercially available. The solid supports may also be prepared according to methodologies well known to those skilled in the art, for example by reacting a support initially exhibiting carboxylic acid functions at its surface with a suitable chemical agent which enables the activation of the carboxylic acid functions with a view to the subsequent formation of an amide bond. Reference may, in particular, be made to the conventional methods for activating carboxylic acid functions used in peptide synthesis, in particular via the solid process. By way of illustration, the methodology of activation using a combination of EDC (1-ethyl-3-[3-dimethylaminopropyl]carbodiimide hydrochloride) and NHS, well known to those skilled in the art, may also be used, under the specific coupling conditions recommended by the invention.

The solid supports exhibiting "activated carboxylic acid" functions may be of any type. These supports encompass the supports conventionally used for chromatography, including silicon and agarose supports, and which have been treated in order to exhibit activated carboxylic acid groups at their surface. The pre-activated solid supports encompass gels of dextran, agarose, starch, cellulose-based derivatives, or else synthetic polymers such as polyamides, trisacryl, sephacryl, methacrylate derivatives, polystyrene derivatives and polyacrylamides, or else mineral supports such as silica supports (in particular porous glass supports) or alumina supports, on the surface of which activated carboxylic acid groups are present. Generally, the solid supports on which the nucleic ligands according to the invention may be immobilized encompass any type of support having the structure and the composition commonly found for supports for filters, membranes, etc. The solid supports encompass in particular resins, resins or gels for an affinity chromatography column, polymer beads, magnetic beads, paramagnetic beads, support materials for filtering membranes, etc. The solid supports also encompass in particular materials based on glass or metal, such as steel, gold, silver, aluminum or copper, silicon, glass and ceramic. The solid supports also encompass in particular polymer materials, such as a polyethylene, a polypropylene, a polyamide, a polyvinylidene fluoride, polyacrylamide derivatives, and combinations thereof.

In the particular embodiments for which the carboxylic acid functions of the solid support are activated with NHS, said solid support may be obtained by reacting a commercial gel exhibiting free carboxylic acid functions with N-hydroxysuccinimide (NHS), optionally in the presence of a carbodiimide such as 1-ethyl-3-(3-dimethylaminopropyl)carbodiimide (EDC).

Use may also be made of a commercial solid support pre-activated with NHS, such as, for example, an "NHS Activated Sepharose 4 fast flow" gel (GE) sold by the company General Electric Healthcare (United States), a "HiTrap™ NHS-activated" gel sold by the company General Electric Healthcare (United States) or else an "NHS-Activated Agarose" gel sold by the company Thermo Scientific Pierce.

The method for obtaining an affinity support which has been developed by the applicant has consisted in carrying out the reaction for coupling the anti-FH aptamers onto a support pre-activated with N-hydroxysuccinimide, under pH conditions below 5.

The success of this technical solution is entirely surprising since, at an acidic pH, those skilled in the art would normally have expected the coupling reaction not to take place at all, or at the very least to take place in such a low proportion that a very low grafting yield is obtained.

However, carrying out the step of coupling the anti-FH aptamers onto a support pre-activated with NHS, under pH conditions below 5, makes it possible to obtain a grafted support with a grafting yield of 100%, or very close to 100%.

Carrying out the coupling step at an acidic pH does not affect the functional integrity of the anti-FH aptamers, although the high sensitivity of nucleic acids to acidic pH conditions is well known by those skilled in the art. The anti-FH aptamers grafted onto the support retain their chemical and physical integrity, because their functionality is intact.

Furthermore, the method above results in the obtaining of affinity supports which possess a high density of grafted nucleic acids and consequently permits the availability of affinity supports which possess a high target factor H-capture capacity, and which can be used on an industrial scale.

The combined characteristics of high selectivity with respect to the target factor H and of high capacity for capture of said target factor H illustrate the compatibility of an affinity support obtained as described above with use in a step for purifying factor H on an industrial scale.

In these industrial applications, an additional advantage of an affinity support prepared as described above is its capacity to withstand treatments which comprise exposing the support to a strongly alkaline pH and/or to strongly polar compounds. Thus, the chromatographic properties of an affinity support according to the invention are not impaired by treatment with a solution having a final NaOH concentration of 0.5 M. It has also been shown that the chromatographic properties of an affinity support according to the invention are not impaired by treatment with a solution having a final propylene glycol concentration of 50% (vol/vol).

Consequently, an affinity support according to the invention is not impaired by drastic treatments of the type described above, which are in particular intended to remove the undesirable micro-organisms capable of contaminating the purified preparations of the target ligand, in particular bacteria, fungi and viruses.

In these particular embodiments, an affinity support for the selective binding of factor H may be prepared according to a method comprising the following steps:
  a) providing a solid support comprising activated carboxylic acid groups at its surface,
  b) providing an anti-FH nucleic aptamer or compound of formula (I) comprising at least one reactive amine function, and
  c) coupling said anti-FH nucleic aptamer, or said compound of formula (I), with the activated carboxylic acid groups present at the surface of said solid support under pH conditions below 5, it being understood that the order of steps a) and b) is unimportant.

It goes without saying that the coupling step c) makes it possible to create amide bonds between the solid support and the nucleic ligands, each amide bond resulting from the reaction between an activated carboxylic acid function of the support and a primary amine function present at the level of the nucleic ligand.

According to the invention, the coupling conditions at a pH below 5 encompass coupling conditions at a pH below 5, below 4.9, below 4.8, below 4.7, below 4.6, below 4.5, below 4.3.

In some embodiments, the pH of the coupling step is included in a range of from 3 to 5, which encompasses a pH of 3.0, a pH of 3.1, a pH of 3.2, a pH of 3.3, a pH of 3.4, a pH of 3.5, a pH of 3.6, a pH of 3.7, a pH of 3.8, a pH of 3.9, a pH of 4.0, a pH of 4.1, a pH of 4.2, a pH of 4.3, a pH of 4.4, a pH of 4.5, a pH of 4.6, a pH of 4.7, a pH of 4.8, a pH of 4.9 and a pH of 5.0.

Preferably, the pH of the coupling step is below 4.5. In certain embodiments, the pH of the coupling reaction is included in a range of from 3.5 to 4.5.

The coupling step may be carried out at a pH of approximately 4.2.

Preferably, the coupling is carried out in the presence of an aqueous buffered medium which has a pH below 5. The buffered medium may be prepared from weak acids and/or bases of any type, insofar as the weak acid(s) and base(s) used are not capable of reacting during the coupling reaction. As is illustrated in the examples, it may be an aqueous solution of sodium acetate.

The coupling step may be carried out, without distinction, at low temperature and at ambient temperature. Notably, carrying out the reaction at ambient temperature does not induce a decrease in the reaction yield. Similarly, carrying out the reaction at low temperature—typically at a temperature of 5° C.—does not induce a substantial decrease in the reaction rate.

Thus, in certain reaction modes, the coupling step is carried out at a temperature included in the range of from 0° C. to 50° C.

Preferably, the coupling step may be carried out at a temperature ranging from 0° C. to 35° C.

Practically, the coupling reaction may be carried out at ambient temperature, i.e. at a temperature ranging from 15° C. to 35° C., preferably at a temperature ranging from 15° C. to 25° C. Nevertheless, the coupling step may be carried out at low temperature, typically at a temperature ranging from 0° C. to 8° C., if the reagents involved—in particular the nucleic ligands—exhibit chemical groups which are sensitive, in particular to hydrolysis.

Since the coupling reaction is particularly fast, a satisfactory progression of the reaction is generally obtained after approximately one hour, or even after a few minutes. By using suitable techniques for monitoring kinetics, those skilled in the art will be able to determine the optimum duration of the reaction. The same is true for the reaction temperature.

Generally, as is illustrated in the examples, the coupling step may be carried out at a pH ranging from 3.5 to 4.5, at ambient temperature and for a period of approximately one hour.

Of course, those skilled in the art may, on the basis of the general conditions above, adjust the conditions of the coupling reaction in order to determine the appropriate optimum conditions in each precise case, on the basis of their general knowledge of chemistry. By way of illustration, those skilled in the art may readily foresee that, to obtain a given coupling yield, reducing the reaction temperature is liable to require an increase in the duration of the coupling step.

In certain embodiments of the immobilization method according to the invention, the coupling reaction may be finished by placing the pre-activated support/nucleic acids combination under alkaline pH conditions for a given period of time.

In these embodiments, the coupling step of the method of the invention itself comprises the following two steps:

c1) reacting said nucleic acid with the activated carboxylic acid groups present at the surface of said solid support, under pH conditions below 5, and c2) continuing the reaction for coupling of said nucleic acid with the activated carboxylic acid groups present at the surface of said solid support, under pH conditions above 7.5.

Advantageously, the final coupling phase at alkaline pH is carried out at a pH of at least 7.5, which encompasses pHs of at least 8 and of at least 8.5. The examples illustrate the implementation of step c2) at a pH of approximately 9.

Step c2) may be carried out at ambient temperature or at a low temperature. The term "low temperature" for the final step of the coupling reaction is intended to mean a temperature below 15° C., including a temperature below 14° C., 13° C., 12° C., 11° C., 10° C., 9° C., 8° C., 7° C., 6° C. or 5° C.

The duration of the final phase of the coupling step is variable. It is between a few minutes and a few hours. Generally, the duration of step c2) is less than 9 hours, which encompasses a duration of less than 8, 7, 6, 5, 4, 3, 2 and 1 hours. The duration of step c2) may be approximately 8 hours or approximately 3 hours, as is illustrated in the examples.

For said final phase of the coupling step, those skilled in the art may readily determine, on the basis of the above indications, the optimum conditions for combining pH, temperature and duration, on a case-by-case basis.

In advantageous embodiments, the coupling reaction is followed by a step of neutralizing d) or of blocking the activated carboxylic acid groups which have not reacted during the actual coupling step. By way of illustration, the blocking of the activated carboxylic acid functions which have not reacted may be carried out by incubation of the grafted support with a blocking solution comprising 0.5 M of ethanolamine and 0.5 M of NaCl at pH 8.3, or else with a blocking solution containing 0.1 M Tris-HCl at pH 8.5, as is recommended in particular by the manufacturer and described, moreover, in the examples. The duration of the neutralizing or blocking step is advantageously at least one hour at low temperature. It may be carried out, for example, for a period of 2 h30 at a temperature of 4° C., as described in the examples.

Lastly, the method according to the invention comprises, at the end of the coupling step c) and/or at the end of the blocking or neutralizing step d), one or more steps of washing e) said support under conventional conditions so as to obtain a ready-to-use affinity support. By way of illustration, the washing step(s) may be carried out with a buffer solution of 0.1 M Tris-HCl at a pH ranging from 8 to 9, or else with a buffer solution of 0.1 M acetate, 0.5 M NaCl at a pH ranging from 4 to 5, as is illustrated in the examples. In certain embodiments, a washing step comprises successively (i) washing with a buffer solution of 0.1 M Tris-HCl at a pH ranging from 8 to 9, followed by (ii) washing with a buffer solution of 0.1 M acetate, 0.5 M NaCl at a pH ranging from 4 to 5. Conventionally, a plurality of washing steps, for example three washing steps, are carried out, as is illustrated in the examples.

In the light of the preceding description, the method for immobilizing nucleic acids according to the invention may also be defined as a method comprising the following steps:

a) providing a solid support comprising activated carboxylic acid groups, preferably N-hydroxysuccinimide-activated carboxylic acid groups, at its surface, b) providing a nucleic acid comprising at least one primary amine function, c) coupling said nucleic acid with the activated carboxylic acid groups present at the surface of said solid support under pH conditions below 5, and d) blocking the coupling reaction.

The method for immobilizing nucleic acids according to the invention may also be defined as a method comprising the following steps:

a) providing a solid support comprising activated carboxylic acid groups, preferably N-hydroxysuccinimide-activated carboxylic acid groups, at its surface, b) providing a nucleic acid comprising at least one primary amine function, c) coupling said nucleic acid with the activated carboxylic acid groups present at the surface of said solid support under pH conditions below 5, d) blocking the coupling reaction, and e) carrying out one or more support washing steps.

As has already been previously specified, in certain embodiments, step c) itself comprises the following two steps:

c1) reacting said nucleic acid with the activated carboxylic acid groups, preferably N-hydroxysuccinimide-activated carboxylic acid groups, present at the surface of said solid support, under pH conditions below 5, and c2) continuing the reaction for coupling of said nucleic acid with the activated carboxylic acid groups present at the surface of said solid support, under pH conditions above 7.5.

Methods for Obtaining Anti-FH Aptamers

Generally, an anti-FH aptamer according to the invention may be obtained according to a method based on the general principles of the technique known as SELEX (Systematic Evolution of Ligands by Exponential Enrichment, which was initially described in particular in PCT application No WO 1991/019813). The SELEX method for selecting aptamers consists in bringing a protein into contact with a combinatorial library of DNA or RNA nucleic acids (generally $10^{15}$ molecules), the nucleic acids which do not bind to the target are removed, the nucleic acids which bind to the target are isolated and amplified by PCR. The method is repeated until the solution is sufficiently enriched with the nucleic acids having a good affinity for the protein of interest (Tuerk and Gold, "Systematic evolution of ligands by exponential enrichment: RNA ligands to bacteriophage T4 DNA polymerase" (1990) Science, 249(4968):505-10 and Ellington and Szostak, "In vitro selection of RNA molecules that bind specific ligands", (1990) Nature August 30; 346(6287):818-22). Other examples of the SELEX method are given in documents EP 0 786 469, EP 668 931, EP 1 695 978 and EP 1 493 825, the teachings of which may be reproduced in carrying out the method for selecting a nucleic aptamer used according to the invention. Certain variants of the SELEX method comprise steps of counterselection of aptamers previously selected by binding to the target protein of interest. The counterselection step(s) may consist of a step in which a collection of aptamers, which has been previously selected with the target protein of interest, is brought into contact with non-target molecules, so as to remove, from the starting aptamer collection, the aptamers which bind to the non-target molecules. The implementation of such a counterselection step, in a method for obtaining nucleic aptamers, is capable of increasing the specificity or the affinity of the aptamers selected at the end of the method.

A first method for obtaining an anti-FH aptamer may consist of a method comprising the following steps:

a) providing a mixture, or collection, of nucleic acids, b) bringing the mixture of nucleic acids provided in step a), or the mixture of nucleic acids provided in step d) when step b) is repeated, into contact with a purified factor H, under conditions which allow the formation of complexes between (i) nucleic acids of said mixture and (ii) the purified factor H, c) performing a separation between (i) the nucleic acid(s) which has (have) formed complexes with the factor H and (ii) the nucleic acids which have not formed complexes with the factor H, and recovering the nucleic acid(s) which has (have) formed complexes with the factor H, d) amplifying the nucleic acids which have formed complexes with the factor H, so as to obtain a mixture, or collection, of nucleic acids which bind to factor H, e) repeating steps b) to d) a sufficient number of times to obtain a collection of nucleic acids having the desired factor H-binding capacity, and f) collecting the nucleic acid(s) which bind(s) to factor H, obtained in the last occurrence of step e).

In certain embodiments, the characteristics of the method are adjusted so as to obtain anti-FH aptamers which bind selectively to native factor H and which do not bind to forms of factor H which have undergone degradation, for example proteolyzed forms of factor H. In these embodiments, use is made, in step b) of the method, of a composition of purified factor H comprising at least 70% by weight of nondegraded native factor H, which encompasses the compositions of purified factor H comprising at least 75%, 80%, 85%, 90% by weight of nondegraded native factor H, relative to the total weight of factor H (intact factor H and degraded factor H) contained in said factor H composition.

In some embodiments of the method, use is made of distinct compositions of purified factor H, in particular at least two distinct compositions of purified factor H, for distinct occurrences of step b) of the method. By way of illustration, a given occurrence of step b) is carried out with a first composition of purified factor H and the next occurrence of step b) is carried out with a second composition of purified factor H. In these embodiments, several successive steps b) performed during the successive cycles of carrying out steps b) to e) may be carried out with the same composition of purified factor H, or else with distinct compositions of purified factor H, as is illustrated in the examples.

Thus, in certain embodiments of the anti-FH aptamer method, at least two characteristics, among the following characteristics, are combined:

(i) two successive occurrences of step b) are carried out with the same composition of purified factor H, and (ii) two successive occurrences of step b) are carried out with distinct compositions of purified factor H.

In certain embodiments of the method, the amount of anti-FH nucleic aptamers used in step b) may be varied in two distinct occurrences of carrying out step b).

In certain embodiments of the method, the amount of purified factor H used in step b) may be varied in two distinct occurrences of carrying out step b).

In the embodiments in which the respective amounts of anti-FH aptamers and of purified factor H vary by the same order of magnitude, then the joint variation of the amount of anti-FH aptamers and of the amount of purified factor H does not modify the molar ratio of the two "reagents", from one occurrence of step b) to another.

In the embodiments in which the respective amounts of anti-FH aptamers and of purified factor H vary with distinct orders of magnitude, then the joint variation of the amount of anti-FH aptamers and of the amount of purified factor H modifies the molar ratio of the two "reagents", from one occurrence of step b) to another.

In certain embodiments of the anti-FH aptamer method, at least two characteristics, among the following characteristics, are combined:
  (i) two successive occurrences of step b) are carried out with the same amount of anti-FH aptamers and the same amount of purified factor H,
  (ii) two successive occurrences of step b) are carried out with a distinct amount of anti-FH aptamers and a distinct amount of purified factor H and in an identical anti-FH aptamer/purified factor H molar ratio, and
  (iii) two successive occurrences of step b) are carried out with a distinct amount of anti-FH aptamers and a distinct amount of purified factor H and in a distinct anti-FH aptamer/purified factor H molar ratio.

In certain embodiments of the method for obtaining anti-FH aptamers of the invention, the duration of step b) of bringing the anti-FH aptamers into contact with the purified factor H may be identical or else distinct, for two successive occurrences of the method.

The various embodiments of step b) of the method for obtaining anti-FH aptamers above are illustrated in example 1.

Without wishing to be bound by any theory, the applicant thinks that the use of distinct compositions of purified factor H, at distinct occurrences of step b) of the method, promotes the selection of anti-FH aptamers capable of binding to factor H originating from samples of varied origin.

According to a first example, the use of purified human factor H of plasma origin and of purified recombinant human factor H, at distinct occurrences of step b) of the method, promotes the selection of anti-FH aptamers capable of binding both to human plasma factor H and to recombinant human factor H.

According to a second example, the use of distinct preparations of purified human factor H having a low content of degraded factor H, in particular of nonproteolyzed factor H, at distinct occurrences of step b) of the method, promotes the selection of anti-FH aptamers capable of binding selectively to nondegraded native factor H, said aptamers binding sparingly or not at all to degraded forms of factor H, for example to proteolytic fragments of 37 kDa and of 110 kDa generated after cleavage of native human factor H between residues $Arg_{223}$ and $Arg_{324}$.

In certain embodiments, the duration of step c) of separation between (i) the nucleic acid(s) which has (have) formed complexes with the factor H and (ii) the nucleic acids which have not formed complexes with the factor H may be varied. Step d) comprises one or more successive steps of washing with an appropriate buffer solution. The selectivity of the method for obtaining anti-FH aptamers having a strong affinity for the target factor H is increased with (i) an increasing duration of the washing step(s) carried out in step c) and with (ii) an increasing number of washing steps carried out in step c).

According to yet other embodiments, a method for obtaining an anti-FH aptamer may comprise one or more steps of selecting those of the aptamers which allow the formation of complexes with factor H in the presence of a buffer solution comprising a magnesium salt, for example $MgCl_2$. The step of selecting these aptamers may consist in carrying out at least one occurrence of step b) of the method with a medium, including a buffer solution, comprising a final $MgCl_2$ concentration of at least 1 mM, which encompasses at least 2 mM, 3 mM, 4 mM, 5 mM, 6 mM, 7 mM, 8 mM or 9 mM. According to a first alternative, the selection step with a buffer solution comprising a magnesium salt, for example $MgCl_2$, is carried out for a single selection cycle (steps a) to d)). According to a second alternative, the selection step with a buffer solution comprising a magnesium salt, for example $MgCl_2$, is carried out for a plurality of selection cycles, either of successive cycles, or of nonsuccessive cycles. According to a third alternative, the selection step with a buffer solution comprising a magnesium salt, for example $MgCl_2$, is carried out for each selection cycle.

In certain embodiments, use is made, in step b), of a buffer solution comprising magnesium chloride, for example a buffer solution of 50 mM Tris-HCl at pH 7.5, 150 mM NaCl and 10 mM $MgCl_2$ compared with a buffer solution which is identical but free of magnesium chloride.

According to yet other embodiments, a method for obtaining an anti-FH aptamer may be of the type which promotes the selection of those of the aptamers which allow the formation of complexes with factor H, it being possible for said complexes to be dissociated, with release of the factor H, by bringing said complexes into contact with a medium comprising a divalent-ion-chelating agent, for example EDTA.

In these particular embodiments, use is made, in step c), of a buffer solution comprising a divalent-ion-chelating agent, for example EDTA. Use may be made, in step c), of an elution buffer solution comprising EDTA at the final concentration of at least 1 mM and of at most 500 mM. Carrying out step c) in the presence of EDTA promotes the selection of anti-FH nucleic aptamers which, when they are involved in complexes with the target factor H, release said target factor H when said complexes are brought into contact with an elution buffer solution comprising EDTA, in particular EDTA at a final concentration of at least 1 mM and of at most 500 mM.

Thus, in certain embodiments of the method for obtaining anti-FH aptamers, at least one occurrence of step c), advantageously a plurality of occurrences of step c), or else all of the occurrences of step c), are carried out with a buffer solution comprising EDTA, in particular at a final EDTA concentration defined above.

In certain embodiments of the method, the specificity of the anti-FH aptamers with respect to the target factor H may be further increased by carrying out one or more counterselection steps. In certain embodiments, at least one counterselection step is carried out before the first occurrence of a selection step (steps a) to d) of the method). In certain embodiments, at least one selection step, which is inserted between two occurrences of a selection step of the method, is carried out. In certain embodiments, at least one counterselection step is carried out after the final occurrence of a selection step of the method.

For example, it is possible to add to any one of the embodiments of the method which are described above one or more steps of incubating the aptamers obtained at the end of an occurrence of step d) with a non-target factor H, for example a non-human factor H when it is desired to obtain nucleic aptamers specific for human factor H. In these embodiments, a step of bringing the nucleic acids obtained into contact with a non-target factor H is included at the end of an occurrence of step c) or of step d), and the anti-FH aptamers which have not formed complexes with said non-target factor H are recovered. The selected aptamers which have not formed complexes with the non-target factor H may be directly used as anti-FH aptamers according to the invention. Alternatively, the selected aptamers which have not formed complexes with the non-target factor H are subjected to one or more additional selection cycles, by repetition of steps a) to d). According to a first alternative, the step of counterselection with a non-target factor H is carried out at the end of a single selection cycle (steps a) to d)). According to a second alternative, the step of counterselection with a non-target factor H is carried out at the end of a plurality of selection cycles, either of successive cycles, or of non-successive cycles. According to a third alternative, the step of counterselection with a non-target factor H is carried out at the end of each selection cycle of the method.

The above embodiments are used in particular for obtaining anti-human FH aptamers produced in a transgenic animal, in which one or more steps of counterselection with natural factor H or recombinant factor H from said transgenic animal are carried out.

The specificity and/or the affinity of the anti-FH aptamers may also be increased by adding to any one of the embodiments of the method described above one or more steps of counterselection with respect to the material used to retain the nucleic acids which have formed complexes with the factor H, used in step c) of the method. The examples illustrate the implementation of a method for obtaining anti-FH aptamers for which a nitrocellulose membrane is used in step c), said method systematically comprising, starting from the first repetition of the sequence of steps a) to d), and optionally also at each subsequent repetition, a step of counterselection by removal of the nucleic aptamers which bind to the nitrocellulose membrane. In these embodiments, the aptamers obtained at the end of at least one occurrence of step c) or of step d) are brought into contact with the material used to retain the nucleic acids, for example a nitrocellulose membrane, and then the aptamers which are not bound to said material (i) are either used directly as anti-FH aptamers, (ii) or are subjected to one or more additional selection cycles, by repetition of steps a) to d).

The characteristics of the anti-FH aptamers, and in particular their inability to bind to proteins other than factor H, may also be improved by steps of counterselection by removal of the aptamers which bind to proteins other than the target factor H. In order to obtain anti-FH aptamers which can be used for detecting or purifying plasma factor H, it is advantageous to include in the method one or more steps of counterselection with respect to one or more plasma proteins other than factor H, or with respect to mixtures of plasma proteins free of factor H. Such counterselection steps promote in particular the obtaining of anti-FH aptamers which do not bind to complement proteins, in particular which do not bind to complement protein C3. The examples illustrate a method comprising steps of counterselection with respect to two mixtures of human plasma proteins, respectively factor H-depleted human serum and a factor H-depleted human plasma cryosupernatant.

In the embodiments above, a step of bringing the nucleic acids obtained into contact with a composition comprising a mixture of plasma proteins is included at the end of an occurrence of step c) or of step d), and the anti-FH aptamers which have not formed complexes with said plasma proteins are recovered.

The selected aptamers which have not formed complexes with said plasma proteins may be directly used as anti-FH aptamers according to the invention. Alternatively, the selected aptamers which have not formed complexes with said plasma proteins are subjected to one or more additional selection cycles, by repetition of steps a) to d). According to a first alternative, the step of counterselection with a composition comprising a mixture of plasma proteins is carried out at the end of a single selection cycle (steps a) to d)). According to a second alternative, the step of counterselection with a composition comprising a mixture of plasma proteins is carried out at the end of a plurality of selection cycles, either of successive cycles, or of nonsuccessive cycles. According to a third alternative, the step of counterselection with a composition comprising a mixture of plasma proteins is carried out at the end of each selection cycle of the method.

According to yet other embodiments, a method for obtaining an anti-FH aptamer may be of the type of any one of the methods described above, to which may be added a step of selecting those of the aptamers of which the capacity to bind to the target protein is not impaired by the presence of an alkylene glycol or of a polyalkylene glycol.

According to yet other embodiments, a method for obtaining an anti-FH aptamer may be of the type of any one of the methods described above, to which may be added a step of selecting those of the aptamers of which the capacity to bind to the target protein is not impaired by the presence of ethylene glycol. The step of selecting these aptamers may be carried out with a medium, including a buffer solution, comprising a final ethylene glycol concentration of at least 0.5 M, which includes at least 1 M and 1.5 M.

According to yet other embodiments, a method for obtaining an anti-FH aptamer may be of the type of any one of the methods described above, to which may be added a step of selecting those of the aptamers of which the capacity to bind to the target protein is not impaired by the presence of propylene glycol. The step of selecting these aptamers may be carried out with a medium, including a buffer solution, comprising a final propylene glycol concentration of at least 10% (v/v), which includes at least 15%, 20%, 25%, 30%, 35%, 40%, 45% and 50%.

According to yet other embodiments, a method for obtaining an anti-FH aptamer may be of the type of any one of the methods described above, to which may be added a step of selecting those of the aptamers of which the capacity to bind to the target protein is not impaired by the presence of ethanol. The step of selecting these aptamers may be carried out with a medium, including a buffer solution, comprising a final ethanol concentration of at least 1% (v/v), which includes at least 1.5%, 2.0%, 2.5%, 3.0%, 3.5%, 4.0%, 4.5%, 5.0%, 5.5%, 6.0%, 6.5%, 7.0%, 7.5%, 8.0%, 9.0%, 9.5% and 10.0%.

| Table 1 of sequences | | |
|---|---|---|
| SEQ ID N° | Type | Designation |
| 1 | Nucleic acid | Common 5' region of the aptamers |
| 2 | Nucleic acid | Common 3' region of the aptamers |
| 3 to 42 | Nucleic acid | sequences of the central regions of the aptamers having sequences SEQ ID N° 117 to 156 (Family 1) |
| 43 to 60 | Nucleic acid | sequences of the central regions of the aptamers having sequences SEQ ID N° 159 to 176 (Family 2) |
| 61 to 64 | Nucleic acid | sequences of the central regions of the aptamers having sequences SEQ ID N° 177 to 180 (Family 3) |
| 65 to 66 | Nucleic acid | sequences of the central regions of the aptamers |

Table 1 of sequences

| SEQ ID N° | Type | Designation |
|---|---|---|
| 67 to 71 | Nucleic acid | having sequences SEQ ID N° 181 to 182 (Family 4) sequences of the central regions of the aptamers having sequences SEQ ID N° 183 to 187 (Family 5) |
| 72 to 116 | Nucleic acid | sequences of the central regions of the aptamers having sequences SEQ ID N° 188 to 232 |
| 117 to 158 | Nucleic acid | aptamers (Family 1) |
| 159 to 176 | Nucleic acid | aptamers (Family 2) |
| 177 to 180 | Nucleic acid | aptamers (Family 3) |
| 181 to 182 | Nucleic acid | aptamers (Family 4) |
| 183 to 187 | Nucleic acid | aptamers (Family 5) |
| 188 to 232 | Nucleic acid | other anti-FH aptamers |
| 233 | Nucleic acid | consensus sequence of Family 1 |
| 234 | Nucleic acid | consensus sequence of Family 1 found in SEQ ID N° 3 |
| 235 | Nucleic acid | consensus sequence of Family 2 |
| 236 | Nucleic acid | consensus sequence of Family 3 |
| 237 | Nucleic acid | consensus sequence of Family 4 |
| 238 | Nucleic acid | consensus sequence of Family 5 |
| 239 | Nucleic acid | MaptH1.1 N13-48 aptamer |
| 240 | Nucleic acid | MaptH1.1 N19-58 aptamer |
| 241 | Nucleic acid | MaptH1.1 N19-53 aptamer |
| 242 | Nucleic acid | MaptH1.1 N19-48 aptamer |
| 243 | Nucleic acid | MaptH1.1 N22-45 aptamer |

The present invention is also illustrated by the following examples.

EXAMPLES

Example 1

Obtaining Anti-FH Nucleic Aptamers 1.1. Target Factor H

Two preparations of purified human factor H were used, respectively:
- a composition of purified factor H sold by the company Calbiochem (San Diego, USA) under the reference 341274,
- a composition of purified factor H prepared by the applicant.

1.2. Mixture or Collection of Nucleic Acids

A random library of deoxyribonucleic acids (DNAs) having the generic sequence 5'-(SEQ ID No 1)-(N)$_{40}$-(SEQ ID No 2)-3', in which (N)$_{40}$ represents a random sequence 40 nucleotides in length, was used. The sequences SEQ ID No 1 and SEQ ID No 2 are fixed sequences which are used for the amplification of the factor H-binding sequences, at each selection cycle of the SELEX method.

For the needs (i) of regenerating the sense strand at the end of each selection cycle of the SELEX method and (ii) of testing the selectivity and/or the affinity of the anti-FH aptamers obtained at the end of each selection cycle of the SELEX method, the nucleic acids selected were coupled to biotin (molecular weight of 569.61), the biotin being bonded to the 5' end of the nucleic acid via a spacer chain consisting of a polyethylene glycol of PEG(C18) type (molecular weight of 344.3) sold by the company Sigma Aldrich (Saint Louis, Mo., USA).

1.3. Selection Buffer

A buffer of 50 mM Tris HCl at pH 7.5, 150 mM NaCl and 10 mM MgCl$_2$ was used as selection buffer.

1.4. Elution Buffer

A buffer of 50 mM Tris HCl at pH 7.5, 150 mM NaCl and 50 mM EDTA was used as elution buffer.

1.5. Selection of Anti-FH Nucleic Aptamers

For the selection of the anti-FH aptamers, the DNA library (approximately $10^{15}$ random sequences) was incubated with the purified factor H in the selection buffer (see §1.3 above).

The DNA library/factor H mixture is then filtered through a nitrocellulose membrane of the MF-Millipore Membrane Filter (reference HAWP02500) type sold by the company Millipore.

The DNA/factor H complexes which have been formed are retained on the filtering nitrocellulose membrane. The DNAs which have not formed complexes with the factor H pass through the filtering nitrocellulose membrane and are removed.

One or more washes of the filtering membrane with the selection buffer are carried out.

The DNAs retained on the nitrocellulose filter are eluted with the elution buffer (see §1.4. above).

The DNAs recovered after elution are amplified by PCR using a pair of primers hybridizing respectively with the sequences SEQ ID No 1 and SEQ ID No 2.

The sense strand is then regenerated by affinity chromatography on magnetic beads on which streptavidin is immobilized.

1.6.1. Counterselection with Respect to the Nitrocellulose

In order to carry out a step of counterselection with respect to the nitrocellulose, the DNAs which have been eluted at the end of a selection cycle are incubated in contact with the nitrocellulose membrane.

The DNAs not retained on the nitrocellulose membrane are amplified and then used to carry out the next selection cycle.

1.6.2. Counterselection with a Mixture of Plasma Proteins Free of Factor H

In order to carry out a step of counterselection with a mixture of plasma proteins, use was made respectively (i) of human serum free of factor H or (ii) of plasma cryosupernatant free of factor H.

Before the step of selection with factor H, the DNAs were incubated with the mixture of plasma proteins free of factor H, in the selection buffer previously used, under the following operating conditions:

The resulting solution was filtered on a nitrocellulose membrane and the DNAs not retained, which have not formed complexes with the plasma proteins, were recovered in the filtrate.

The DNAs not retained will then follow the selection cycle with factor H previously described.

1.6.3. Detailed Description of the Selection Method

The selection cycles were repeated according to the operating conditions explained in detail in table 2 below.

TABLE 2

| Cycle n° | DNA (pmol) | FH (pmol) | FH type | Incubation time (mins) | Number and duration of washes | Nitrocellulose counterselection | Other counterselection |
|---|---|---|---|---|---|---|---|
| 1 | 2000 | 1000 | LFB | 60 | 1 (1 min) | No | No |
| 2 | 400 | 200 | LFB | 60 | 2 (2 min) | Yes | No |

TABLE 2-continued

| Cycle n° | DNA (pmol) | FH (pmol) | FH type | Incubation time (mins) | Number and duration of washes | Nitrocellulose counterselection | Other counterselection |
|---|---|---|---|---|---|---|---|
| 3 | 400 | 200 | Calbiochem | 45 | 2 (2 min) | Yes | No |
| 4 | 200 | 100 | Calbiochem | 45 | 3 (3 min) | Yes | No |
| 5 | 200 | 100 | LFB | 30 | 3 (3 min) | Yes | No |
| 6 | 200 | 100 | LFB | 30 | 4 (4 min) | Yes | No |
| 7 | 200 | 50 | Calbiochem | 15 | 4 (13 min) | Yes | No |
| 8 | 200 | 50 | Calbiochem | 15 | 5 (20 min) | Yes | FH-depleted human serum |
| 9 | 200 | 50 | LFB | 10 | 5 (20 min) | Yes | FH-depleted human serum |
| 10 | 200 | 50 | LFB | 10 | 5 (20 min) | Yes | FH-depleted cryosupernatant |
| 11 | 200 | 50 | Calbiochem | 10 | 5 (20 min) | Yes | FH-depleted cryosupernatant |

As indicated in table 2, the absolute amounts, respectively of DNA and of factor H, were varied from one cycle to another of the SELEX method. However, an identical DNA/FH molar ratio was used for cycles no 1 to 6 (ratio of 2) and for cycles no 7 to 11 (ratio of 4), respectively.

The DNAs and the factor H were incubated for decreasing periods with the successive selection cycles.

The number of washing steps was increased with the successive selection cycles. Furthermore, the total duration of the washes was gradually increased.

Example 2

Figure 1A:
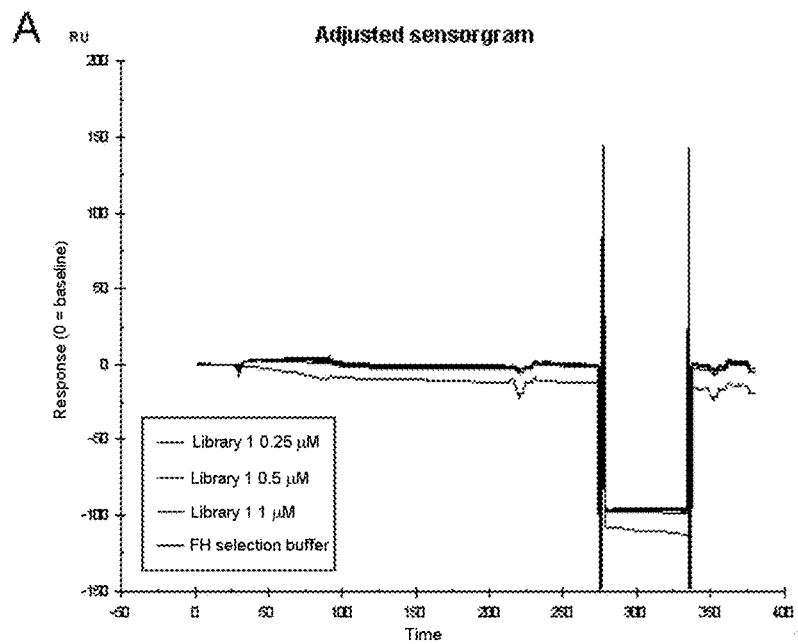
FIG. 1A illustrates the curves of binding of the nucleic acids of the starting nucleic acid library to human plasma factor H immobilized beforehand on a support.

Factor H-Binding Characteristics 2.1. Experimental Conditions
Apparatus Used:
Biacore T100
Chip:
The factor H (LFB) was immobilized using NHS/EDC chemistry (chip CMS, GE) to 5813 RU in a flow cell 2-1 (FC2-1). No protein is bound to flow cell no 1 (FC1) but this flow cell was subjected to the same treatment as flow cell no 2. The injected sample passes over FC1 and FC2 in order to rigorously subtract the background noise due to nonspecific interactions.
Buffer for Running and Diluting the Samples:
50 mM Tris, 150 mM NaCl, 10 mM $MgCl_2$, pH 7.5.
Flow:
30 µl/min, injection for 60 sec, dissociation for 60 sec.
Signal:
Signal on FC2 with subtraction of the signal on FC1.
Regeneration:
50 mM EDTA, pH 5, in water, twice 60 sec.
2.2. Results
The results are represented in FIGS. 1 and 2.
The change in the aptamer population selected after each cycle of carrying out the SELEX method is evaluated by measuring binding with the Biacore® technique. The capacity of the aptamer population to bind to the target factor H was measured.
A. Characterization of the Starting DNA Library
Firstly, it was verified that the starting DNA nucleic acid library does not exhibit any detectable affinity with factor H.
In a first test, the factor H was immobilized on the Biacore® support which consists of a chip of the CMS type sold by the company GE Healthcare, which comprises a gold support on which carboxymethylated dextran molecules are immobilized by the NHS method with EDC (a carbodiimide). The DNA library was injected at concentrations of 0.25 µM, 0.5 µM and 1 µM. No binding of the DNA library is observed on the factor H, whatever its concentration used (FIG. 1A).

Figure 1B:
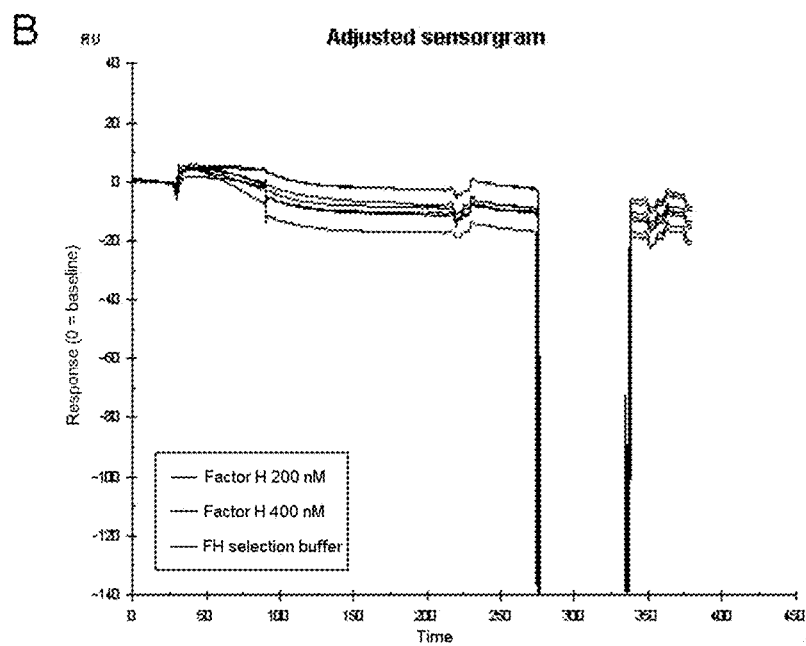
FIG. 1B illustrates the curves of binding of the human plasma factor H to the nucleic acids of the starting aptamer library immobilized beforehand on a support.

In a second test, the library was immobilized on a streptavidin chip and the factor H was injected at concentrations of 200 nM and 400 nM. No binding of the factor H is observed on the support on which the nucleic acids of the starting DNA library are immobilized (FIG. 1B).

The results show that the starting DNA library therefore has no detectable affinity for factor H, before the beginning of the process of selecting nucleic aptamers by means of the SELEX method.

B. Characterization of the Anti-Factor H Nucleic Aptamers
B.1. Affinity for Factor H
The ability of the sets of nucleic acids selected to bind to factor H was characterized. The factor H-binding capacity of the sets of nucleic acids obtained at the end of the $5^{th}$, $6^{th}$ and $7^{th}$ cycles of carrying out the SELEX method was measured using the Biacore® technique.

The results are represented in FIG. 2.

Figure 2A:
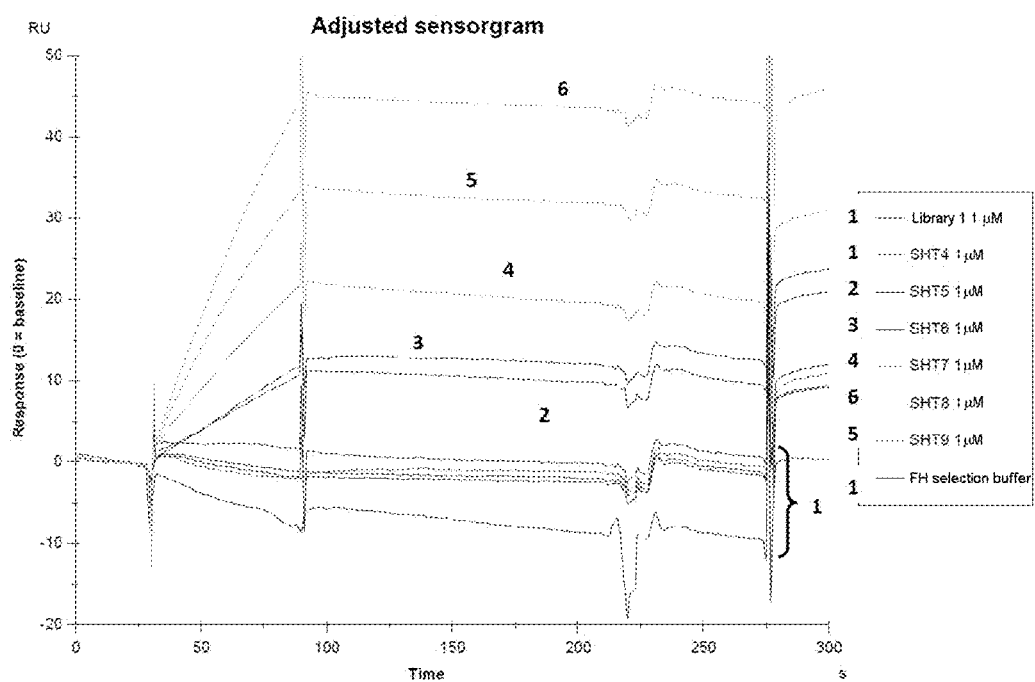
FIG. 2A illustrates the curves of binding of the nucleic acids of the starting nucleic acid library and of populations enriched with nucleic acids which bind to human plasma factor H immobilized beforehand on a support. Curves "1": comprise (i) the curves of the selection buffer solution (comprising the lowest curve), (ii) the curve of the nucleic acids contained in the starting library, and (iii) the curve of the nucleic acids obtained at the end of cycle no 4 (SHT4) of the SELEX process. Curve no 2: the curve of the nucleic acids obtained at the end of cycle no 5 (SHT5) of the SELEX process. Curve no 3: the curve of the nucleic acids obtained at the end of cycle no 6 (SHT6) of the SELEX process. Curve no 4: the curve of the nucleic acids obtained at the end of cycle no 7 (SHT7) of the SELEX process. Curve no 5: the curve of the nucleic acids obtained at the end of cycle no 9 (SHT9) of the SELEX process. Curve no 6: the curve of the nucleic acids obtained at the end of cycle no 8 (SHT8) of the SELEX process.

FIG. 2A shows the results of measuring the capacity for binding to factor H immobilized on a support of the sets of nucleic acids obtained at the end of cycles 5 to 9 (SHT5 to SHT9). The results show that the affinity of the nucleic aptamers increases with the number of selection cycles. It is noted that the results of FIG. 1 indicate an affinity of the nucleic acids obtained at the end of cycle no 8 which is greater than that of the nucleic acids obtained at the end of cycle no 9.

Figure 2B:
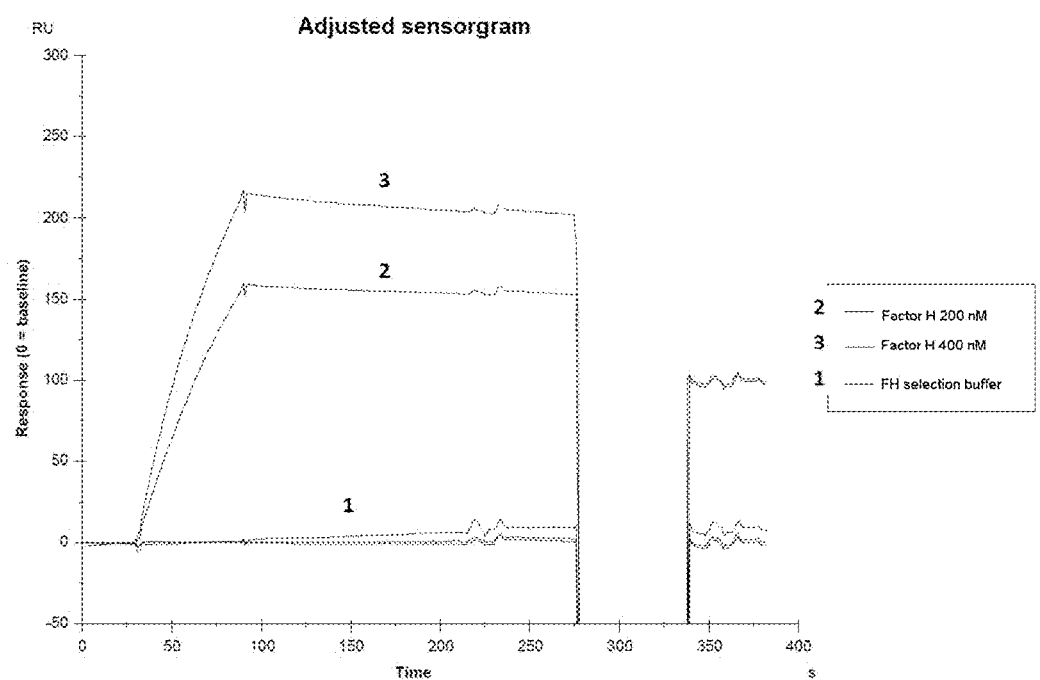
FIG. 2B illustrates the curves of binding of the human plasma factor H to the nucleic acid-enriched population resulting from cycle no 6 of selection by the SELEX method. The nucleic acids were immobilized beforehand on a support.

FIG. 2B shows the results of measuring the capacity for binding of factor H to the nucleic aptamers obtained at the end of cycle no 6, which are immobilized on a support. Curve no 1 (lower curve): nucleic acid-free selection buffer solution. Curve no 2: human plasma factor H at the final concentration of 400 nM. Curve no 3: human plasma factor H at the concentration of 200 nM.

Moreover, table 3 below gives the results of selective binding of a variety of nucleic aptamers according to the invention to human factor H. The aptamers tested were selected at the end of cycle no 7 of the SELEX method described in example

TABLE 3

| Sequence name | Sequence | Factor H-binding stability (RU) |
|---|---|---|
| FAM1-1 | GGGTCAATGCCAGGTCTCCGGTCTC GAGATGGGGTCTGGTGGTTATACGC TCTCAGTGATCGGCTCGCAAGCAGT C (SEQ ID N° 117) | 19.2* |

TABLE 3-continued

| Sequence name | Sequence | Factor H-binding stability (RU) |
|---|---|---|
| FAM1-2 | GGGTCAATGCCAGGTCTCACCGTCATCGAGAAGGGTCTGGTGGTTATACGTTCTCGTGATCGGCTCGCAAGCAGTC (SEQ ID N° 118) | 47 |
| FAM1-3 | GGGTCAATGCCAGGTCTCGGACCGCGATGGAGAGGGGTCTGGTGGTTATACGCTATGCATCGGCTCGCAAGCAGTC (SEQ ID N° 119) | 20.95 |
| FAM1-4 | GGGTCAATGCCAGGTCTCGGGCCGCGATGGAGAGGGGTCTGGTGGTTATACGCTATGCATCGGCTCGCAAGCAGTC (SEQ ID N° 157) | 26.2 |
| FAM1-5 | GGGTCAATGCCAGGTCTCGCAGAGGTGCGAGGGCGGTGGGGTCTGGTGGTTATACGCATCGGCTCGCAAGCAGTC (SEQ ID N° 124) | 21.25 |
| FAM1-6 | GGGTCAATGCCAGGTCTCGGCAGGGAGGAGGAATCGGGACAGGCGGTTATACGGATTCATCGGCTCGCAAGCAGTC (SEQ ID N° 128) | 30 |
| FAM1-7 | GGGTCAATGCCAGGTCTCGGGGGGCCGGTTATACGGGTCAGGCGGTTATACGGTATTCATCGGCTCGCAAGCAGTC (SEQ ID N° 135) | 15.45 |
| FAM1-8 | GGGTCAATGCCAGGTCTCGGGGTGCGAGGGTCTGGTGGTTATACGTCGTCACCTCTAGATCGGCTCGCAAGCAGTC (SEQ ID N° 150) | 35.95 |
| FAM1-9 | GGGTCAATGCCAGGTCTCGAGGGGCTTTTGGGAGGGACTGGTGGTTATACGTCCCAATATCGGCTCGCAAGCAGTC (SEQ ID N° 152) | 57.8 |
| FAM1-10 | GGGTCAATGCCAGGTCTCGCGGTGGACGGGGCTGGCGGTTATACGGTCCTTACGCGGTATCGGCTCGCAAGCAGTC (SEQ ID N° 153) | 73.5 |
| FAM1-11 | GGGTCAATGCCAGGTCTCCGGGGCAGGCGGTTATACGGGAGAACGGTATGGGGGACTATCGGCTCGCAAGCAGTC (SEQ ID N° 138) | 16.9 |
| FAM1-12 | GGGTCAATGCCAGGTCTCACCGGGTCAGGCGGTTATACGGGTGAGGGCAGGTACATACATCGGCTCGCAAGCAGTC (SEQ ID N° 158) | 18.2 |
| FAM1-13 | GGGTCAATGCCAGGTCTCGGGCACGGGTCAGGCGGTTATACGGTGCCCATTGTTCTTTATCGGCTCGCAAGCAGTC [SEQ ID N° 142] | 30.65 |
| FAM2-1 | GGGTCAATGCCAGGTCTCCCGGTTACCGCGCTAAGCTTGGCGATGGTGTTAGTGCTGATCGGCTCGCAAGCAGTC [SEQ ID N° 159] | 29.65 |
| FAM2-2 | GGGTCAATGCCAGGTCTCCCGGTTACTGCCGTAGTTGTCTTACGGTGGTGTTAGTGGCATCGGCTCGCAAGCAGTC (SEQ ID N° 161) | 22.4 |
| FAM2-3 | GGGTCAATGCCAGGTCTCCCGGTTACCTCCATTGGTGGTGTTAGTGGCTTTGTAGGATATCGGCTCGCAAGCAGTC [SEQ ID N° 164] | 18.25 |
| FAM2-4 | GGGTCAATGCCAGGTCTCCCGGTTACCAGTTGGTGTTTGTGGCTTTGCACGTCTGCATATCGCTCGCAAGCAGTC (SEQ ID N° 165) | 27.55 |
| FAM2-5 | GGGTCAATGCCAGGTCTCCCGGTTACCAACTATGATAGTATGGTGTTTGTGGCATGATCGGCTCGCAAGCAGTC (SEQ ID N° 172) | 22.25 |
| FAM2-6 | GGGTCAATGCCAGGTCTCCCGGTTACCATCGAGGACGTCGCTTGGTGTTTGTGGCATGATCGGCTCGCAAGCAGTC (SEQ ID N° 174) | 22.05 |
| FAM2-7 | GGGTCAATGCCAGGTCTCCCGGTTACCAAGATCGTTGTTCTTGGTGTTAGTGGCATTCATCGGCTCGCAAGCAGT (SEQ ID N° 175)C | 22.05 |
| FAM3 | GGGTCAATGCCAGGTCTCTGAGGCGCAGATGTGGAGGCTTTTACAGGCGGTGCGGAACATCGGCTCGCAAGCAGTC (SEQ ID N° 177) | 11.7 |
| FAM4 | GGGTCAATGCCAGGTCTCCAAAGGGGGGGGTTGGGGGACCGTCCGTTGTTGATCTCACATCGGCTCGCAAGCAGTC (SEQ ID N° 181) | 25.85 |
| IND1 | GGGTCAATGCCAGGTCTCGGTGGGAGGTGAGGTCGTTGGACGGTGGCAGGGATTTTGATCGGCTCGCAAGCAGTC (SEQ ID N° 193) | 20.1 |

*value of arbitrary resonance units (RU) at the signal peak.

The results of table 3 above show that all of the nucleic aptamers tested bind selectively to factor H.

Example 3

Obtaining an Affinity Support

Grafting buffer: 100 mM sodium acetate, pH=4.2.
Preparation of 1595 µl of aptamer at 2.5 g/l in grafting buffer, i.e.: 4 mg of anti-FH aptamer.
For the grafting, the following were respectively used:
a) for preparing a first affinity support, an anti-FH aptamer comprising a polynucleotide chosen from the sequences SEQ ID No 117 to 158 bonded at its 5' end to the spacer chain 11-(trifluoroacetamido)-3,6,9-trioxaundecan-1-yl[(2-cyanoethyl)-(N,N-diisopropyl)] (hydrophilic C11 spacer provided by the company Link Technologies);
b) for preparing a second affinity support, an aptamer comprising the polynucleotide chosen from the sequences SEQ ID No 117 to 158 bonded at its 5' end to a spacer chain 12-(4-monomethoxytritylamino)dodecyl[(2-cyanoethyl)-(N,N-diisopropyl)] (C12 spacer) and bonded at its 3' end to an oligo-dT;
c) for preparing a third affinity support, an aptamer comprising the polynucleotide chosen from the sequences SEQ ID No 117 to 158 bonded at its 5' end to a spacer chain 6-(trifluoroacetylamino)hexyl[(2-cyanoethyl)-(N,N-diisopropyl)] (C6 spacer).
Preparation of 1 ml of gel comprising NHS-activated carboxylic acid groups, namely the "NHS Activated Sepharose 4 fast flow" pre-activated gel (GE), by carrying out washing with 1 mM HCl, then washing with the grafting buffer.

It was verified that the pH in the aptamer preparation in the buffer solution was 4.2.

The aptamer preparation was mixed with 1 ml of pre-activated gel. The pre-activated gel was incubated in the presence of the aptamers with stirring for 48 h (+/−2H) to 4° C.

Half a reaction volume (797 µl) of 200 mM borate buffer, pH=9, was added while stirring, and then the mixture was incubated for 8 h with stirring at 4° C.

The supernatant was recovered and the amount of non-grafted aptamers was assayed.

2 ml of 0.1 M Tris-HCl, pH=8.5, was added with stirring for 2 h30 at 4° C. in order to block the coupling reaction.

Three cycles of addition/stirring/removal of the supernatant comprising: 1) 1 ml of 0.1 M Tris-HCl, pH=8.5, then 2) 1 ml of sodium acetate at 0.1 M, 0.5 M NaCl, pH=4.0, were carried out in order to obtain a ready-to-use affinity support.

The results show that the resulting solution obtained after carrying out the chemical grafting does not comprise a detectable amount of nucleic aptamer, i.e., under the analysis conditions used, comprises an amount of aptamer of less than 0.08 mg/ml.

It may be deduced from these results that the grafting yield is 100%, or very close to 100%.

A finer analysis of the characteristics of the affinity support made it possible to define the following characteristics:

Aptamer grafting capacity ($C_{grafting}$): 6 mg/ml of gel.
Grafting yield: greater than 98%.
Final anti-FH aptamer concentration of the gel ($C_{final\ of\ the\ gel}$): greater than 6 mg/ml.

Example 4

Purification of a Plasma Factor H

A. Materials and Methods

The affinity support was prepared from a solid support material consisting of a matrix onto which streptavidin was grafted (streptavidin-agarose—Novagen®).

A volume of 1 ml of gel was introduced into a container consisting of a column (i.d. 11 mm). The gel was washed with purified water in order to remove the storage solvent.

The outlet of the packed column (gel bed height=1 cm) is connected to an absorbance detector equipped with a UV filter at 254 nm and a recording device. MaptH1.1 biotinylated anti-human FH nucleic aptamers (SEQ ID No 144) are dissolved in purified water at the final concentration of 0.5 mg/0.187 ml, i.e. a final molar concentration of 0.1 mM. The nucleic aptamer solution was activated at 95° C. according to the standard cycle, for immobilization of the aptamers on the solid support material.

The nucleic aptamer solution was diluted beforehand with 4.8 ml of purified water and then 1.5 ml of Me$^{++}$ buffer (5× concentrated).

The absorbance detector is adjusted to 1 AUFS (Absorbance Unit Full Scale) and the OD at 254 nm of this solution is recorded at 0.575 AU254. The biotinylated nucleic aptamer solution is injected onto the prepacked streptavidin-agarose gel and recirculated with a peristaltic pump at a flow rate of 2.5 ml/minute, i.e. a contact time on the gel of 24 seconds (inlet/outlet I/O). Under these conditions, the OD at 254 nm stabilizes rapidly at 0.05 AU254, i.e. a value of 91% of theoretical coupling, i.e. 0.455 mg of nucleic aptamers per milliliter of gel.

Washing with a 10 mM $CaCl_2$+4 mM $MgCl_2$ buffer and then in 2M NaCl is carried out in order to remove the nucleic aptamers which are not specifically bound to the streptavidin molecules grafted onto the solid support material.

B. Results

A solution of purified human plasma factor H which has been preadjusted to 50 mM $MgCl_2$, 50 mM NaCl and pH 7.5 is injected onto the aptamer-agarose (affinity support) gel with a peristaltic pump at a flow rate of 0.5 ml/minute, i.e. a contact time with the affinity support of 10 minutes (I/O).

After injection, the gel is washed in 50 mM Tris+2M NaCl+50 mM $MgCl_2$ buffer+at pH 7.5.

A volume of 10 ml of nonadsorbed solution is collected.

The plasma factor H is eluted with a 50 mM Tris+500 mM EDTA buffer at pH 8.0. The elution peak is collected according to the OD profile.

FIG. 3 illustrates a human plasma factor H chromatography profile with continuous monitoring of the absorbance values (O.D.) at 254 nanometers.

In FIG. 3, from the left to the right of the figure, peak no 1 of the absorption curve, after the moment of injection, illustrates the fraction which is not retained on the affinity support. Peak no 2 of the curve illustrates the factor H fraction which is eluted.

The results of FIG. 3 show that the fraction not retained by the affinity support represents 26% of the starting material which absorbs at 254 nanometers. The results of FIG. 3 show that the human plasma factor H fraction which is retained on the affinity support, and then eluted, represents 74% of the starting material which absorbs at 254 nanometers.

The starting human plasma factor H sample, the content of the fraction not retained on the affinity support, and the content of the eluate fraction were analyzed on SDS PAGE according to the following protocol: Gels NOVEX (Invitrogen) 10-well, 4-12%, Bis-Tris; MES migration buffer, migration at 200 V for 50 min. $AgNO_3$ staining (GE kit).

The electrophoresis gel analysis results are represented in FIG. 5A.

The results of FIG. 5A show that the purified starting human plasma factor H solution still contains impurities visualized with silver nitrate. On the other hand, the results of FIG. 5A show that the elution fraction comprises a protein material which migrates according to a single band despite the known high sensitivity of visualization with silver nitrate.

The electrophoresis gel analysis results of FIG. 5A show that the affinity support on which MaptH1.1 nucleic aptamers are immobilized is capable of purifying human plasma factor H and of very significantly improving the purity level of a product purified by conventional approaches.

Example 5

Purification of a Recombinant Factor H

In example 5, an affinity support that was prepared as described in example 4 was used.

A preparation of human factor H consisting of a culture supernatant of recombined cells producing recombinant human factor H was used. A recombinant human factor H cell culture supernatant which has been pre-adjusted to 50 mM Tris, 50 mM NaCl, 10 mM $MgCl_2$ and pH 7.5 is injected onto the aptamer-agarose (affinity support) gel with a peristaltic pump at a flow rate of 0.5 ml/minute, i.e. a contact time with the affinity support of 20 minutes (I/O).

After injection, the gel is washed in 50 mM Tris+2 M NaCl+10 mM MgCl$_2$ buffer+at pH 7.5.

A volume of 10 ml of nonadsorbed solution is collected.

The recombinant human factor H is eluted with a 50 mM Tris+500 mM EDTA buffer at pH 8.0. The elution peak is collected according to the OD profile.

FIG. 4 illustrates a recombinant human factor H chromatography profile with continuous monitoring of the absorbance values (O.D.) at 254 nanometers.

In FIG. 4, from the left to the right of the figure, peak no 1 of the absorption curve, after the moment of injection, illustrates the fraction which is not retained on the affinity support. Peak no 2 of the curve illustrates the recombinant factor H fraction which is eluted. Peak no 3 illustrates the fraction resulting from a step of regenerating the affinity support.

The results of FIG. 4 show that the fraction not retained by the affinity support represents 95% of the starting material which absorbs at 254 nanometers. The results of FIG. 4 show that the recombinant human factor H fraction which is retained on the affinity support, and then eluted, represents 2% of the starting material which absorbs at 254 nanometers. Finally, the results of FIG. 4 show that 3% of the starting material which absorbs at 254 nanometers was retained nonspecifically on the affinity support.

The starting recombinant human factor H sample, the content of the fraction not retained on the affinity support, and the content of the eluate fraction were analyzed on SDS PAGE according to the following protocol: Gels NOVEX (Invitrogen) 10-well, 4-12%, Bis-Tris; MES migration buffer, migration at 200 V for 50 min. AgNO$_3$ staining (GE kit).

The electrophoresis gel analysis results are represented in FIG. 5B.

The results of FIG. 5B show that the starting recombinant human factor H solution is very heterogeneous and comprises a large variety of cell proteins of distinct molecular weights. The results of FIG. 5B also show a great heterogeneity of the protein entities contained in the nonretained fraction. On the other hand, the results of FIG. 5B show that the elution fraction consists of a very pure product which comprises a protein material that migrates according to a single band, despite the sensitivity of visualization with silver nitrate. The electrophoresis gel analysis results of FIG. 5B show that the affinity support on which MaptH1.1 nucleic aptamers are immobilized is capable of purifying recombinant human factor H from a complex cell culture supernatant sample comprising a large variety of plasma proteins and makes it possible to obtain, in a single step, a very high level of purity.

Example 6

Selection of Optimized Anti-FH Nucleic Aptamers

A. Materials and Methods
Apparatus Used:
Biacore T100.
Chip:
Factor H (LFB) was immobilized using NHS/EDC chemistry (CMS chip, GE) at 5813 RU in a flow cell 2-1 (FC2-1). No protein is bound on flow cell no 1 (FC1), but this flow cell underwent the same treatment as flow cell no 2. The injected sample passes over FC1 and FC2 in order to rigorously subtract the background noise due to nonspecific interactions.
Buffer for Running and Diluting Samples:
50 mM Tris, 50 mM NaCl, 50 mM MgCl$_2$, pH 7.5.
Flow:
30 µl/min, injection for 60 sec, dissociation for 60 sec.
Signal:
Signal on FC2 with subtraction of the signal on FC1.
Regeneration:
500 mM EDTA, pH 8, in water, twice 60 sec.

B. Results

A plurality of nucleic aptamers derived from the MaptH1.1 nucleic aptamer having sequence SEQ ID No 144 were synthesized, respectively the following aptamers: (i) MaptH1.1 N13-48 (SEQ ID No 239), (ii) MaptH1.1 N19-58 (SEQ ID No 240), (iii) MaptH1.1 N19-53 (SEQ ID No 241); (iv) MaptH1.1 N19-48 (SEQ ID No 242) and (v) MaptH1.1 N22-45 (SEQ ID No 243). The sequences of these nucleic aptamers are represented in table 4 below.

TABLE 4

| Ref | SEQ ID N° | Sequence |
|---|---|---|
| MaptH1.1 N13-48 | 239 | caggtctcgg gcacgggtca ggcggttata cggtgccc |
| MaptH1.1 N19-58 | 240 | gg gcacgggtca ggcggttata cggtgcccat tgttctttt |
| MaptH1.1 N19-53 | 241 | gg gcacgggtca ggcggttata cggtgcccat tgt |
| MaptH1.1 N19-48 | 242 | gg gcacgggtca ggcggttata cggtgccc |
| MaptH1.1 N22-45 | 243 | cacgggtca ggcggttata cggtg |

The MaptH1.1 N13-48 aptamer is a nucleic acid consisting of the sequence ranging from the nucleotide in position 13 up to the nucleotide in position 48 of the MaptH1.1 nucleic aptamer having sequence SEQ ID No 144.

The MaptH1.1 N19-58 aptamer is a nucleic acid consisting of the sequence ranging from the nucleotide in position 19 up to the nucleotide in position 58 of the MaptH1.1 nucleic aptamer having sequence SEQ ID No 144.

The MaptH1.1 19-53 aptamer is a nucleic acid consisting of the sequence ranging from the nucleotide in position 19 up to the nucleotide in position 53 of the MaptH1.1 nucleic aptamer having sequence SEQ ID No 144.

The MaptH1.1 N19-48 aptamer is a nucleic acid consisting of the sequence ranging from the nucleotide in position 19 up to the nucleotide in position 48 of the MaptH1.1 nucleic aptamer having sequence SEQ ID No 144.

The MaptH1.1 N22-45 aptamer is a nucleic acid consisting of the sequence ranging from the nucleotide in position 22 up to the nucleotide in position 45 of the MaptH1.1 nucleic aptamer having sequence SEQ ID No 144.

The ability of each of the above aptamers to bind to recombinant human factor H was tested by measuring binding of the aptamers on a support obtained in accordance with the Materials and Methods section, according to the Biacore® technique.

The results are represented in FIG. 7.

The results of FIG. 7 show that all the aptamers derived from the MaptH1.1 nucleic aptamer having sequence SEQ ID No 144 bind to the human factor H immobilized on the support.

In particular, it is observed that the MaptH1.1 N22-45 nucleic aptamer, which is the nucleic aptamer with the shortest length, retained the ability of the MaptH1.1 parent aptamer to bind to human factor H, although its affinity for human factor H is lower than that of the MaptH1.1 parent nucleic aptamer. Consequently, the results show that the part of the MaptH1.1 nucleic aptamer having sequence SEQ ID No 144 ranging from the nucleotide in position 22 up to the nucleotide in position 45 is sufficient to confer on said nucleic aptamer the capacity to bind to human factor H.

These results are confirmed by the fact that all the other nucleic aptamers, respectively the aptamers (i) MaptH1.1 N13-48 (SEQ ID No 239), (ii) MaptH1.1 N19-58 (SEQ ID No 240), (iii) MaptH1.1 N19-53 (SEQ ID No 241) and (iv) MaptH1.1 N19-48 (SEQ ID No 242), all comprise the part of the MaptH1.1 parent aptamer ranging from the nucleotide in position 22 up to the nucleotide in position 45 and all retained a good human factor H-binding capacity.

Moreover, an increasing affinity with human factor H is measured for the succession of nucleic aptamers MaptH1.1 N22-45 (SEQ ID No 243), MaptH1.1 N19-48 (SEQ ID No 242), MaptH1.1 N19-53 (SEQ ID No 241), MaptH1.1 N19-58 (SEQ ID No 240) and MaptH1.1 N13-48 (SEQ ID No 239).

Thus, among the nucleic aptamers comprising the region of the MaptH1.1 parent aptamer ranging from the nucleotide in position 22 up to the nucleotide in position 45 which were tested, it is the MaptH1.1 N13-48 nucleic aptamer (SEQ ID No 239) which possesses the strongest affinity for human factor H. The MaptH1.1 N13-48 aptamer (SEQ ID No 239) may also be denoted "MaptH1.1CSO" for the purposes of the present description.

The invention claimed is:

1. A nucleic aptamer which binds to factor H and which comprises SEQ ID NO:243.

2. The nucleic aptamer as claimed in claim 1, which is of formula (III) below:

$$5'\text{-}[N1]_x\text{-}[SEQ\ ID\ NO:243]\text{-}[N2]_y\text{-}3' \quad (III),$$

wherein:
- x is an integer equal to 0 or 1, and
- y is an integer equal to 0 or 1,
- N1 is a nucleic acid having a length of from 1 to 100 nucleotides, and
- N2 is a nucleic acid having a length of from 1 to 100 nucleotides.

3. The nucleic aptamer of claim 1, selected from SEQ ID NO:144 and SEQ ID NO:239 to 243.

4. The nucleic aptamer of claim 1, wherein the nucleic aptamer binds to a factor H selected from a plasma factor H, a recombinant factor H and a transgenic factor H.

5. The nucleic aptamer of claim 1, wherein the nucleic aptamer binds to a factor H selected from a human factor H and a non-human factor H.

6. The nucleic aptamer of claim 1, wherein the nucleic aptamer is a deoxyribonucleotide aptamer.

7. A compound of formula (II) below:

$$[IMM]_x\text{-}[SPAC]_y\text{-}[APT] \quad (II)$$

wherein:
- [IMM] is a compound for immobilization on a support,
- [SPAC] is a spacer chain,
- [APT] is a nucleic acid which binds specifically to factor H as defined in claim 1,
- x is an integer equal to 0 or 1, and
- y is an integer equal to 0 or 1.

8. An affinity support for the selective binding of factor H, comprising a solid support material on which nucleic aptamers as claimed in claim 1 are immobilized.

9. An affinity support for the selective binding of factor H, comprising a solid support material on which a compound of formula (II) as claimed in claim 7 is immobilized.

10. A method for obtaining an affinity support for the selective binding of factor H, comprising the following steps:
   a) providing a solid support comprising activated carboxylic acid groups at its surface,
   b) providing nucleic aptamers as claimed in claim 1, comprising at least one reactive amine function, and
   c) coupling said nucleic aptamers, or said compound of formula (I), with the activated carboxylic acid groups present at the surface of said solid support under pH conditions below 5, wherein steps a) and b) may be in any order.

11. A method for obtaining an affinity support for the selective binding of factor H, comprising the following steps:
   a) providing a solid support comprising activated carboxylic acid groups at its surface,
   b) providing a compound of formula (II) as claimed in claim 7, comprising at least one reactive amine function, and
   c) coupling said compound of formula (II), with the activated carboxylic acid groups present at the surface of said solid support under pH conditions below 5, wherein steps a) and b) may be in any order.

12. A method for immobilizing a factor H on a support, comprising contacting a sample containing factor H with an affinity support as claimed in claim 8.

13. A method for purifying a factor H, comprising the following steps:
   a) contacting a sample containing a factor H with an affinity support as claimed in claim 8, in order to form complexes between (i) the nucleic aptamers immobilized on said affinity support and (ii) said factor H,
   b) releasing the factor H from the complexes formed in step a), and
   c) recovering the factor H in purified form.

14. A method for purifying a factor H, comprising the following steps:
   a) contacting a sample containing a factor H with an affinity support as claimed in claim 9, in order to form complexes between (i) the compound of formula (II) immobilized on said affinity support and (ii) said factor H,
   b) releasing the factor H from the complexes formed in step a), and
   c) recovering the factor H in purified form.

15. The method of claim 12, wherein the factor H is selected from a plasma factor H, a recombinant factor H and a transgenic factor H.

16. The method of claim 10, wherein the factor H is selected from a human factor H and a non-human factor H.

17. The method of claim 11, wherein the factor H is selected from a human factor H and a non-human factor H.

18. The nucleic aptamer of claim 1, wherein the nucleic aptamer comprises SEQ ID NO:30.

19. The affinity support of claim 8, wherein said nucleic aptamers comprise a chemically-modified nucleotide.

20. The affinity support of claim 9, wherein [APT] comprises a chemically-modified nucleotide.

* * * * *

```
                        SEQUENCE LISTING

<160> NUMBER OF SEQ ID NOS: 243

<210> SEQ ID NO 1
<211> LENGTH: 18
<212> TYPE: DNA
<213> ORGANISM: artificial sequence
<220> FEATURE:
<223> OTHER INFORMATION: aptamer

<400> SEQUENCE: 1
gggtcaatgc caggtctc                                                 18

<210> SEQ ID NO 2
<211> LENGTH: 18
<212> TYPE: DNA
<213> ORGANISM: artificial sequence
<220> FEATURE:
<223> OTHER INFORMATION: aptamer

<400> SEQUENCE: 2
atcggctcgc aagcagtc                                                 18

<210> SEQ ID NO 3
<211> LENGTH: 40
<212> TYPE: DNA
<213> ORGANISM: artificial sequence
<220> FEATURE:
<223> OTHER INFORMATION: aptamere

<400> SEQUENCE: 3
cggtctcgag atggggtctg gtggttatac gctctcagtg                         40

<210> SEQ ID NO 4
<211> LENGTH: 40
<212> TYPE: DNA
<213> ORGANISM: artificial sequence
<220> FEATURE:
<223> OTHER INFORMATION: aptamere

<400> SEQUENCE: 4
accgtcatcg agaagggtct ggtggttata cgttctcgtg                         40

<210> SEQ ID NO 5
<211> LENGTH: 40
<212> TYPE: DNA
<213> ORGANISM: artificial sequence
<220> FEATURE:
<223> OTHER INFORMATION: aptamere

<400> SEQUENCE: 5
ggaccgcgat ggagaggggt ctggtggtta tacgctatgc                         40
```

```
<210> SEQ ID NO 6
<211> LENGTH: 40
<212> TYPE: DNA
<213> ORGANISM: artificial sequence
<220> FEATURE:
<223> OTHER INFORMATION: aptamere

<400> SEQUENCE: 6
gggccgcgat ggagaggggt ctggtggtta tacgctatgt                    40

<210> SEQ ID NO 7
<211> LENGTH: 40
<212> TYPE: DNA
<213> ORGANISM: artificial sequence
<220> FEATURE:
<223> OTHER INFORMATION: aptamere

<400> SEQUENCE: 7
cggcagcaga tggacagggt caggtggtta tacgtgtggc                    40

<210> SEQ ID NO 8
<211> LENGTH: 40
<212> TYPE: DNA
<213> ORGANISM: artificial sequence
<220> FEATURE:
<223> OTHER INFORMATION: aptamere

<400> SEQUENCE: 8
gcgatgacca atagggggtca ggtggttata cgctttggat                   40

<210> SEQ ID NO 9
<211> LENGTH: 38
<212> TYPE: DNA
<213> ORGANISM: artificial sequence
<220> FEATURE:
<223> OTHER INFORMATION: aptamere

<400> SEQUENCE: 9
gggggcggcc gcagtagggg tctggtggtt atacgcgt                      38

<210> SEQ ID NO 10
<211> LENGTH: 40
<212> TYPE: DNA
<213> ORGANISM: artificial sequence
<220> FEATURE:
<223> OTHER INFORMATION: aptamere

<400> SEQUENCE: 10
gcagaggtgc gaggggcggt ggggtctggt ggttatacgc                    40

<210> SEQ ID NO 11
<211> LENGTH: 40
<212> TYPE: DNA
<213> ORGANISM: artificial sequence
<220> FEATURE:
<223> OTHER INFORMATION: aptamere

<400> SEQUENCE: 11
acgtcgagtt gtatggtggg gtcaggtggt tatacgcagc                    40

<210> SEQ ID NO 12
<211> LENGTH: 40
<212> TYPE: DNA
<213> ORGANISM: artificial sequence
<220> FEATURE:
<223> OTHER INFORMATION: aptamere
```

```
<400> SEQUENCE: 12
aaggccgaca cactgggggg tctggtggtt atacgcccgt                          40

<210> SEQ ID NO 13
<211> LENGTH: 40
<212> TYPE: DNA
<213> ORGANISM: artificial sequence
<220> FEATURE:
<223> OTHER INFORMATION: aptamere

<400> SEQUENCE: 13
gcatgatact actggggtct ggtggttata cgcaggtagg                          40

<210> SEQ ID NO 14
<211> LENGTH: 40
<212> TYPE: DNA
<213> ORGANISM: artificial sequence
<220> FEATURE:
<223> OTHER INFORMATION: aptamere

<400> SEQUENCE: 14
gaggaacgtg gggtcaggtg gttatacgca gggtaccggg                          40

<210> SEQ ID NO 15
<211> LENGTH: 40
<212> TYPE: DNA
<213> ORGANISM: artificial sequence
<220> FEATURE:
<223> OTHER INFORMATION: aptamere

<400> SEQUENCE: 15
ggcagggagg aggaatcggg acaggcggtt atacggattc                          40

<210> SEQ ID NO 16
<211> LENGTH: 40
<212> TYPE: DNA
<213> ORGANISM: artificial sequence
<220> FEATURE:
<223> OTHER INFORMATION: aptamere

<400> SEQUENCE: 16
cggaaagagt atggaacggg tcaggcggtt ataaggttac                          40

<210> SEQ ID NO 17
<211> LENGTH: 40
<212> TYPE: DNA
<213> ORGANISM: artificial sequence
<220> FEATURE:
<223> OTHER INFORMATION: aptamere

<400> SEQUENCE: 17
cacggcgtat gcgtagatcg atgggtctgg cggttatacg                          40

<210> SEQ ID NO 18
<211> LENGTH: 40
<212> TYPE: DNA
<213> ORGANISM: artificial sequence
<220> FEATURE:
<223> OTHER INFORMATION: aptamere

<400> SEQUENCE: 18
acaagagctg tattagtcgg gtctggcggt tatacggact                          40

<210> SEQ ID NO 19
<211> LENGTH: 40
```

```
<212> TYPE: DNA
<213> ORGANISM: artificial sequence
<220> FEATURE:
<223> OTHER INFORMATION: aptamere

<400> SEQUENCE: 19
agggcggatt gcggtacggt tgggtctggt ggttatacga                           40

<210> SEQ ID NO 20
<211> LENGTH: 40
<212> TYPE: DNA
<213> ORGANISM: artificial sequence
<220> FEATURE:
<223> OTHER INFORMATION: aptamere

<400> SEQUENCE: 20
tgcggagcat tacattcacg ggtctggcgg ttatacggtg                           40

<210> SEQ ID NO 21
<211> LENGTH: 40
<212> TYPE: DNA
<213> ORGANISM: artificial sequence
<220> FEATURE:
<223> OTHER INFORMATION: aptamere

<400> SEQUENCE: 21 gggggggccgg ttatacgggt caggcggtta tacggtattc                          40

<210> SEQ ID NO 22
<211> LENGTH: 40
<212> TYPE: DNA
<213> ORGANISM: artificial sequence
<220> FEATURE:
<223> OTHER INFORMATION: aptamere

<400> SEQUENCE: 22
gaggggctgg ggtcacaggg gtcggtgtgg ttattattct                           40

<210> SEQ ID NO 23
<211> LENGTH: 40
<212> TYPE: DNA
<213> ORGANISM: artificial sequence
<220> FEATURE:
<223> OTHER INFORMATION: aptamere

<400> SEQUENCE: 23
gggacaggcg gttatacgga gagttctggt gtagggttgg                           40

<210> SEQ ID NO 24
<211> LENGTH: 40
<212> TYPE: DNA
<213> ORGANISM: artificial sequence
<220> FEATURE:
<223> OTHER INFORMATION: aptamere

<400> SEQUENCE: 24
ggggcaggcg gttatacgga gagcttctta catgggccct                           40

<210> SEQ ID NO 25
<211> LENGTH: 40
<212> TYPE: DNA
<213> ORGANISM: artificial sequence
<220> FEATURE:
<223> OTHER INFORMATION: aptamere

<400> SEQUENCE: 25
```
gggtcaggcg gttatacgga gacaccttgc tgtgttaggc                          40

<210> SEQ ID NO 26
<211> LENGTH: 40
<212> TYPE: DNA
<213> ORGANISM: artificial sequence
<220> FEATURE:
<223> OTHER INFORMATION: aptamere

<400> SEQUENCE: 26
cggggcaggc ggttatacgg gagaacggta tgggggact                           40

<210> SEQ ID NO 27
<211> LENGTH: 40
<212> TYPE: DNA
<213> ORGANISM: artificial sequence
<220> FEATURE:
<223> OTHER INFORMATION: aptamere

<400> SEQUENCE: 27
cggggtctgg tggttatacg ctgagatggg tgctacagag                          40

<210> SEQ ID NO 28
<211> LENGTH: 40
<212> TYPE: DNA
<213> ORGANISM: artificial sequence
<220> FEATURE:
<223> OTHER INFORMATION: aptamere

<400> SEQUENCE: 28
accgggtcag gcggttatac gggtgggggc aggtacatac                          40

<210> SEQ ID NO 29
<211> LENGTH: 40
<212> TYPE: DNA
<213> ORGANISM: artificial sequence
<220> FEATURE:
<223> OTHER INFORMATION: aptamere

<400> SEQUENCE: 29 acagggtca gtggaagtta tagactggga aggcatacaa                           40

<210> SEQ ID NO 30
<211> LENGTH: 40
<212> TYPE: DNA
<213> ORGANISM: artificial sequence
<220> FEATURE:
<223> OTHER INFORMATION: aptamere

<400> SEQUENCE: 30
gggcacgggt caggcggtta tacggtgccc attgttcttt                          40

<210> SEQ ID NO 31
<211> LENGTH: 40
<212> TYPE: DNA
<213> ORGANISM: artificial sequence
<220> FEATURE:
<223> OTHER INFORMATION: aptamere

<400> SEQUENCE: 31
acgggtcagg cggttatacg gtgtggcttg atggtgactt                          40

<210> SEQ ID NO 32
<211> LENGTH: 40
<212> TYPE: DNA
<213> ORGANISM: artificial sequence -continued

```
<220> FEATURE:
<223> OTHER INFORMATION: aptamere

<400> SEQUENCE: 32
gggtcaggcg gttatacgga ggcctcgctg aacccagcta                              40

<210> SEQ ID NO 33
<211> LENGTH: 39
<212> TYPE: DNA
<213> ORGANISM: artificial sequence
<220> FEATURE:
<223> OTHER INFORMATION: aptamere

<400> SEQUENCE: 33
gcaacgggtc aggcggttat acggttcgta tcctggcga                               39

<210> SEQ ID NO 34
<211> LENGTH: 40
<212> TYPE: DNA
<213> ORGANISM: artificial sequence
<220> FEATURE:
<223> OTHER INFORMATION: aptamere

<400> SEQUENCE: 34
aagtggggtc tggtggttat acgcggttgt ggtgattgac                              40

<210> SEQ ID NO 35
<211> LENGTH: 40
<212> TYPE: DNA
<213> ORGANISM: artificial sequence
<220> FEATURE:
<223> OTHER INFORMATION: aptamere

<400> SEQUENCE: 35
gcgggtctgg tggttatacg tcgaatttgt taaattgcca                              40

<210> SEQ ID NO 36
<211> LENGTH: 40
<212> TYPE: DNA
<213> ORGANISM: artificial sequence
<220> FEATURE:
<223> OTHER INFORMATION: aptamere

<400> SEQUENCE: 36
aatcagaagg gtctggtggt tatacgttca tgtattgggt                              40

<210> SEQ ID NO 37
<211> LENGTH: 40
<212> TYPE: DNA
<213> ORGANISM: artificial sequence
<220> FEATURE:
<223> OTHER INFORMATION: aptamere

<400> SEQUENCE: 37
ggatggggtc aggtggttat acgctctgag tggttttggt                              40

<210> SEQ ID NO 38
<211> LENGTH: 40
<212> TYPE: DNA
<213> ORGANISM: artificial sequence
<220> FEATURE:
<223> OTHER INFORMATION: aptamere

<400> SEQUENCE: 38
ggggtgcgag ggtctggtgg ttatacgtcg tcacctctag                              40
```

<210> SEQ ID NO 39
<211> LENGTH: 40
<212> TYPE: DNA
<213> ORGANISM: artificial sequence
<220> FEATURE:
<223> OTHER INFORMATION: aptamere

<400> SEQUENCE: 39
tgggggaggg agggtctggg ggttatacgt cactagcaaa          40

<210> SEQ ID NO 40
<211> LENGTH: 40
<212> TYPE: DNA
<213> ORGANISM: artificial sequence
<220> FEATURE:
<223> OTHER INFORMATION: aptamere

<400> SEQUENCE: 40
gaggggcttt tgggagggac tggtggttat acgtcccaat          40

<210> SEQ ID NO 41
<211> LENGTH: 40
<212> TYPE: DNA
<213> ORGANISM: artificial sequence
<220> FEATURE:
<223> OTHER INFORMATION: aptamere

<400> SEQUENCE: 41
gcggtggacg gggctggcgg ttatacggtc cttacgcggt          40

<210> SEQ ID NO 42
<211> LENGTH: 40
<212> TYPE: DNA
<213> ORGANISM: artificial sequence
<220> FEATURE:
<223> OTHER INFORMATION: aptamere

<400> SEQUENCE: 42
gcggctgtgg ggtctggtgg ttatacgcac atacgcgctg          40

<210> SEQ ID NO 43
<211> LENGTH: 40
<212> TYPE: DNA
<213> ORGANISM: artificial sequence
<220> FEATURE:
<223> OTHER INFORMATION: aptamere

<400> SEQUENCE: 43
ccggttaccg cgctaagctt ggcgatggtg ttagtggctg          40

<210> SEQ ID NO 44
<211> LENGTH: 40
<212> TYPE: DNA
<213> ORGANISM: artificial sequence
<220> FEATURE:
<223> OTHER INFORMATION: aptamere

<400> SEQUENCE: 44
ccggttaccg ttacgttgga cgaggaatgg tgttcgtggc          40

<210> SEQ ID NO 45
<211> LENGTH: 40
<212> TYPE: DNA
<213> ORGANISM: artificial sequence
<220> FEATURE:
<223> OTHER INFORMATION: aptamere

```
<400> SEQUENCE: 45
ccggttactg ccgtagttgt cttacggtgg tgttagtggc                           40

<210> SEQ ID NO 46
<211> LENGTH: 40
<212> TYPE: DNA
<213> ORGANISM: artificial sequence
<220> FEATURE:
<223> OTHER INFORMATION: aptamere

<400> SEQUENCE: 46
ccggttactt ccgtagctgt cttacggtgg tgttagtggc                           40

<210> SEQ ID NO 47
<211> LENGTH: 40
<212> TYPE: DNA
<213> ORGANISM: artificial sequence
<220> FEATURE:
<223> OTHER INFORMATION: aptamere

<400> SEQUENCE: 47
ccggttaccg cattagtggt gtttgtggcg ttgagatggc                           40

<210> SEQ ID NO 48
<211> LENGTH: 40
<212> TYPE: DNA
<213> ORGANISM: artificial sequence
<220> FEATURE:
<223> OTHER INFORMATION: aptamere

<400> SEQUENCE: 48
ccggttacct ccattggtgg tgttagtggc tttgtaggat                           40

<210> SEQ ID NO 49
<211> LENGTH: 40
<212> TYPE: DNA
<213> ORGANISM: artificial sequence
<220> FEATURE:
<223> OTHER INFORMATION: aptamere

<400> SEQUENCE: 49
ccggttacca gttggtgttt gtggctttgc acgtctgcat                           40

<210> SEQ ID NO 50
<211> LENGTH: 40
<212> TYPE: DNA
<213> ORGANISM: artificial sequence
<220> FEATURE:
<223> OTHER INFORMATION: aptamere

<400> SEQUENCE: 50
ccggttacca gttggtgttt gtggctttgc acgtgtgcat                           40

<210> SEQ ID NO 51
<211> LENGTH: 43
<212> TYPE: DNA
<213> ORGANISM: artificial sequence
<220> FEATURE:
<223> OTHER INFORMATION: aptamere

<400> SEQUENCE: 51
ccggttacca gttggtgttg ttagtggctt tgcacgtctg cat                       43

<210> SEQ ID NO 52
```

```
<211> LENGTH: 40
<212> TYPE: DNA
<213> ORGANISM: artificial sequence
<220> FEATURE:
<223> OTHER INFORMATION: aptamere

<400> SEQUENCE: 52
ccggttacca actatggtgt tagtggcatc gatcgggatc                              40

<210> SEQ ID NO 53
<211> LENGTH: 38
<212> TYPE: DNA
<213> ORGANISM: artificial sequence
<220> FEATURE:
<223> OTHER INFORMATION: aptamere

<400> SEQUENCE: 53
ccggttacct ttggtgtttg tggcatgggc gtcggggc                                38

<210> SEQ ID NO 54
<211> LENGTH: 40
<212> TYPE: DNA
<213> ORGANISM: artificial sequence
<220> FEATURE:
<223> OTHER INFORMATION: aptamere

<400> SEQUENCE: 54
ccggttaccg tttggtgttt gtggctgtga cttggatacc                              40

<210> SEQ ID NO 55
<211> LENGTH: 40
<212> TYPE: DNA
<213> ORGANISM: artificial sequence
<220> FEATURE:
<223> OTHER INFORMATION: aptamere

<400> SEQUENCE: 55
ccggttacca cattggtgtt tgtggcagtg ttattccccg                              40

<210> SEQ ID NO 56
<211> LENGTH: 38
<212> TYPE: DNA
<213> ORGANISM: artificial sequence
<220> FEATURE:
<223> OTHER INFORMATION: aptamere

<400> SEQUENCE: 56
ccggttacca actatgatag tatggtgttt gtggcatg                                38

<210> SEQ ID NO 57
<211> LENGTH: 38
<212> TYPE: DNA
<213> ORGANISM: artificial sequence
<220> FEATURE:
<223> OTHER INFORMATION: aptamere

<400> SEQUENCE: 57
ccggttacca actatgatag tatggtgttt gtggcgtg                                38

<210> SEQ ID NO 58
<211> LENGTH: 40
<212> TYPE: DNA
<213> ORGANISM: artificial sequence
<220> FEATURE:
<223> OTHER INFORMATION: aptamere

<400> SEQUENCE: 58
```

```
ccggttacca tcgaggacgt cgcttggtgt ttgtggcatg                            40

<210> SEQ ID NO 59
<211> LENGTH: 40
<212> TYPE: DNA
<213> ORGANISM: artificial sequence
<220> FEATURE:
<223> OTHER INFORMATION: aptamere

<400> SEQUENCE: 59
ccggttacca agatcgttgt tcttggtgtt agtggcattc                            40

<210> SEQ ID NO 60
<211> LENGTH: 40
<212> TYPE: DNA
<213> ORGANISM: artificial sequence
<220> FEATURE:
<223> OTHER INFORMATION: aptamere

<400> SEQUENCE: 60
ccggttaccc agtctcctgc ggtgtttgtg gcatagggca                            40

<210> SEQ ID NO 61
<211> LENGTH: 40
<212> TYPE: DNA
<213> ORGANISM: artificial sequence
<220> FEATURE:
<223> OTHER INFORMATION: aptamere

<400> SEQUENCE: 61
tgaggcgcag atgtggaggc ttttacaggc ggtgcggaac                            40

<210> SEQ ID NO 62
<211> LENGTH: 40
<212> TYPE: DNA
<213> ORGANISM: artificial sequence
<220> FEATURE:
<223> OTHER INFORMATION: aptamere

<400> SEQUENCE: 62
tgaggcgcag atgtggaggc ttttaccggc ggtgcggaac                            40

<210> SEQ ID NO 63
<211> LENGTH: 40
<212> TYPE: DNA
<213> ORGANISM: artificial sequence
<220> FEATURE:
<223> OTHER INFORMATION: aptamere

<400> SEQUENCE: 63
tggggcgcag atgtggaggc ttttacaggc ggtgcggaac                            40

<210> SEQ ID NO 64
<211> LENGTH: 40
<212> TYPE: DNA
<213> ORGANISM: artificial sequence
<220> FEATURE:
<223> OTHER INFORMATION: aptamere

<400> SEQUENCE: 64 gggggggggcg gtgccgggag gctttcatca ggctgtgcgt                           40

<210> SEQ ID NO 65
<211> LENGTH: 40
<212> TYPE: DNA
```

```
<213> ORGANISM: artificial sequence
<220> FEATURE:
<223> OTHER INFORMATION: aptamere

<400> SEQUENCE: 65 caaaggggggg ggttgggggga ccgtccgttg ttgatctcac                    40

<210> SEQ ID NO 66
<211> LENGTH: 40
<212> TYPE: DNA
<213> ORGANISM: artificial sequence
<220> FEATURE:
<223> OTHER INFORMATION: aptamere

<400> SEQUENCE: 66 ccagggggggg ggtgatatag gggaccgtcc gtattggtag                     40

<210> SEQ ID NO 67
<211> LENGTH: 40
<212> TYPE: DNA
<213> ORGANISM: artificial sequence
<220> FEATURE:
<223> OTHER INFORMATION: aptamere

<400> SEQUENCE: 67
ggcgaattgg ttctgtgggg ggttggggcg gcaattcgat                      40

<210> SEQ ID NO 68
<211> LENGTH: 41
<212> TYPE: DNA
<213> ORGANISM: artificial sequence
<220> FEATURE:
<223> OTHER INFORMATION: aptamere

<400> SEQUENCE: 68
gagcgtgcca aagggttttg tgggggggt ggggcggcaa a                     41

<210> SEQ ID NO 69
<211> LENGTH: 40
<212> TYPE: DNA
<213> ORGANISM: artificial sequence
<220> FEATURE:
<223> OTHER INFORMATION: aptamere

<400> SEQUENCE: 69
ttgccatgtg gtctttgtgg gttcgggtta gggtagggtt                      40

<210> SEQ ID NO 70
<211> LENGTH: 39
<212> TYPE: DNA
<213> ORGANISM: artificial sequence
<220> FEATURE:
<223> OTHER INFORMATION: aptamere

<400> SEQUENCE: 70 gttgttctttt gtgggtgcgg gttagggtag ggggattag                      39

<210> SEQ ID NO 71
<211> LENGTH: 40
<212> TYPE: DNA
<213> ORGANISM: artificial sequence
<220> FEATURE:
<223> OTHER INFORMATION: aptamere

<400> SEQUENCE: 71
ggcaaaccgt cttagtgggt gtggggttag ggttgggggt                      40
```

<210> SEQ ID NO 72
<211> LENGTH: 40
<212> TYPE: DNA
<213> ORGANISM: artificial sequence
<220> FEATURE:
<223> OTHER INFORMATION: aptamere

<400> SEQUENCE: 72
ggctgcaagg gattggatca gatacggggg ggacagctcg        40

<210> SEQ ID NO 73
<211> LENGTH: 40
<212> TYPE: DNA
<213> ORGANISM: artificial sequence
<220> FEATURE:
<223> OTHER INFORMATION: aptamere

<400> SEQUENCE: 73
ggcatgcgga ccaccaatca gcccgggcgt cgggcggcca        40

<210> SEQ ID NO 74
<211> LENGTH: 40
<212> TYPE: DNA
<213> ORGANISM: artificial sequence
<220> FEATURE:
<223> OTHER INFORMATION: aptamere

<400> SEQUENCE: 74
cgcaggaagg ccggaggtta taacggcaac tcttcagcca        40

<210> SEQ ID NO 75
<211> LENGTH: 40
<212> TYPE: DNA
<213> ORGANISM: artificial sequence
<220> FEATURE:
<223> OTHER INFORMATION: aptamere

<400> SEQUENCE: 75
tatgccccat cccgcgaaca ccgtcagtaa cgcaactgtt        40

<210> SEQ ID NO 76
<211> LENGTH: 40
<212> TYPE: DNA
<213> ORGANISM: artificial sequence
<220> FEATURE:
<223> OTHER INFORMATION: aptamere

<400> SEQUENCE: 76
cgcgctcggt ctagggaata cggccgccca attcgttacc        40

<210> SEQ ID NO 77
<211> LENGTH: 40
<212> TYPE: DNA
<213> ORGANISM: artificial sequence
<220> FEATURE:
<223> OTHER INFORMATION: aptamere

<400> SEQUENCE: 77
ggtgggaggt gaggtcgttg gacggtggca ggggattttg        40

<210> SEQ ID NO 78
<211> LENGTH: 40
<212> TYPE: DNA
<213> ORGANISM: artificial sequence
<220> FEATURE:

```
<223> OTHER INFORMATION: aptamere

<400> SEQUENCE: 78
gtggaggggt tgggcgtggc ccaggggagg gtggcttgtt                              40

<210> SEQ ID NO 79
<211> LENGTH: 40
<212> TYPE: DNA
<213> ORGANISM: artificial sequence
<220> FEATURE:
<223> OTHER INFORMATION: aptamere

<400> SEQUENCE: 79
tgcgttgggg gggtgcgcgg gggcaacgtg gcacgtgagg                              40

<210> SEQ ID NO 80
<211> LENGTH: 40
<212> TYPE: DNA
<213> ORGANISM: artificial sequence
<220> FEATURE:
<223> OTHER INFORMATION: aptamere

<400> SEQUENCE: 80
gtggtacgcg tattggcggt agtggagttt gaggcacgag                              40

<210> SEQ ID NO 81
<211> LENGTH: 40
<212> TYPE: DNA
<213> ORGANISM: artificial sequence
<220> FEATURE:
<223> OTHER INFORMATION: aptamere

<400> SEQUENCE: 81
gtgctgctgt agtaggccat gtggagggtt ccagggaggt                              40

<210> SEQ ID NO 82
<211> LENGTH: 40
<212> TYPE: DNA
<213> ORGANISM: artificial sequence
<220> FEATURE:
<223> OTHER INFORMATION: aptamere

<400> SEQUENCE: 82
gggggactgg agggtatacg ccgaggaggt tcggggttg                               40

<210> SEQ ID NO 83
<211> LENGTH: 40
<212> TYPE: DNA
<213> ORGANISM: artificial sequence
<220> FEATURE:
<223> OTHER INFORMATION: aptamere

<400> SEQUENCE: 83
acgtggaggg tgccagggag gtgtgagaat aggacgcgct                              40

<210> SEQ ID NO 84
<211> LENGTH: 40
<212> TYPE: DNA
<213> ORGANISM: artificial sequence
<220> FEATURE:
<223> OTHER INFORMATION: aptamere

<400> SEQUENCE: 84
accggggaga aggagccgga cctggggcgc gcgggcgtcg                              40
```

```
<210> SEQ ID NO 85
<211> LENGTH: 40
<212> TYPE: DNA
<213> ORGANISM: artificial sequence
<220> FEATURE:
<223> OTHER INFORMATION: aptamere

<400> SEQUENCE: 85
gggtccaggg catcctgcgt aggtggcggg cttatgttac                     40

<210> SEQ ID NO 86
<211> LENGTH: 40
<212> TYPE: DNA
<213> ORGANISM: artificial sequence
<220> FEATURE:
<223> OTHER INFORMATION: aptamere

<400> SEQUENCE: 86
gggcagccct ccttctcagt cggtgttggt gatgtgacta                     40

<210> SEQ ID NO 87
<211> LENGTH: 40
<212> TYPE: DNA
<213> ORGANISM: artificial sequence
<220> FEATURE:
<223> OTHER INFORMATION: aptamere

<400> SEQUENCE: 87
tggccccgat gtcctggtaa gatggatggt ctgggatggt                     40

<210> SEQ ID NO 88
<211> LENGTH: 40
<212> TYPE: DNA
<213> ORGANISM: artificial sequence
<220> FEATURE:
<223> OTHER INFORMATION: aptamere

<400> SEQUENCE: 88
cctgccgcgg tgtgtgggtt attctggtta ttttggtggc                     40

<210> SEQ ID NO 89
<211> LENGTH: 40
<212> TYPE: DNA
<213> ORGANISM: artificial sequence
<220> FEATURE:
<223> OTHER INFORMATION: aptamere

<400> SEQUENCE: 89
ggccgggcgg gtgtgggggg tactgagggt aagtagcggc                     40

<210> SEQ ID NO 90
<211> LENGTH: 40
<212> TYPE: DNA
<213> ORGANISM: artificial sequence
<220> FEATURE:
<223> OTHER INFORMATION: aptamere

<400> SEQUENCE: 90
gcggtggccg acggttacct atggtgttag ttgtagaaca                     40

<210> SEQ ID NO 91
<211> LENGTH: 40
<212> TYPE: DNA
<213> ORGANISM: artificial sequence
<220> FEATURE:
<223> OTHER INFORMATION: aptamere
```

<400> SEQUENCE: 91
ggattcaggt ggccgaacgg tgttgtgttg agtacggtgg                              40

<210> SEQ ID NO 92
<211> LENGTH: 39
<212> TYPE: DNA
<213> ORGANISM: artificial sequence
<220> FEATURE:
<223> OTHER INFORMATION: aptamere

<400> SEQUENCE: 92
caagggagcg agagttggcg cgtctacaca taccctgac                               39

<210> SEQ ID NO 93
<211> LENGTH: 40
<212> TYPE: DNA
<213> ORGANISM: artificial sequence
<220> FEATURE:
<223> OTHER INFORMATION: aptamere

<400> SEQUENCE: 93
ggacgcaggg gtggacgcta taagccatgg atagttcagt                              40

<210> SEQ ID NO 94
<211> LENGTH: 40
<212> TYPE: DNA
<213> ORGANISM: artificial sequence
<220> FEATURE:
<223> OTHER INFORMATION: aptamere

<400> SEQUENCE: 94
gtcgacacgg gggggatatc gctatcgcaa tctgatcgct                              40

<210> SEQ ID NO 95
<211> LENGTH: 40
<212> TYPE: DNA
<213> ORGANISM: artificial sequence
<220> FEATURE:
<223> OTHER INFORMATION: aptamere

<400> SEQUENCE: 95
aaggcggggc ggtactgtac tctcgtaata ctgttccccg                              40

<210> SEQ ID NO 96
<211> LENGTH: 40
<212> TYPE: DNA
<213> ORGANISM: artificial sequence
<220> FEATURE:
<223> OTHER INFORMATION: aptamere

<400> SEQUENCE: 96
caaagggggg ggttggggga ccgtccgttg ttgatctcac                              40

<210> SEQ ID NO 97
<211> LENGTH: 40
<212> TYPE: DNA
<213> ORGANISM: artificial sequence
<220> FEATURE:
<223> OTHER INFORMATION: aptamere

<400> SEQUENCE: 97
ccaggggggg ggtgatatag gggaccgtcc gtattggtag                              40

<210> SEQ ID NO 98
<211> LENGTH: 40

<212> TYPE: DNA
<213> ORGANISM: artificial sequence
<220> FEATURE:
<223> OTHER INFORMATION: aptamere

<400> SEQUENCE: 98
tatgggtgca cttgtcacgt accttgggac tttcaagggt                              40

<210> SEQ ID NO 99
<211> LENGTH: 40
<212> TYPE: DNA
<213> ORGANISM: artificial sequence
<220> FEATURE:
<223> OTHER INFORMATION: aptamere

<400> SEQUENCE: 99 gggggaata gtcaagtatt gagcgggact ttcgttgccc                               40

<210> SEQ ID NO 100
<211> LENGTH: 40
<212> TYPE: DNA
<213> ORGANISM: artificial sequence
<220> FEATURE:
<223> OTHER INFORMATION: aptamere

<400> SEQUENCE: 100
acgggggtat aatgttcatt gaatcaggcc gcccgtgtgt                              40

<210> SEQ ID NO 101
<211> LENGTH: 40
<212> TYPE: DNA
<213> ORGANISM: artificial sequence
<220> FEATURE:
<223> OTHER INFORMATION: aptamere

<400> SEQUENCE: 101
acgcggggat aaaagtctgt ctattggtga aggcacgcca                              40

<210> SEQ ID NO 102
<211> LENGTH: 40
<212> TYPE: DNA
<213> ORGANISM: artificial sequence
<220> FEATURE:
<223> OTHER INFORMATION: aptamere

<400> SEQUENCE: 102
cgggcggtag aagttggctc gtcggttagg tgggaagggt                              40

<210> SEQ ID NO 103
<211> LENGTH: 40
<212> TYPE: DNA
<213> ORGANISM: artificial sequence
<220> FEATURE:
<223> OTHER INFORMATION: aptamere

<400> SEQUENCE: 103
cactggcgaa gagacgttgg cttcgttgcg gcggcccagt                              40

<210> SEQ ID NO 104
<211> LENGTH: 40
<212> TYPE: DNA
<213> ORGANISM: artificial sequence
<220> FEATURE:
<223> OTHER INFORMATION: aptamere

<400> SEQUENCE: 104

```
gtcgtggtgc cgaagggaga cgaattcgat tgccggtggc                                    40
```

<210> SEQ ID NO 105
<211> LENGTH: 40
<212> TYPE: DNA
<213> ORGANISM: artificial sequence
<220> FEATURE:
<223> OTHER INFORMATION: aptamere

<400> SEQUENCE: 105

```
gggcggtgga agtggggaga aagtgggtat tgtggccagt                                    40
```

<210> SEQ ID NO 106
<211> LENGTH: 40
<212> TYPE: DNA
<213> ORGANISM: artificial sequence
<220> FEATURE:
<223> OTHER INFORMATION: aptamere

<400> SEQUENCE: 106

```
ggcagaacgg gacatattgg aatgcctctg tgtgtttagt                                    40
```

<210> SEQ ID NO 107
<211> LENGTH: 40
<212> TYPE: DNA
<213> ORGANISM: artificial sequence
<220> FEATURE:
<223> OTHER INFORMATION: aptamere

<400> SEQUENCE: 107

```
ctgaacggtg gaattatgtc ggtgcgtgta cctattcggg                                    40
```

<210> SEQ ID NO 108
<211> LENGTH: 40
<212> TYPE: DNA
<213> ORGANISM: artificial sequence
<220> FEATURE:
<223> OTHER INFORMATION: aptamere

<400> SEQUENCE: 108

```
ggacaccagc acgtagggga gtatatatca atgggggct                                     40
```

<210> SEQ ID NO 109
<211> LENGTH: 40
<212> TYPE: DNA
<213> ORGANISM: artificial sequence
<220> FEATURE:
<223> OTHER INFORMATION: aptamere

<400> SEQUENCE: 109

```
cgacgcgaga gccagggcgc ggtgtcttct tgtggggtag                                    40
```

<210> SEQ ID NO 110
<211> LENGTH: 40
<212> TYPE: DNA
<213> ORGANISM: artificial sequence
<220> FEATURE:
<223> OTHER INFORMATION: aptamere

<400> SEQUENCE: 110

```
tgtgagcgca gcactgtgta cccccctatt gttatctgga                                    40
```

<210> SEQ ID NO 111
<211> LENGTH: 40
<212> TYPE: DNA
<213> ORGANISM: artificial sequence

```
<220> FEATURE:
<223> OTHER INFORMATION: aptamere

<400> SEQUENCE: 111
gggattttga cgcgcacgtg ggaccacccc tgcctagttc                            40

<210> SEQ ID NO 112
<211> LENGTH: 40
<212> TYPE: DNA
<213> ORGANISM: artificial sequence
<220> FEATURE:
<223> OTHER INFORMATION: aptamere

<400> SEQUENCE: 112
aaacccgatc cacgccccct gtagtgatcc taagatgatc                            40

<210> SEQ ID NO 113
<211> LENGTH: 40
<212> TYPE: DNA
<213> ORGANISM: artificial sequence
<220> FEATURE:
<223> OTHER INFORMATION: aptamere

<400> SEQUENCE: 113
aacgccccgc ccactatgcg ccgtatatgg accagatcct                            40

<210> SEQ ID NO 114
<211> LENGTH: 40
<212> TYPE: DNA
<213> ORGANISM: artificial sequence
<220> FEATURE:
<223> OTHER INFORMATION: aptamere

<400> SEQUENCE: 114
agcacccggg gcctgaaaga aggcgaggta atatggactt                            40

<210> SEQ ID NO 115
<211> LENGTH: 40
<212> TYPE: DNA
<213> ORGANISM: artificial sequence
<220> FEATURE:
<223> OTHER INFORMATION: aptamere

<400> SEQUENCE: 115
caccgcctga acgaacaaga aagcgagaac caggagctac                            40

<210> SEQ ID NO 116
<211> LENGTH: 39
<212> TYPE: DNA
<213> ORGANISM: artificial sequence
<220> FEATURE:
<223> OTHER INFORMATION: aptamere

<400> SEQUENCE: 116
gctgcgcgct tctgatgtac tgaaggggtc cgggagtac                             39

<210> SEQ ID NO 117
<211> LENGTH: 76
<212> TYPE: DNA
<213> ORGANISM: artificial sequence
<220> FEATURE:
<223> OTHER INFORMATION: aptamere

<400> SEQUENCE: 117
gggtcaatgc caggtctccg gtctcgagat ggggtctggt ggttatacgc tctcagtgat      60
```

```
<210> SEQ ID NO 118
<211> LENGTH: 76
<212> TYPE: DNA
<213> ORGANISM: artificial sequence
<220> FEATURE:
<223> OTHER INFORMATION: aptamere

<400> SEQUENCE: 118
gggtcaatgc caggtctcac cgtcatcgag aagggtctgg tggttatacg ttctcgtgat    60
cggctcgcaa gcagtc                                                   76

<210> SEQ ID NO 119
<211> LENGTH: 76
<212> TYPE: DNA
<213> ORGANISM: artificial sequence
<220> FEATURE:
<223> OTHER INFORMATION: aptamere

<400> SEQUENCE: 119
gggtcaatgc caggtctcgg accgcgatgg agagggtct ggtggttata cgctatgcat     60
cggctcgcaa gcagtc                                                   76

<210> SEQ ID NO 120
<211> LENGTH: 76
<212> TYPE: DNA
<213> ORGANISM: artificial sequence
<220> FEATURE:
<223> OTHER INFORMATION: aptamere

<400> SEQUENCE: 120
gggtcaatgc caggtctcgg gccgcgatgg agagggtct ggtggttata cgctatgtat    60
cggctcgcaa gcagtc                                                   76

<210> SEQ ID NO 121
<211> LENGTH: 76
<212> TYPE: DNA
<213> ORGANISM: artificial sequence
<220> FEATURE:
<223> OTHER INFORMATION: aptamere

<400> SEQUENCE: 121
gggtcaatgc caggtctccg gcagcagatg gacagggtca ggtggttata cgtgtggcat    60
cggctcgcaa gcagtc                                                   76

<210> SEQ ID NO 122
<211> LENGTH: 76
<212> TYPE: DNA
<213> ORGANISM: artificial sequence
<220> FEATURE:
<223> OTHER INFORMATION: aptamere

<400> SEQUENCE: 122
gggtcaatgc caggtctcgc gatgaccaat aggggtcagg tggttatacg ctttggatat    60
cggctcgcaa gcagtc                                                   76

<210> SEQ ID NO 123
<211> LENGTH: 74
<212> TYPE: DNA
<213> ORGANISM: artificial sequence
<220> FEATURE:
<223> OTHER INFORMATION: aptamere
```

<400> SEQUENCE: 123
gggtcaatgc caggtctcgg gggcggccgc agtaggggtc tggtggttat acgcgtatcg    60
gctcgcaagc agtc                                                     74

<210> SEQ ID NO 124
<211> LENGTH: 76
<212> TYPE: DNA
<213> ORGANISM: artificial sequence
<220> FEATURE:
<223> OTHER INFORMATION: aptamere

<400> SEQUENCE: 124
gggtcaatgc caggtctcgc agaggtgcga ggggcggtgg ggtctggtgg ttatacgcat    60
cggctcgcaa gcagtc                                                   76

<210> SEQ ID NO 125
<211> LENGTH: 76
<212> TYPE: DNA
<213> ORGANISM: artificial sequence
<220> FEATURE:
<223> OTHER INFORMATION: aptamere

<400> SEQUENCE: 125
gggtcaatgc caggtctcac gtcgagttgt atggtggggt caggtggtta tacgcagcat    60
cggctcgcaa gcagtc                                                   76

<210> SEQ ID NO 126
<211> LENGTH: 76
<212> TYPE: DNA
<213> ORGANISM: artificial sequence
<220> FEATURE:
<223> OTHER INFORMATION: aptamere

<400> SEQUENCE: 126
gggtcaatgc caggtctcaa ggccgacaca ctgggggtc tggtggttat acgcccgtat     60
cggctcgcaa gcagtc                                                   76

<210> SEQ ID NO 127
<211> LENGTH: 76
<212> TYPE: DNA
<213> ORGANISM: artificial sequence
<220> FEATURE:
<223> OTHER INFORMATION: aptamere

<400> SEQUENCE: 127
gggtcaatgc caggtctcgc atgatactac tggggtctgg tggttatacg caggtaggat    60
cggctcgcaa gcagtc                                                   76

<210> SEQ ID NO 128
<211> LENGTH: 76
<212> TYPE: DNA
<213> ORGANISM: artificial sequence
<220> FEATURE:
<223> OTHER INFORMATION: aptamere

<400> SEQUENCE: 128
gggtcaatgc caggtctcga ggaacgtggg gtcaggtggt tatacgcagg gtaccgggat    60
cggctcgcaa gcagtc                                                   76

<210> SEQ ID NO 129

```
<211> LENGTH: 76
<212> TYPE: DNA
<213> ORGANISM: artificial sequence
<220> FEATURE:
<223> OTHER INFORMATION: aptamere

<400> SEQUENCE: 129
gggtcaatgc caggtctcgg cagggaggag gaatcgggac aggcggttat acggattcat    60
cggctcgcaa gcagtc                                                    76

<210> SEQ ID NO 130
<211> LENGTH: 76
<212> TYPE: DNA
<213> ORGANISM: artificial sequence
<220> FEATURE:
<223> OTHER INFORMATION: aptamere

<400> SEQUENCE: 130
gggtcaatgc caggtctccg gaaagagtat ggaacgggtc aggcggttat aaggttacat    60
cggctcgcaa gcagtc                                                    76

<210> SEQ ID NO 131
<211> LENGTH: 76
<212> TYPE: DNA
<213> ORGANISM: artificial sequence
<220> FEATURE:
<223> OTHER INFORMATION: aptamere

<400> SEQUENCE: 131
gggtcaatgc caggtctcca cggcgtatgc gtagatcgat gggtctggcg gttatacgat    60
cggctcgcaa gcagtc                                                    76

<210> SEQ ID NO 132
<211> LENGTH: 76
<212> TYPE: DNA
<213> ORGANISM: artificial sequence
<220> FEATURE:
<223> OTHER INFORMATION: aptamere

<400> SEQUENCE: 132
gggtcaatgc caggtctcac aagagctgta ttagtcgggt ctggcggtta tacggactat    60
cggctcgcaa gcagtc                                                    76

<210> SEQ ID NO 133
<211> LENGTH: 76
<212> TYPE: DNA
<213> ORGANISM: artificial sequence
<220> FEATURE:
<223> OTHER INFORMATION: aptamere

<400> SEQUENCE: 133
gggtcaatgc caggtctcag ggcggattgc ggtacggttg ggtctggtgg ttatacgaat    60
cggctcgcaa gcagtc                                                    76

<210> SEQ ID NO 134
<211> LENGTH: 76
<212> TYPE: DNA
<213> ORGANISM: artificial sequence
<220> FEATURE:
<223> OTHER INFORMATION: aptamere

<400> SEQUENCE: 134
gggtcaatgc caggtctctg cggagcatta cattcacggg tctggcggtt atacggtgat    60
```

```
cggctcgcaa gcagtc                                              76

<210> SEQ ID NO 135
<211> LENGTH: 76
<212> TYPE: DNA
<213> ORGANISM: artificial sequence
<220> FEATURE:
<223> OTHER INFORMATION: aptamere

<400> SEQUENCE: 135
gggtcaatgc caggtctcgg ggggccggtt atacgggtca ggcggttata cggtattcat    60
cggctcgcaa gcagtc                                              76

<210> SEQ ID NO 136
<211> LENGTH: 76
<212> TYPE: DNA
<213> ORGANISM: artificial sequence
<220> FEATURE:
<223> OTHER INFORMATION: aptamere

<400> SEQUENCE: 136
gggtcaatgc caggtctcga ggggctgggg tcacaggggt cggtgtggtt attattctat    60
cggctcgcaa gcagtc                                              76

<210> SEQ ID NO 137
<211> LENGTH: 76
<212> TYPE: DNA
<213> ORGANISM: artificial sequence
<220> FEATURE:
<223> OTHER INFORMATION: aptamere

<400> SEQUENCE: 137
gggtcaatgc caggtctcgg gacaggcggt tatacggaga gttctggtgt agggttggat    60
cggctcgcaa gcagtc                                              76

<210> SEQ ID NO 138
<211> LENGTH: 76
<212> TYPE: DNA
<213> ORGANISM: artificial sequence
<220> FEATURE:
<223> OTHER INFORMATION: aptamere

<400> SEQUENCE: 138
gggtcaatgc caggtctcgg ggcaggcggt tatacggaga gcttcttaca tgggccctat    60
cggctcgcaa gcagtc                                              76

<210> SEQ ID NO 139
<211> LENGTH: 76
<212> TYPE: DNA
<213> ORGANISM: artificial sequence
<220> FEATURE:
<223> OTHER INFORMATION: aptamere

<400> SEQUENCE: 139
gggtcaatgc caggtctcgg gtcaggcggt tatacggaga caccttgctg tgttaggcat    60
cggctcgcaa gcagtc                                              76

<210> SEQ ID NO 140
<211> LENGTH: 76
<212> TYPE: DNA
<213> ORGANISM: artificial sequence
<220> FEATURE:
```

<223> OTHER INFORMATION: aptamere

<400> SEQUENCE: 140
gggtcaatgc caggtctccg gggcaggcgg ttatacggga aacggtatg gggggactat    60 cggctcgcaa gcagtc    76

<210> SEQ ID NO 141
<211> LENGTH: 76
<212> TYPE: DNA
<213> ORGANISM: artificial sequence
<220> FEATURE:
<223> OTHER INFORMATION: aptamere

<400> SEQUENCE: 141
gggtcaatgc caggtctccg gggtctggtg gttatacgct gagatgggtg ctacagagat    60
cggctcgcaa gcagtc    76

<210> SEQ ID NO 142
<211> LENGTH: 76
<212> TYPE: DNA
<213> ORGANISM: artificial sequence
<220> FEATURE:
<223> OTHER INFORMATION: aptamere

<400> SEQUENCE: 142
gggtcaatgc caggtctcac cgggtcaggc ggttatacgg gtgggggcag gtacatacat    60
cggctcgcaa gcagtc    76

<210> SEQ ID NO 143
<211> LENGTH: 76
<212> TYPE: DNA
<213> ORGANISM: artificial sequence
<220> FEATURE:
<223> OTHER INFORMATION: aptamere

<400> SEQUENCE: 143
gggtcaatgc caggtctcac aggggtcagt ggaagttata gactgggaag gcatacaaat    60
cggctcgcaa gcagtc    76

<210> SEQ ID NO 144
<211> LENGTH: 76
<212> TYPE: DNA
<213> ORGANISM: artificial sequence
<220> FEATURE:
<223> OTHER INFORMATION: aptamere

<400> SEQUENCE: 144
gggtcaatgc caggtctcgg gcacgggtca ggcggttata cggtgcccat tgttctttat    60
cggctcgcaa gcagtc    76

<210> SEQ ID NO 145
<211> LENGTH: 76
<212> TYPE: DNA
<213> ORGANISM: artificial sequence
<220> FEATURE:
<223> OTHER INFORMATION: aptamere

<400> SEQUENCE: 145
gggtcaatgc caggtctcac gggtcaggcg gttatacggt gtggcttgat ggtgacttat    60
cggctcgcaa gcagtc    76

```
<210> SEQ ID NO 146
<211> LENGTH: 76
<212> TYPE: DNA
<213> ORGANISM: artificial sequence
<220> FEATURE:
<223> OTHER INFORMATION: aptamere

<400> SEQUENCE: 146
gggtcaatgc caggtctcgg gtcaggcggt tatacggagg cctcgctgaa cccagctaat    60
cggctcgcaa gcagtc                                                    76

<210> SEQ ID NO 147
<211> LENGTH: 75
<212> TYPE: DNA
<213> ORGANISM: artificial sequence
<220> FEATURE:
<223> OTHER INFORMATION: aptamere

<400> SEQUENCE: 147
gggtcaatgc caggtctcgc aacgggtcag gcggttatac ggttcgtatc ctggcgaatc    60
ggctcgcaag cagtc                                                     75

<210> SEQ ID NO 148
<211> LENGTH: 76
<212> TYPE: DNA
<213> ORGANISM: artificial sequence
<220> FEATURE:
<223> OTHER INFORMATION: aptamere

<400> SEQUENCE: 148
gggtcaatgc caggtctcaa gtggggtctg gtggttatac gcggttgtgg tgattgacat    60
cggctcgcaa gcagtc                                                    76

<210> SEQ ID NO 149
<211> LENGTH: 76
<212> TYPE: DNA
<213> ORGANISM: artificial sequence
<220> FEATURE:
<223> OTHER INFORMATION: aptamere

<400> SEQUENCE: 149
gggtcaatgc caggtctcgc gggtctggtg gttatacgtc gaatttgtta aattgccaat    60
cggctcgcaa gcagtc                                                    76

<210> SEQ ID NO 150
<211> LENGTH: 76
<212> TYPE: DNA
<213> ORGANISM: artificial sequence
<220> FEATURE:
<223> OTHER INFORMATION: aptamere

<400> SEQUENCE: 150
gggtcaatgc caggtctcaa tcagaagggt ctggtggtta tacgttcatg tattgggtat    60
cggctcgcaa gcagtc                                                    76

<210> SEQ ID NO 151
<211> LENGTH: 76
<212> TYPE: DNA
<213> ORGANISM: artificial sequence
<220> FEATURE:
<223> OTHER INFORMATION: aptamere

<400> SEQUENCE: 151
```

```
gggtcaatgc caggtctcgg atggggtcag gtggttatac gctctgagtg gttttggtat    60
cggctcgcaa gcagtc                                                    76
```

<210> SEQ ID NO 152
<211> LENGTH: 76
<212> TYPE: DNA
<213> ORGANISM: artificial sequence
<220> FEATURE:
<223> OTHER INFORMATION: aptamere

<400> SEQUENCE: 152

```
gggtcaatgc caggtctcgg ggtgcgaggg tctggtggtt atacgtcgtc acctctagat    60
cggctcgcaa gcagtc                                                    76
```

<210> SEQ ID NO 153
<211> LENGTH: 76
<212> TYPE: DNA
<213> ORGANISM: artificial sequence
<220> FEATURE:
<223> OTHER INFORMATION: aptamere

<400> SEQUENCE: 153

```
gggtcaatgc caggtctctg ggggagggag ggtctggggg ttatacgtca ctagcaaaat    60
cggctcgcaa gcagtc                                                    76
```

<210> SEQ ID NO 154
<211> LENGTH: 76
<212> TYPE: DNA
<213> ORGANISM: artificial sequence
<220> FEATURE:
<223> OTHER INFORMATION: aptamere

<400> SEQUENCE: 154

```
gggtcaatgc caggtctcga ggggcttttg ggagggactg gtggttatac gtcccaatat    60
cggctcgcaa gcagtc                                                    76
```

<210> SEQ ID NO 155
<211> LENGTH: 76
<212> TYPE: DNA
<213> ORGANISM: artificial sequence
<220> FEATURE:
<223> OTHER INFORMATION: aptamere

<400> SEQUENCE: 155

```
gggtcaatgc caggtctcgc ggtggacggg gctggcggtt atacggtcct tacgcggtat    60
cggctcgcaa gcagtc                                                    76
```

<210> SEQ ID NO 156
<211> LENGTH: 76
<212> TYPE: DNA
<213> ORGANISM: artificial sequence
<220> FEATURE:
<223> OTHER INFORMATION: aptamere

<400> SEQUENCE: 156

```
gggtcaatgc caggtctcgc ggctgtgggg tctggtggtt atacgcacat acgcgctgat    60
cggctcgcaa gcagtc                                                    76
```

<210> SEQ ID NO 157
<211> LENGTH: 76
<212> TYPE: DNA
<213> ORGANISM: artificial sequence

```
<220> FEATURE:
<223> OTHER INFORMATION: aptamere

<400> SEQUENCE: 157
gggtcaatgc caggtctcgg gccgcgatgg agagggggtct ggtggttata cgctatgcat      60
cggctcgcaa gcagtc                                                      76

<210> SEQ ID NO 158
<211> LENGTH: 76
<212> TYPE: DNA
<213> ORGANISM: artificial sequence
<220> FEATURE:
<223> OTHER INFORMATION: aptamere

<400> SEQUENCE: 158
gggtcaatgc caggtctcac cgggtcaggc ggttatacgg gtgagggcag gtacatacat      60
cggctcgcaa gcagtc                                                      76

<210> SEQ ID NO 159
<211> LENGTH: 76
<212> TYPE: DNA
<213> ORGANISM: artificial sequence
<220> FEATURE:
<223> OTHER INFORMATION: aptamere

<400> SEQUENCE: 159
gggtcaatgc caggtctccc ggttaccgcg ctaagcttgg cgatggtgtt agtggctgat      60
cggctcgcaa gcagtc                                                      76

<210> SEQ ID NO 160
<211> LENGTH: 76
<212> TYPE: DNA
<213> ORGANISM: artificial sequence
<220> FEATURE:
<223> OTHER INFORMATION: aptamere

<400> SEQUENCE: 160
gggtcaatgc caggtctccc ggttaccgtt acgttggacg aggaatggtg ttcgtggcat      60
cggctcgcaa gcagtc                                                      76

<210> SEQ ID NO 161
<211> LENGTH: 76
<212> TYPE: DNA
<213> ORGANISM: artificial sequence
<220> FEATURE:
<223> OTHER INFORMATION: aptamere

<400> SEQUENCE: 161
gggtcaatgc caggtctccc ggttactgcc gtagttgtct tacggtggtg ttagtggcat      60
cggctcgcaa gcagtc                                                      76

<210> SEQ ID NO 162
<211> LENGTH: 76
<212> TYPE: DNA
<213> ORGANISM: artificial sequence
<220> FEATURE:
<223> OTHER INFORMATION: aptamere

<400> SEQUENCE: 162
gggtcaatgc caggtctccc ggttacttcc gtagctgtct tacggtggtg ttagtggcat      60
cggctcgcaa gcagtc                                                      76
```

```
<210> SEQ ID NO 163
<211> LENGTH: 76
<212> TYPE: DNA
<213> ORGANISM: artificial sequence
<220> FEATURE:
<223> OTHER INFORMATION: aptamere

<400> SEQUENCE: 163
gggtcaatgc caggtctccc ggttaccgca ttagtggtgt ttgtggcgtt gagatggcat      60
cggctcgcaa gcagtc                                                     76

<210> SEQ ID NO 164
<211> LENGTH: 76
<212> TYPE: DNA
<213> ORGANISM: artificial sequence
<220> FEATURE:
<223> OTHER INFORMATION: aptamere

<400> SEQUENCE: 164
gggtcaatgc caggtctccc ggttacctcc attggtggtg ttagtggctt tgtaggatat      60
cggctcgcaa gcagtc                                                     76

<210> SEQ ID NO 165
<211> LENGTH: 76
<212> TYPE: DNA
<213> ORGANISM: artificial sequence
<220> FEATURE:
<223> OTHER INFORMATION: aptamere

<400> SEQUENCE: 165
gggtcaatgc caggtctccc ggttaccagt tggtgtttgt ggctttgcac gtctgcatat      60
cggctcgcaa gcagtc                                                     76

<210> SEQ ID NO 166
<211> LENGTH: 76
<212> TYPE: DNA
<213> ORGANISM: artificial sequence
<220> FEATURE:
<223> OTHER INFORMATION: aptamere

<400> SEQUENCE: 166
gggtcaatgc caggtctccc ggttaccagt tggtgtttgt ggctttgcac gtgtgcatat      60
cggctcgcaa gcagtc                                                     76

<210> SEQ ID NO 167
<211> LENGTH: 79
<212> TYPE: DNA
<213> ORGANISM: artificial sequence
<220> FEATURE:
<223> OTHER INFORMATION: aptamere

<400> SEQUENCE: 167
gggtcaatgc caggtctccc ggttaccagt tggtgttgtt agtggctttg cacgtctgca      60
tatcggctcg caagcagtc                                                  79

<210> SEQ ID NO 168
<211> LENGTH: 76
<212> TYPE: DNA
<213> ORGANISM: artificial sequence
<220> FEATURE:
<223> OTHER INFORMATION: aptamere

<400> SEQUENCE: 168
```

```
gggtcaatgc caggtctccc ggttaccaac tatggtgtta gtggcatcga tcgggatcat    60
cggctcgcaa gcagtc                                                    76
```

<210> SEQ ID NO 169
<211> LENGTH: 74
<212> TYPE: DNA
<213> ORGANISM: artificial sequence
<220> FEATURE:
<223> OTHER INFORMATION: aptamere

<400> SEQUENCE: 169

```
gggtcaatgc caggtctccc ggttaccttt ggtgtttgtg catgggcgt cggggcatcg    60 gctcgcaagc agtc                                                      74
```

<210> SEQ ID NO 170
<211> LENGTH: 76
<212> TYPE: DNA
<213> ORGANISM: artificial sequence
<220> FEATURE:
<223> OTHER INFORMATION: aptamere

<400> SEQUENCE: 170

```
gggtcaatgc caggtctccc ggttaccgtt tggtgtttgt ggctgtgact tggataccat    60
cggctcgcaa gcagtc                                                    76
```

<210> SEQ ID NO 171
<211> LENGTH: 76
<212> TYPE: DNA
<213> ORGANISM: artificial sequence
<220> FEATURE:
<223> OTHER INFORMATION: aptamere

<400> SEQUENCE: 171

```
gggtcaatgc caggtctccc ggttaccaca ttggtgtttg tggcagtgtt attccccgat    60
cggctcgcaa gcagtc                                                    76
```

<210> SEQ ID NO 172
<211> LENGTH: 74
<212> TYPE: DNA
<213> ORGANISM: artificial sequence
<220> FEATURE:
<223> OTHER INFORMATION: aptamere

<400> SEQUENCE: 172

```
gggtcaatgc caggtctccc ggttaccaac tatgatagta tggtgtttgt ggcatgatcg    60
gctcgcaagc agtc                                                      74
```

<210> SEQ ID NO 173
<211> LENGTH: 74
<212> TYPE: DNA
<213> ORGANISM: artificial sequence
<220> FEATURE:
<223> OTHER INFORMATION: aptamere

<400> SEQUENCE: 173

```
gggtcaatgc caggtctccc ggttaccaac tatgatagta tggtgtttgt ggcgtgatcg    60
gctcgcaagc agtc                                                      74
```

<210> SEQ ID NO 174
<211> LENGTH: 76
<212> TYPE: DNA

```
<213> ORGANISM: artificial sequence
<220> FEATURE:
<223> OTHER INFORMATION: aptamere

<400> SEQUENCE: 174
gggtcaatgc caggtctccc ggttaccatc gaggacgtcg cttggtgttt gtggcatgat    60
cggctcgcaa gcagtc                                                    76

<210> SEQ ID NO 175
<211> LENGTH: 76
<212> TYPE: DNA
<213> ORGANISM: artificial sequence
<220> FEATURE:
<223> OTHER INFORMATION: aptamere

<400> SEQUENCE: 175
gggtcaatgc caggtctccc ggttaccaag atcgttgttc ttggtgttag tggcattcat    60
cggctcgcaa gcagtc                                                    76

<210> SEQ ID NO 176
<211> LENGTH: 76
<212> TYPE: DNA
<213> ORGANISM: artificial sequence
<220> FEATURE:
<223> OTHER INFORMATION: aptamere

<400> SEQUENCE: 176
gggtcaatgc caggtctccc ggttacccag tctcctgcgg tgtttgtggc atagggcaat    60
cggctcgcaa gcagtc                                                    76

<210> SEQ ID NO 177
<211> LENGTH: 76
<212> TYPE: DNA
<213> ORGANISM: artificial sequence
<220> FEATURE:
<223> OTHER INFORMATION: aptamere

<400> SEQUENCE: 177
gggtcaatgc caggtctctg aggcgcagat gtggaggctt ttacaggcgg tgcggaacat    60
cggctcgcaa gcagtc                                                    76

<210> SEQ ID NO 178
<211> LENGTH: 76
<212> TYPE: DNA
<213> ORGANISM: artificial sequence
<220> FEATURE:
<223> OTHER INFORMATION: aptamere

<400> SEQUENCE: 178
gggtcaatgc caggtctctg aggcgcagat gtggaggctt ttaccggcgg tgcggaacat    60
cggctcgcaa gcagtc                                                    76

<210> SEQ ID NO 179
<211> LENGTH: 76
<212> TYPE: DNA
<213> ORGANISM: artificial sequence
<220> FEATURE:
<223> OTHER INFORMATION: aptamere

<400> SEQUENCE: 179
gggtcaatgc caggtctctg gggcgcagat gtggaggctt ttacaggcgg tgcggaacat    60
cggctcgcaa gcagtc                                                    76
```

```
<210> SEQ ID NO 180
<211> LENGTH: 75
<212> TYPE: DNA
<213> ORGANISM: artificial sequence
<220> FEATURE:
<223> OTHER INFORMATION: aptamere

<400> SEQUENCE: 180
gggtcaatgc caggtctcgc tgcgcgcttc tgatgtactg aaggggtccg ggagtacatc     60
ggctcgcaag cagtc                                                      75

<210> SEQ ID NO 181
<211> LENGTH: 76
<212> TYPE: DNA
<213> ORGANISM: artificial sequence
<220> FEATURE:
<223> OTHER INFORMATION: aptamere

<400> SEQUENCE: 181
gggtcaatgc caggtctcca aaggggggggg ttgggggacc gtccgttgtt gatctcacat    60
cggctcgcaa gcagtc                                                     76

<210> SEQ ID NO 182
<211> LENGTH: 76
<212> TYPE: DNA
<213> ORGANISM: artificial sequence
<220> FEATURE:
<223> OTHER INFORMATION: aptamere

<400> SEQUENCE: 182
gggtcaatgc caggtctccc aggggggggg tgatataggg gaccgtccgt attggtagat    60
cggctcgcaa gcagtc                                                    76

<210> SEQ ID NO 183
<211> LENGTH: 76
<212> TYPE: DNA
<213> ORGANISM: artificial sequence
<220> FEATURE:
<223> OTHER INFORMATION: aptamere

<400> SEQUENCE: 183
gggtcaatgc caggtctcgg cgaattggtt ctgtgggggg ttggggcggc aattcgatat    60
cggctcgcaa gcagtc                                                    76

<210> SEQ ID NO 184
<211> LENGTH: 77
<212> TYPE: DNA
<213> ORGANISM: artificial sequence
<220> FEATURE:
<223> OTHER INFORMATION: aptamere

<400> SEQUENCE: 184
gggtcaatgc caggtctcga gcgtgccaaa gggttttgtg ggggggtgg ggcggcaaaa     60 tcggctcgca agcagtc                                                   77

<210> SEQ ID NO 185
<211> LENGTH: 76
<212> TYPE: DNA
<213> ORGANISM: artificial sequence
<220> FEATURE:
<223> OTHER INFORMATION: aptamere
```

```
<400> SEQUENCE: 185
gggtcaatgc caggtctctt gccatgtggt ctttgtgggt tcgggttagg gtagggttat    60
cggctcgcaa gcagtc                                                    76

<210> SEQ ID NO 186
<211> LENGTH: 75
<212> TYPE: DNA
<213> ORGANISM: artificial sequence
<220> FEATURE:
<223> OTHER INFORMATION: aptamere

<400> SEQUENCE: 186
gggtcaatgc caggtctcgt tgttctttgt gggtgcgggt tagggtaggg ggattagatc    60
ggctcgcaag cagtc                                                     75

<210> SEQ ID NO 187
<211> LENGTH: 76
<212> TYPE: DNA
<213> ORGANISM: artificial sequence
<220> FEATURE:
<223> OTHER INFORMATION: aptamere

<400> SEQUENCE: 187
gggtcaatgc caggtctcgg caaaccgtct tagtgggtgt ggggttaggg ttgggggtat    60
cggctcgcaa gcagtc                                                    76

<210> SEQ ID NO 188
<211> LENGTH: 76
<212> TYPE: DNA
<213> ORGANISM: artificial sequence
<220> FEATURE:
<223> OTHER INFORMATION: aptamere

<400> SEQUENCE: 188
gggtcaatgc caggtctcgg ctgcaaggga ttggatcaga tacggggggg acagctcgat    60
cggctcgcaa gcagtc                                                    76

<210> SEQ ID NO 189
<211> LENGTH: 76
<212> TYPE: DNA
<213> ORGANISM: artificial sequence
<220> FEATURE:
<223> OTHER INFORMATION: aptamere

<400> SEQUENCE: 189
gggtcaatgc caggtctcgg catgcggacc accaatcagc ccgggcgtcg ggcggccaat    60
cggctcgcaa gcagtc                                                    76

<210> SEQ ID NO 190
<211> LENGTH: 76
<212> TYPE: DNA
<213> ORGANISM: artificial sequence
<220> FEATURE:
<223> OTHER INFORMATION: aptamere

<400> SEQUENCE: 190
gggtcaatgc caggtctccg caggaaggcc ggaggttata acggcaactc ttcagccaat    60
cggctcgcaa gcagtc                                                    76

<210> SEQ ID NO 191
<211> LENGTH: 76
```

```
<212> TYPE: DNA
<213> ORGANISM: artificial sequence
<220> FEATURE:
<223> OTHER INFORMATION: aptamere

<400> SEQUENCE: 191
gggtcaatgc caggtctcta tgccccatcc cgcgaacacc gtcagtaacg caactgttat      60
cggctcgcaa gcagtc                                                      76

<210> SEQ ID NO 192
<211> LENGTH: 76
<212> TYPE: DNA
<213> ORGANISM: artificial sequence
<220> FEATURE:
<223> OTHER INFORMATION: aptamere

<400> SEQUENCE: 192
gggtcaatgc caggtctccg cgctcggtct agggaatacg gccgcccaat tcgttaccat      60
cggctcgcaa gcagtc                                                      76

<210> SEQ ID NO 193
<211> LENGTH: 76
<212> TYPE: DNA
<213> ORGANISM: artificial sequence
<220> FEATURE:
<223> OTHER INFORMATION: aptamere

<400> SEQUENCE: 193
gggtcaatgc caggtctcgg tgggaggtga ggtcgttgga cggtggcagg ggattttgat      60
cggctcgcaa gcagtc                                                      76

<210> SEQ ID NO 194
<211> LENGTH: 76
<212> TYPE: DNA
<213> ORGANISM: artificial sequence
<220> FEATURE:
<223> OTHER INFORMATION: aptamere

<400> SEQUENCE: 194
gggtcaatgc caggtctcgt ggaggggttg ggcgtggccc aggggagggt ggcttgttat      60
cggctcgcaa gcagtc                                                      76

<210> SEQ ID NO 195
<211> LENGTH: 76
<212> TYPE: DNA
<213> ORGANISM: artificial sequence
<220> FEATURE:
<223> OTHER INFORMATION: aptamere

<400> SEQUENCE: 195
gggtcaatgc caggtctctg cgttgggggg gtgcgcgggg gcaacgtggc acgtgaggat      60
cggctcgcaa gcagtc                                                      76

<210> SEQ ID NO 196
<211> LENGTH: 76
<212> TYPE: DNA
<213> ORGANISM: artificial sequence
<220> FEATURE:
<223> OTHER INFORMATION: aptamere

<400> SEQUENCE: 196
gggtcaatgc caggtctcgt ggtacgcgta ttggcggtag tggagtttga ggcacgagat      60
```
cggctcgcaa gcagtc 76

<210> SEQ ID NO 197
<211> LENGTH: 76
<212> TYPE: DNA
<213> ORGANISM: artificial sequence
<220> FEATURE:
<223> OTHER INFORMATION: aptamere

<400> SEQUENCE: 197
gggtcaatgc caggtctcgt gctgctgtag taggccatgt ggagggttcc agggaggtat    60
cggctcgcaa gcagtc    76

<210> SEQ ID NO 198
<211> LENGTH: 76
<212> TYPE: DNA
<213> ORGANISM: artificial sequence
<220> FEATURE:
<223> OTHER INFORMATION: aptamere

<400> SEQUENCE: 198
gggtcaatgc caggtctcgg gggactggag ggtatacgcc gaggaggttc gggggttgat    60
cggctcgcaa gcagtc    76

<210> SEQ ID NO 199
<211> LENGTH: 76
<212> TYPE: DNA
<213> ORGANISM: artificial sequence
<220> FEATURE:
<223> OTHER INFORMATION: aptamere

<400> SEQUENCE: 199
gggtcaatgc caggtctcac gtggagggtg ccagggaggt gtgagaatag gacgcgctat    60
cggctcgcaa gcagtc    76

<210> SEQ ID NO 200
<211> LENGTH: 75
<212> TYPE: DNA
<213> ORGANISM: artificial sequence
<220> FEATURE:
<223> OTHER INFORMATION: aptamere

<400> SEQUENCE: 200
gggtcaatgc caggtctcac cggggagaag gagccggacc tggggcgcgc gggcgtcgat    60
cggctcgcaa gcagt    75

<210> SEQ ID NO 201
<211> LENGTH: 76
<212> TYPE: DNA
<213> ORGANISM: artificial sequence
<220> FEATURE:
<223> OTHER INFORMATION: aptamere

<400> SEQUENCE: 201
gggtcaatgc caggtctcgg gtccagggca tcctgcgtag gtggcgggct tatgttacat    60
cggctcgcaa gcagtc    76

<210> SEQ ID NO 202
<211> LENGTH: 76
<212> TYPE: DNA
<213> ORGANISM: artificial sequence
<220> FEATURE:
<223> OTHER INFORMATION: aptamere

<400> SEQUENCE: 202
gggtcaatgc caggtctcgg gcagccctcc ttctcagtcg gtgttggtga tgtgactaat    60
cggctcgcaa gcagtc    76

<210> SEQ ID NO 203
<211> LENGTH: 76
<212> TYPE: DNA
<213> ORGANISM: artificial sequence
<220> FEATURE:
<223> OTHER INFORMATION: aptamere

<400> SEQUENCE: 203
gggtcaatgc caggtctctg gccccgatgt cctggtaaga tggatggtct gggatggtat    60
cggctcgcaa gcagtc    76

<210> SEQ ID NO 204
<211> LENGTH: 76
<212> TYPE: DNA
<213> ORGANISM: artificial sequence
<220> FEATURE:
<223> OTHER INFORMATION: aptamere

<400> SEQUENCE: 204
gggtcaatgc caggtctccc tgccgcggtg tgtgggttat tctggttatt ttggtggcat    60
cggctcgcaa gcagtc    76

<210> SEQ ID NO 205
<211> LENGTH: 76
<212> TYPE: DNA
<213> ORGANISM: artificial sequence
<220> FEATURE:
<223> OTHER INFORMATION: aptamere

<400> SEQUENCE: 205
gggtcaatgc caggtctcgg ccgggcgggt gtgggggta ctgagggtaa gtagcggcat    60
cggctcgcaa gcagtc    76

<210> SEQ ID NO 206
<211> LENGTH: 76
<212> TYPE: DNA
<213> ORGANISM: artificial sequence
<220> FEATURE:
<223> OTHER INFORMATION: aptamere

<400> SEQUENCE: 206
gggtcaatgc caggtctcgc ggtggccgac ggttacctat ggtgttagtt gtagaacaat    60
cggctcgcaa gcagtc    76

<210> SEQ ID NO 207
<211> LENGTH: 76
<212> TYPE: DNA
<213> ORGANISM: artificial sequence
<220> FEATURE:
<223> OTHER INFORMATION: aptamere

<400> SEQUENCE: 207
gggtcaatgc caggtctcgg attcaggtgg ccgaacggtg ttgtgttgag tacggtggat    60
cggctcgcaa gcagtc    76

<210> SEQ ID NO 208

```
<211> LENGTH: 75
<212> TYPE: DNA
<213> ORGANISM: artificial sequence
<220> FEATURE:
<223> OTHER INFORMATION: aptamere

<400> SEQUENCE: 208
gggtcaatgc caggtctcca agggagcgag agttggcgcg tctacacata ccctgacatc      60
ggctcgcaag cagtc                                                      75

<210> SEQ ID NO 209
<211> LENGTH: 76
<212> TYPE: DNA
<213> ORGANISM: artificial sequence
<220> FEATURE:
<223> OTHER INFORMATION: aptamere

<400> SEQUENCE: 209
gggtcaatgc caggtctcgg acgcaggggt ggacgctata agccatggat agttcagtat      60
cggctcgcaa gcagtc                                                     76

<210> SEQ ID NO 210
<211> LENGTH: 76
<212> TYPE: DNA
<213> ORGANISM: artificial sequence
<220> FEATURE:
<223> OTHER INFORMATION: aptamere

<400> SEQUENCE: 210
gggtcaatgc caggtctcgt cgacacgggg gggatatcgc tatcgcaatc tgatcgctat      60
cggctcgcaa gcagtc                                                     76

<210> SEQ ID NO 211
<211> LENGTH: 76
<212> TYPE: DNA
<213> ORGANISM: artificial sequence
<220> FEATURE:
<223> OTHER INFORMATION: aptamere

<400> SEQUENCE: 211
gggtcaatgc caggtctcaa ggcggggcgg tactgtactc tcgtaatact gttccccgat      60
cggctcgcaa gcagtc                                                     76

<210> SEQ ID NO 212
<211> LENGTH: 76
<212> TYPE: DNA
<213> ORGANISM: artificial sequence
<220> FEATURE:
<223> OTHER INFORMATION: aptamere

<400> SEQUENCE: 212
gggtcaatgc caggtctcca aagggggggg ttgggggacc gtccgttgtt gatctcacat      60
cggctcgcaa gcagtc                                                     76

<210> SEQ ID NO 213
<211> LENGTH: 76
<212> TYPE: DNA
<213> ORGANISM: artificial sequence
<220> FEATURE:
<223> OTHER INFORMATION: aptamere

<400> SEQUENCE: 213
gggtcaatgc caggtctccc agggggggggg tgatataggg gaccgtccgt attggtagat     60
```

```
cggctcgcaa gcagtc                                                        76

<210> SEQ ID NO 214
<211> LENGTH: 76
<212> TYPE: DNA
<213> ORGANISM: artificial sequence
<220> FEATURE:
<223> OTHER INFORMATION: aptamere

<400> SEQUENCE: 214
gggtcaatgc caggtctcta tgggtgcact tgtcacgtac cttgggactt tcaagggtat        60
cggctcgcaa gcagtc                                                        76

<210> SEQ ID NO 215
<211> LENGTH: 76
<212> TYPE: DNA
<213> ORGANISM: artificial sequence
<220> FEATURE:
<223> OTHER INFORMATION: aptamere

<400> SEQUENCE: 215
gggtcaatgc caggtctcgg ggggaatagt caagtattga gcgggacttt cgttgcccat        60
cggctcgcaa gcagtc                                                        76

<210> SEQ ID NO 216
<211> LENGTH: 76
<212> TYPE: DNA
<213> ORGANISM: artificial sequence
<220> FEATURE:
<223> OTHER INFORMATION: aptamere

<400> SEQUENCE: 216
gggtcaatgc caggtctcac gggggtataa tgttcattga atcaggccgc ccgtgtgtat        60
cggctcgcaa gcagtc                                                        76

<210> SEQ ID NO 217
<211> LENGTH: 76
<212> TYPE: DNA
<213> ORGANISM: artificial sequence
<220> FEATURE:
<223> OTHER INFORMATION: aptamere

<400> SEQUENCE: 217
gggtcaatgc caggtctcac gcggggataa aagtctgtct attggtgaag gcacgccaat        60
cggctcgcaa gcagtc                                                        76

<210> SEQ ID NO 218
<211> LENGTH: 76
<212> TYPE: DNA
<213> ORGANISM: artificial sequence
<220> FEATURE:
<223> OTHER INFORMATION: aptamere

<400> SEQUENCE: 218
gggtcaatgc caggtctccg ggcggtagaa gttggctcgt cggttaggtg ggaagggtat        60
cggctcgcaa gcagtc                                                        76

<210> SEQ ID NO 219
<211> LENGTH: 76
<212> TYPE: DNA
<213> ORGANISM: artificial sequence
<220> FEATURE:
```

```
<223> OTHER INFORMATION: aptamere

<400> SEQUENCE: 219
gggtcaatgc caggtctcca ctggcgaaga gacgttggct tcgttgcggc ggcccagtat      60
cggctcgcaa gcagtc                                                     76

<210> SEQ ID NO 220
<211> LENGTH: 76
<212> TYPE: DNA
<213> ORGANISM: artificial sequence
<220> FEATURE:
<223> OTHER INFORMATION: aptamere

<400> SEQUENCE: 220
gggtcaatgc caggtctcgt cgtggtgccg aagggagacg aattcgattg ccggtggcat      60
cggctcgcaa gcagtc                                                     76

<210> SEQ ID NO 221
<211> LENGTH: 76
<212> TYPE: DNA
<213> ORGANISM: artificial sequence
<220> FEATURE:
<223> OTHER INFORMATION: aptamere

<400> SEQUENCE: 221
gggtcaatgc caggtctcgg gcggtggaag tggggagaaa gtgggtattg tggccagtat      60
cggctcgcaa gcagtc                                                     76

<210> SEQ ID NO 222
<211> LENGTH: 76
<212> TYPE: DNA
<213> ORGANISM: artificial sequence
<220> FEATURE:
<223> OTHER INFORMATION: aptamere

<400> SEQUENCE: 222
gggtcaatgc caggtctcgg cagaacggga catattggaa tgcctctgtg tgtttagtat      60
cggctcgcaa gcagtc                                                     76

<210> SEQ ID NO 223
<211> LENGTH: 76
<212> TYPE: DNA
<213> ORGANISM: artificial sequence
<220> FEATURE:
<223> OTHER INFORMATION: aptamere

<400> SEQUENCE: 223
gggtcaatgc caggtctcct gaacggtgga attatgtcgg tgcgtgtacc tattcgggat      60
cggctcgcaa gcagtc                                                     76

<210> SEQ ID NO 224
<211> LENGTH: 76
<212> TYPE: DNA
<213> ORGANISM: artificial sequence
<220> FEATURE:
<223> OTHER INFORMATION: aptamere

<400> SEQUENCE: 224
gggtcaatgc caggtctcgg acaccagcac gtaggggagt atatatcaat gggggggctat     60 cggctcgcaa gcagtc                                                     76
```

```
<210> SEQ ID NO 225
<211> LENGTH: 76
<212> TYPE: DNA
<213> ORGANISM: artificial sequence
<220> FEATURE:
<223> OTHER INFORMATION: aptamere

<400> SEQUENCE: 225
gggtcaatgc caggtctccg acgcgagagc cagggcgcgg tgtcttcttg tggggtagat    60
cggctcgcaa gcagtc                                                   76

<210> SEQ ID NO 226
<211> LENGTH: 76
<212> TYPE: DNA
<213> ORGANISM: artificial sequence
<220> FEATURE:
<223> OTHER INFORMATION: aptamere

<400> SEQUENCE: 226
gggtcaatgc caggtctctg tgagcgcagc actgtgtacc ccctattgt tatctggaat     60 cggctcgcaa gcagtc                                                   76

<210> SEQ ID NO 227
<211> LENGTH: 76
<212> TYPE: DNA
<213> ORGANISM: artificial sequence
<220> FEATURE:
<223> OTHER INFORMATION: aptamere

<400> SEQUENCE: 227
gggtcaatgc caggtctcgg gattttgacg cgcacgtggg accacccctg cctagttcat    60
cggctcgcaa gcagtc                                                   76

<210> SEQ ID NO 228
<211> LENGTH: 76
<212> TYPE: DNA
<213> ORGANISM: artificial sequence
<220> FEATURE:
<223> OTHER INFORMATION: aptamere

<400> SEQUENCE: 228
gggtcaatgc caggtctcaa acccgatcca cgcccctgt agtgatccta agatgatcat    60
cggctcgcaa gcagtc                                                   76

<210> SEQ ID NO 229
<211> LENGTH: 76
<212> TYPE: DNA
<213> ORGANISM: artificial sequence
<220> FEATURE:
<223> OTHER INFORMATION: aptamere

<400> SEQUENCE: 229
gggtcaatgc caggtctcaa cgccccgccc actatgcgcc gtatatggac cagatcctat    60
cggctcgcaa gcagtc                                                   76

<210> SEQ ID NO 230
<211> LENGTH: 76
<212> TYPE: DNA
<213> ORGANISM: artificial sequence
<220> FEATURE:
<223> OTHER INFORMATION: aptamere

<400> SEQUENCE: 230
```

```
gggtcaatgc caggtctcag cacccggggc tgaaagaag gcgaggtaat atggacttat    60
cggctcgcaa gcagtc                                                   76

<210> SEQ ID NO 231
<211> LENGTH: 76
<212> TYPE: DNA
<213> ORGANISM: artificial sequence
<220> FEATURE:
<223> OTHER INFORMATION: aptamere

<400> SEQUENCE: 231
gggtcaatgc caggtctcca ccgcctgaac gaacaagaaa gcgagaacca ggagctacat    60
cggctcgcaa gcagtc                                                   76

<210> SEQ ID NO 232
<211> LENGTH: 75
<212> TYPE: DNA
<213> ORGANISM: artificial sequence
<220> FEATURE:
<223> OTHER INFORMATION: aptamere

<400> SEQUENCE: 232
gggtcaatgc caggtctcgc tgcgcgcttc tgatgtactg aaggggtccg ggagtacatc    60
ggctcgcaag cagtc                                                    75

<210> SEQ ID NO 233
<211> LENGTH: 16
<212> TYPE: DNA
<213> ORGANISM: artificial sequence
<220> FEATURE:
<223> OTHER INFORMATION: consensus

<400> SEQUENCE: 233
gggtcggggt tatacg                                                   16

<210> SEQ ID NO 234
<211> LENGTH: 18
<212> TYPE: DNA
<213> ORGANISM: artificial sequence
<220> FEATURE:
<223> OTHER INFORMATION: consensus

<400> SEQUENCE: 234
gggtctggtg gttatacg                                                 18

<210> SEQ ID NO 235
<211> LENGTH: 21
<212> TYPE: DNA
<213> ORGANISM: artificial sequence
<220> FEATURE:
<223> OTHER INFORMATION: consensus

<400> SEQUENCE: 235
ccggttacct ggtgttgtgg c                                             21

<210> SEQ ID NO 236
<211> LENGTH: 22
<212> TYPE: DNA
<213> ORGANISM: artificial sequence
<220> FEATURE:
<223> OTHER INFORMATION: consensus

<400> SEQUENCE: 236
ggaggctttt acaggcggtg cg                                            22
```

<210> SEQ ID NO 237
<211> LENGTH: 29
<212> TYPE: DNA
<213> ORGANISM: artificial sequence
<220> FEATURE:
<223> OTHER INFORMATION: consensus

<400> SEQUENCE: 237
ggggggggtt ggggggaccgt ccgtttgat                              29

<210> SEQ ID NO 238
<211> LENGTH: 15
<212> TYPE: DNA
<213> ORGANISM: artificial sequence
<220> FEATURE:
<223> OTHER INFORMATION: consensus

<400> SEQUENCE: 238 tgtgggggt tgggg                                               15

<210> SEQ ID NO 239
<211> LENGTH: 38
<212> TYPE: DNA
<213> ORGANISM: Artificial sequence
<220> FEATURE:
<223> OTHER INFORMATION: Aptamere

<400> SEQUENCE: 239
caggtctcgg gcacgggtca ggcggttata cggtgccc                     38

<210> SEQ ID NO 240
<211> LENGTH: 40
<212> TYPE: DNA
<213> ORGANISM: Artificial sequence
<220> FEATURE:
<223> OTHER INFORMATION: Aptamere

<400> SEQUENCE: 240
gggcacgggt caggcggtta tacggtgccc attgttcttt                   40

<210> SEQ ID NO 241
<211> LENGTH: 35
<212> TYPE: DNA
<213> ORGANISM: Artificial Sequence
<220> FEATURE:
<223> OTHER INFORMATION: Aptamere

<400> SEQUENCE: 241
gggcacgggt caggcggtta tacggtgccc attgt                        35

<210> SEQ ID NO 242
<211> LENGTH: 30
<212> TYPE: DNA
<213> ORGANISM: Artificial Sequence
<220> FEATURE:
<223> OTHER INFORMATION: Aptamere

<400> SEQUENCE: 242
gggcacgggt caggcggtta tacggtgccc                              30

<210> SEQ ID NO 243
<211> LENGTH: 24
<212> TYPE: DNA
<213> ORGANISM: Artificial Sequence
<220> FEATURE:

```
<223> OTHER INFORMATION: Aptamere

<400> SEQUENCE: 243
cacgggtcag gcggttatac ggtg                                          24
```